(12) United States Patent
Hwang et al.

(10) Patent No.: US 12,207,972 B2
(45) Date of Patent: Jan. 28, 2025

(54) APPARATUSES AND METHODS FOR CONFIGURING ULTRASOUND DEVICES

(71) Applicant: BFLY Operations, Inc., Guilford, CT (US)

(72) Inventors: Sewook Hwang, Carlisle, MA (US);
Jungwook Yang, Newton, MA (US);
Kailiang Chen, Branford, CT (US);
Nevada J. Sanchez, Guilford, CT (US)

(73) Assignee: BFLY Operations, Inc., Burlington, MA (US)

( * ) Notice: Subject to any disclaimer, the term of this patent is extended or adjusted under 35 U.S.C. 154(b) by 181 days.

(21) Appl. No.: 17/868,591

(22) Filed: Jul. 19, 2022

(65) Prior Publication Data
US 2023/0022229 A1    Jan. 26, 2023

Related U.S. Application Data

(60) Provisional application No. 63/223,954, filed on Jul. 20, 2021.

(51) Int. Cl.
| | |
|---|---|
| *G01S 7/52* | (2006.01) |
| *A61B 8/00* | (2006.01) |
| *A61B 8/08* | (2006.01) |

(52) U.S. Cl.
CPC ............. *A61B 8/52* (2013.01); *A61B 8/0883* (2013.01); *A61B 8/4477* (2013.01); *A61B 8/469* (2013.01); *A61B 8/54* (2013.01); *A61B 8/56* (2013.01); *G01S 7/52028* (2013.01)

(58) Field of Classification Search
CPC ....... A61B 8/52; A61B 8/0883; A61B 8/4477; A61B 8/469; A61B 8/54; A61B 8/56; A61B 8/08; A61B 8/585; A61B 8/58; G01S 7/52028; G01S 15/8927; G01S 15/8925

See application file for complete search history.

(56) References Cited

U.S. PATENT DOCUMENTS

| | | |
|---|---|---|
| 6,673,016 B1 | 1/2004 | Bolorforosh et al. |
| 2005/0131297 A1 | 6/2005 | Nishigaki et al. |
| 2014/0031693 A1* | 1/2014 | Solek ............... A61B 8/54 600/447 |
| 2017/0360397 A1 | 12/2017 | Rothberg et al. |
| 2017/0363725 A1 | 12/2017 | Ignjatovic et al. |

FOREIGN PATENT DOCUMENTS

| | | | |
|---|---|---|---|
| CA | 2362628 | * | 9/2000 |
| WO | WO 03065070 | * | 8/2003 |
| WO | WO 2020016018 | * | 7/2019 |

OTHER PUBLICATIONS

International Search Report and Written Opinion of the International Searching Authority issued in corresponding application PCT/US22/37607 mailed Oct. 25, 2022 (17 pages).

* cited by examiner

*Primary Examiner* — Alexei Bykhovski
(74) *Attorney, Agent, or Firm* — Carter, DeLuca & Farrell LLP

(57) ABSTRACT

Ultrasound devices are disclosed. The ultrasound devices have an elevational dimension. Different percentages of the aperture of the ultrasound device corresponding to different percentages of the elevational dimension are utilized in different applications. The resolution of imagine may be adjusted in connection with usage of different percentages of the aperture.

20 Claims, 19 Drawing Sheets

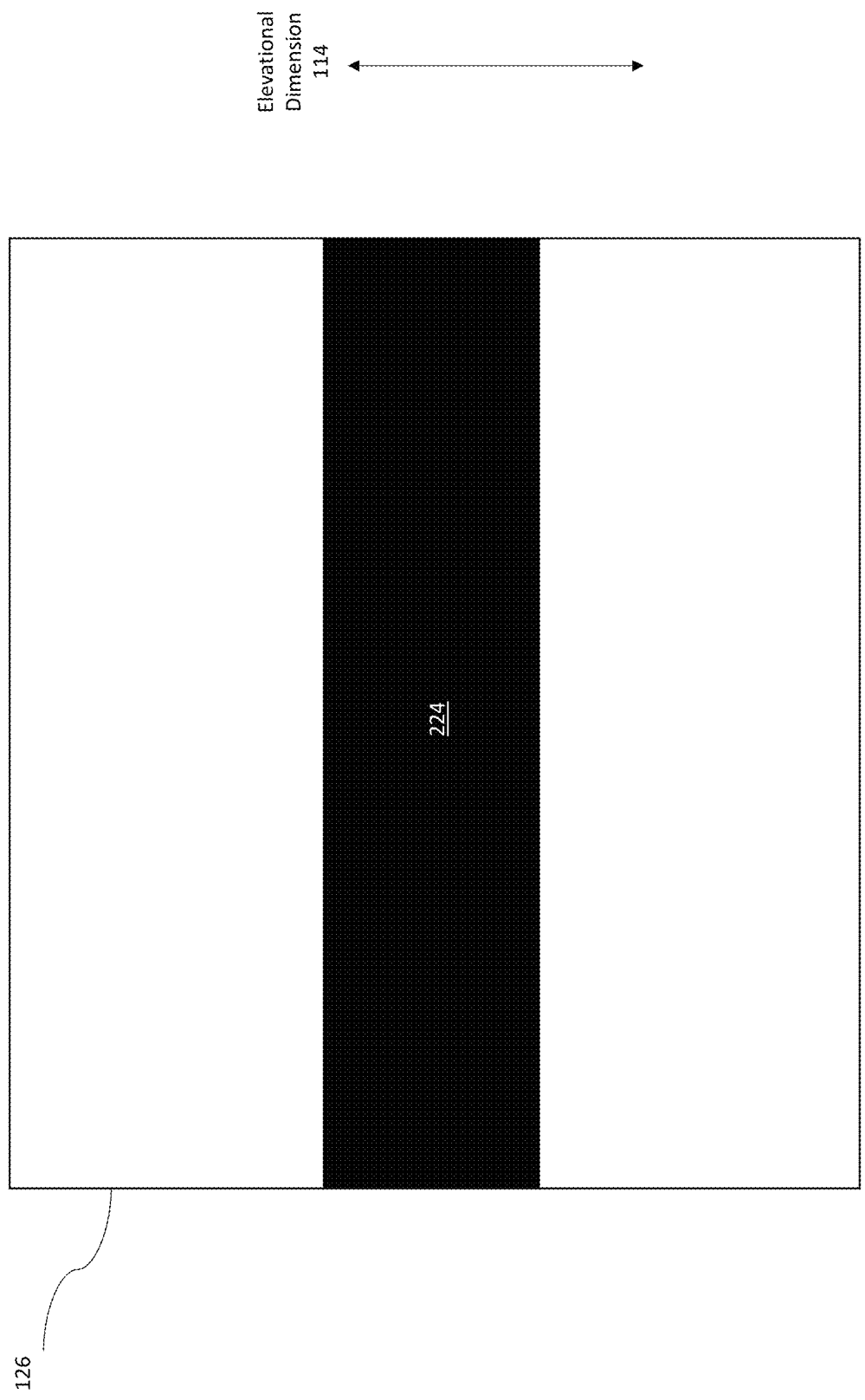

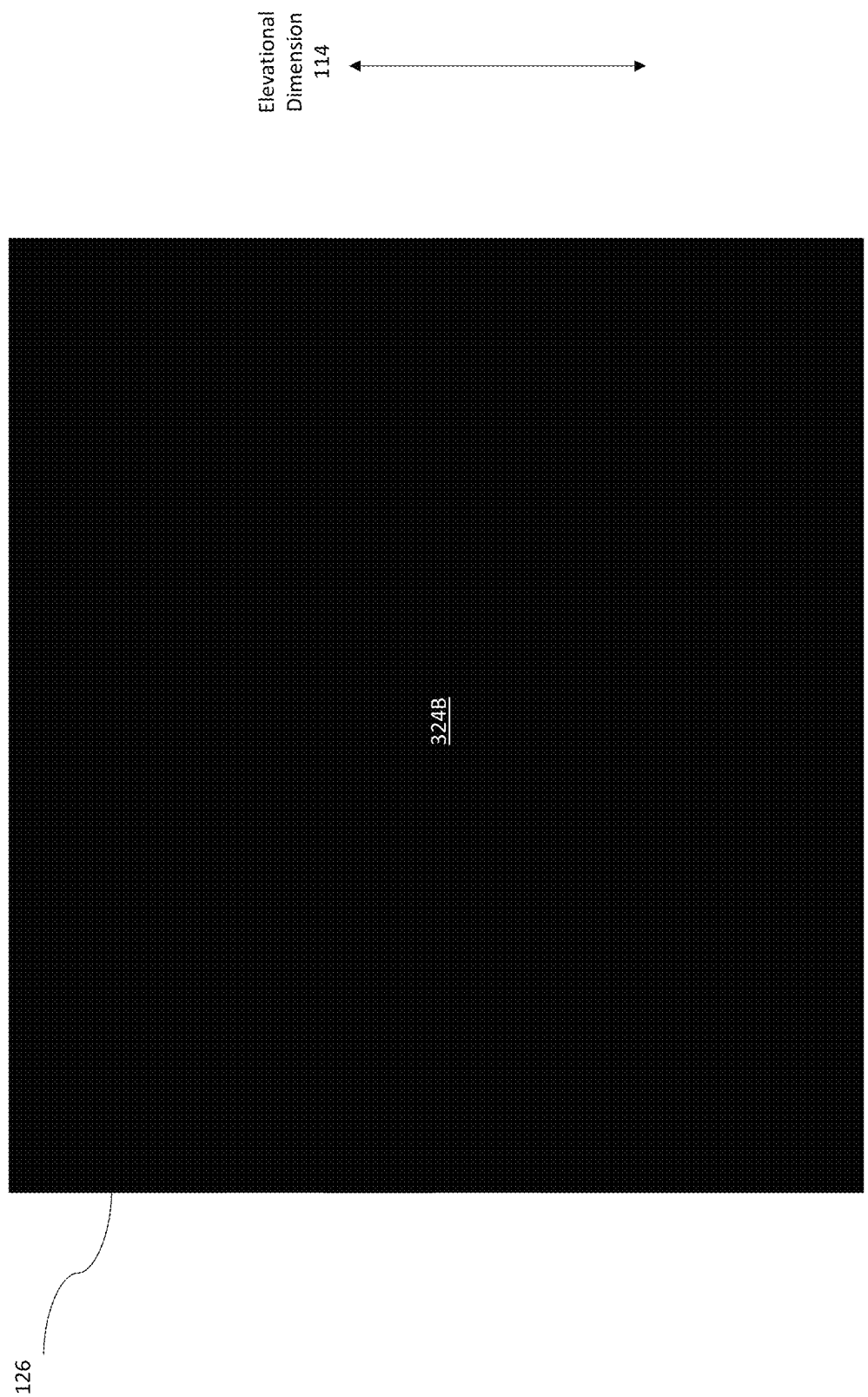

APPARATUSES AND METHODS FOR CONFIGURING ULTRASOUND DEVICES

RELATED APPLICATIONS

This application claims the benefit under 35 U.S.C. § 119(e) of U.S. Provisional Application Ser. No. 63/223,954, filed Jul. 20, 2021, and entitled "APPARATUSES AND METHODS FOR CONFIGURING ULTRASOUND DEVICES," which is hereby incorporated by reference herein in its entirety.

FIELD

Generally, the aspects of the technology described herein relate to ultrasound devices. Certain aspects relate to configuring ultrasound devices.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

Ultrasound devices are disclosed. The ultrasound devices have an elevational dimension. Different percentages of the aperture of the ultrasound device corresponding to different percentages of the elevational dimension are utilized in different applications. The resolution of imagine may be adjusted in connection with usage of different percentages of the aperture.

According to one aspect an ultrasound device is provided, comprising: an ultrasonic transducer array, and control circuitry. The control circuitry is configured to: receive a first indication to configure the ultrasound device in a first configuration that includes processing data from k1% of an elevational aperture of the ultrasonic transducer array by coupling n1 output terminals from analog receive circuits to each of multiple analog combination circuits; configure the ultrasound device in the first configuration; receive a second indication to configure the ultrasound device in a second configuration that includes processing data from k2% of the elevational aperture of the ultrasonic transducer array by coupling n2 output terminals from analog receive circuits to each of multiple analog combination circuits, wherein n2 is greater than n1 and k2 is greater than k1; or n2 is less than n1 and k2 is less than k1. The control circuitry is further configured to configure the ultrasound device in the second configuration.

According to an aspect of the present application, an ultrasound device is provided, comprising: a plurality of ultrasonic transducers; a plurality of analog receive circuits each configured to receive and/or process an analog ultrasound signal from one or more corresponding ultrasonic transducers of the plurality of ultrasonic transducers; a plurality of analog combination circuits each configured to output a single analog output by combining multiple analog inputs; switching circuitry comprising a plurality of switches each switchably coupling an output of a particular analog receive circuit of the plurality of analog receive circuits to an input of a particular analog combination circuit of the plurality of analog combination circuits; wherein the control circuitry is configured, when configuring the ultrasound device in the first and/or second configurations, to control the switching circuitry to cause particular outputs of the plurality of analog receive circuits to be coupled as inputs to particular analog combination circuits of the plurality of analog combination circuits; an output of a first analog receive circuit of the plurality of analog receive circuits is switchably coupled to inputs of multiple but not all analog combination circuits of the plurality of analog combination circuits.

According to an aspect of the present application, an ultrasound device is provided, comprising: a plurality of ultrasonic transducers; a plurality of analog receive circuits each configured to receive and/or process an analog ultrasound signal from one or more corresponding ultrasonic transducers of the plurality of ultrasonic transducers; a plurality of analog combination circuits each configured to output a single analog output by combining multiple analog inputs; switching circuitry comprising a plurality of switches each switchably coupling an output of a particular analog receive circuit to an input of a particular analog combination circuit; and control circuitry. The control circuitry is configured to: receive a first indication to configure an ultrasound device in a first configuration that includes coupling an output of a particular analog receive circuit of the plurality of analog receive circuits to a first analog combination circuit of the plurality of analog combination circuit; configure the ultrasound device in the first configuration; receive a second indication to configure an ultrasound device in a second configuration that includes coupling the output of the particular analog receive circuit of the plurality of analog receive circuits to a second analog combination circuit of the plurality of analog combination circuit, wherein the first and second analog combination circuits are different; and configure the ultrasound device in the second configuration.

According to an aspect of the present application, a processing device is provided in operative communication with an ultrasound device, the processing device configured to: receive a selection of a first anatomy for imaging; generate a first configuration indication associated with the first anatomy, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

According to an aspect of the present application, a processing device is provided in operative communication with an ultrasound device, the processing device configured to: receive a selection of a first imaging depth; generate a first configuration indication associated with the first imaging depth, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

According to an aspect of the present application, a processing device is provided in operative communication with an ultrasound device, the processing device configured to: determine a first power level of the ultrasound device; generate a first configuration indication associated with the first power level, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

According to an aspect of the present application, a processing device is provided in operative communication with an ultrasound device, the processing device configured to: receive a selection of a first power mode; generate a first configuration indication associated with the first power mode, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

According to an aspect of the present application, an ultrasound device is provided, comprising: an ultrasonic transducer array; configurable processing circuitry coupled to the ultrasonic transducer array; and control circuitry coupled to the configurable processing circuitry and configured to set the configurable processing circuitry to a first configuration exhibiting a first elevational aperture percentage and first resolution and then to a second configuration exhibiting a second elevational aperture percentage different than the first elevational aperture percentage and a second resolution different than the first resolution.

According to an aspect of the present application, an ultrasound device is provided, comprising: a housing; an ultrasonic transducer array disposed within the housing; and configurable processing circuitry disposed within the housing and coupled to the ultrasonic transducer array, configured to process output signals of the ultrasonic transducer array, and configurable in a first configuration exhibiting a first elevational aperture percentage and first resolution and a second configuration exhibiting a second elevational aperture percentage different than the first elevational aperture percentage and a second resolution different than the first resolution.

Some aspects provide methods of operating the ultrasound devices and processing devices described above.

Some aspects include at least one non-transitory computer-readable storage medium storing processor-executable instructions that, when executed by at least one processor, cause the at least one processor to perform the above aspects and embodiments. Some aspects include an apparatus having a processing device configured to perform the above aspects and embodiments.

According to an aspect of the present disclosure, there is provided an ultrasound device, comprising an ultrasonic transducer array comprising a plurality of ultrasonic transducers, a plurality of analog receive circuits each configured to receive and/or process an analog ultrasound signal from one or more corresponding ultrasonic transducers of the plurality of ultrasonic transducers, a plurality of analog combination circuits each configured to output a single analog output by combining multiple analog inputs, switching circuitry comprising a plurality of switches each switchably coupling an output of a particular analog receive circuit of the plurality of analog receive circuits to an input of a particular analog combination circuit of the plurality of analog combination circuits, and control circuitry configured to receive a first indication to configure the ultrasound device in a first configuration that includes processing data from k1% of an elevational aperture of the ultrasonic transducer array by coupling n1 output terminals from analog receive circuits of the plurality of analog receive circuits to each of multiple analog combination circuits of the plurality of analog combination circuits, configure the ultrasound device in the first configuration, comprising controlling the switching circuitry to cause particular outputs of the plurality of analog receive circuits to be coupled as inputs to particular analog combination circuits of the plurality of analog combination circuits, receive a second indication to configure the ultrasound device in a second configuration that includes processing data from k2% of the elevational aperture of the ultrasonic transducer array by coupling n2 output terminals from analog receive circuits of the plurality of analog receive circuits to each of multiple analog combination circuits of the plurality of analog combination circuits, wherein n2 is greater than n1 and k2 is greater than k1 or n2 is less than n1 and k2 is less than k1, and configure the ultrasound device in the second configuration, comprising controlling the switching circuitry to cause particular outputs of the plurality of analog receive circuits to be coupled as inputs to particular analog combination circuits of the plurality of analog combination circuits. An output of a first analog receive circuit of the plurality of analog receive circuits is switchably coupled to inputs of multiple but not all analog combination circuits of the plurality of analog combination circuits.

In some embodiments, outputs of fewer than 75% of the plurality of analog receive circuits are switchably coupled to inputs of all analog combination circuits of the plurality of analog combination circuits.

In some embodiments, the output of the first analog receive circuit of the plurality of analog receive circuits is switchably coupled to inputs of a first number of analog combination circuits of the plurality of analog combination circuits, an output of a second analog receive circuit of the plurality of analog receive circuits is switchably coupled to inputs of a second number of analog combination circuits of the plurality of analog combination circuits, and the first and second numbers are different.

In some embodiments, when k2 is less than k1: k1 is 100 and k2 is 50, k1 is 100 and k2 is 25, or k1 is 50 and k2 is 25; when k2 is greater than k1: k1 is 50 and k2 is 100, k1 is 25 and k2 is 100, or k1 is 25 and k2 is 50; when n2 is less than n1: n1 is 8 and n2 is 4, n1 is 8 and n2 is 2, or n1 is 4 and n2 is 2; and when n2 is greater than n1: n1 is 4 and n2 is 8, n1 is 2 and n2 is 8, or n1 is 2 and n2 is 4.

In some embodiments, the control circuitry is configured, when receiving the indication to configure the ultrasound device in the first configuration, to receive the indication based on (a) a user selection of an anatomy for imaging, (b) a user selection of an imaging depth, (c) a power level of the ultrasound device, or (d) a user selection of a power mode for the ultrasound device.

In some embodiments, the first configuration is a configuration associated with imaging a heart and/or the second configuration is a configuration associated with imaging an abdomen and n2 is greater than n1 and k2 is greater than k1.

In some embodiments, the first configuration is a configuration associated with imaging at a first imaging depth, the second configuration is a configuration associated with imaging at a second imaging depth, the first imaging depth is deeper than the second imaging depth, and n2 is less than n1 and k2 is less than k1.

In some embodiments, the first configuration is a configuration associated with imaging at a first power level of the ultrasound device, the second configuration is a configuration associated with imaging at a second power level of the ultrasound device, the first power level is greater than the power level, and n2 is less than n1 and k2 is less than k1.

According to an aspect of the present disclosure, there is provided a method of controlling an ultrasound device comprising an ultrasonic transducer array comprising a plurality of ultrasonic transducers, a plurality of analog receive circuits each configured to receive and/or process an analog ultrasound signal from one or more corresponding ultrasonic transducers of the plurality of ultrasonic transducers, a plurality of analog combination circuits each configured to output a single analog output by combining multiple analog inputs, and switching circuitry comprising a plurality of switches each switchably coupling an output of a particular analog receive circuit of the plurality of analog receive circuits to an input of a particular analog combination circuit of the plurality of analog combination circuits, the method comprising receiving, with control circuitry, a first indication to configure the ultrasound device in a first configuration that includes processing data from k1% of an elevational aperture of the ultrasonic transducer array by coupling n1 output terminals from analog receive circuits of the plurality of analog receive circuits to each of multiple analog combination circuits of the plurality of analog combination circuits, configuring, with the control circuitry, the ultrasound device in the first configuration, comprising controlling the switching circuitry to cause particular outputs of the plurality of analog receive circuits to be coupled as inputs to particular analog combination circuits of the plurality of analog combination circuits, receiving, with the control circuitry, a second indication to configure the ultrasound device in a second configuration that includes processing data from k2% of the elevational aperture of the ultrasonic transducer array by coupling n2 output terminals from analog receive circuits of the plurality of analog receive circuits to each of multiple analog combination circuits of the plurality of analog combination circuits, wherein n2 is greater than n1 and k2 is greater than k1 or n2 is less than n1 and k2 is less than k1, and configuring, with the control circuitry, the ultrasound device in the second configuration, comprising controlling the switching circuitry to cause particular outputs of the plurality of analog receive circuits to be coupled as inputs to particular analog combination circuits of the plurality of analog combination circuits. An output of a first analog receive circuit of the plurality of analog receive circuits is switchably coupled to inputs of multiple but not all analog combination circuits of the plurality of analog combination circuits.

In some embodiments, outputs of fewer than 75% of the plurality of analog receive circuits are switchably coupled to inputs of all analog combination circuits of the plurality of analog combination circuits, the output of the first analog receive circuit of the plurality of analog receive circuits is switchably coupled to inputs of a first number of analog combination circuits of the plurality of analog combination circuits, an output of a second analog receive circuit of the plurality of analog receive circuits is switchably coupled to inputs of a second number of analog combination circuits of the plurality of analog combination circuits, and the first and second numbers are different.

In some embodiments, receiving, with the control circuitry, the indication to configure the ultrasound device in the first configuration, comprises receiving, with the control circuitry, the indication based on (a) a user selection of an anatomy for imaging, (b) a user selection of an imaging depth, (c) a power level of the ultrasound device, or (d) a user selection of a power mode for the ultrasound device.

In some embodiments, the method further comprises imaging a heart using the first configuration and/or imaging an abdomen using the second configuration, wherein n2 is greater than n1 and k2 is greater than k1.

In some embodiments, the method further comprises imaging at a first imaging depth using the first configuration and imaging at a second imaging depth using the second configuration, wherein the first imaging depth is deeper than the second imaging depth and n2 is less than n1 and k2 is less than k1.

In some embodiments, the method further comprises imaging at a first power level of the ultrasound device using the first configuration and imaging at a second power level of the ultrasound device using the second configuration, wherein the first power level is greater than the power level and n2 is less than n1 and k2 is less than k1.

According to an aspect of the present disclosure, there is provided an ultrasound device, comprising an ultrasonic transducer array and control circuitry configured to receive a first indication to configure the ultrasound device in a first configuration that includes processing data from k1% of an elevational aperture of the ultrasonic transducer array by coupling n1 output terminals from analog receive circuits to each of multiple analog combination circuits, configure the ultrasound device in the first configuration, receive a second indication to configure the ultrasound device in a second configuration that includes processing data from k2% of the elevational aperture of the ultrasonic transducer array by coupling n2 output terminals from analog receive circuits to each of multiple analog combination circuits, wherein n2 is greater than n1 and k2 is greater than k1 or n2 is less than n1 and k2 is less than k1, and configure the ultrasound device in the second configuration.

In some embodiments, when k2 is less than k1: k1 is 100 and k2 is 50, k1 is 100 and k2 is 25, or k1 is 50 and k2 is 25; when k2 is greater than k1: k1 is 50 and k2 is 100, k1 is 25 and k2 is 100, or k1 is 25 and k2 is 50; when n2 is less than n1: n1 is 8 and n2 is 4, n1 is 8 and n2 is 2, or n1 is 4 and n2 is 2; and when n2 is greater than n1: n1 is 4 and n2 is 8, n1 is 2 and n2 is 8, or n1 is 2 and n2 is 4.

In some embodiments, the control circuitry is configured, when receiving the indication to configure the ultrasound device in the first configuration, to receive the indication based on (a) a user selection of an anatomy for imaging, (b) a user selection of an imaging depth, (c) a power level of the ultrasound device, or (d) a user selection of a power mode for the ultrasound device.

In some embodiments, the first configuration is a configuration associated with imaging a heart and/or the second configuration is a configuration associated with imaging an abdomen and n2 is greater than n1 and k2 is greater than k1.

In some embodiments, the first configuration is a configuration associated with imaging at a first imaging depth, the second configuration is a configuration associated with imaging at a second imaging depth, the first imaging depth is deeper than the second imaging depth, and n2 is less than n1 and k2 is less than k1.

In some embodiments, the first configuration is a configuration associated with imaging at a first power level of the ultrasound device, the second configuration is a configuration associated with imaging at a second power level of the ultrasound device, the first power level is greater than the power level, and n2 is less than n1 and k2 is less than k1.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 2 illustrates the centermost 25% of the elevational aperture of the ultrasonic transducer array of FIGS. 1A and 1B, in accordance with certain embodiments described herein.

FIG. 3B illustrates the full elevational aperture of the ultrasonic transducer array of FIGS. 1A and 1B, in accordance with certain embodiments described herein.

FIG. 14 is shown on two sheets that form in effect a single complete figure.

FIG. 15 is shown on four sheets that form in effect a single complete figure.

DETAILED DESCRIPTION

Figure 1A:
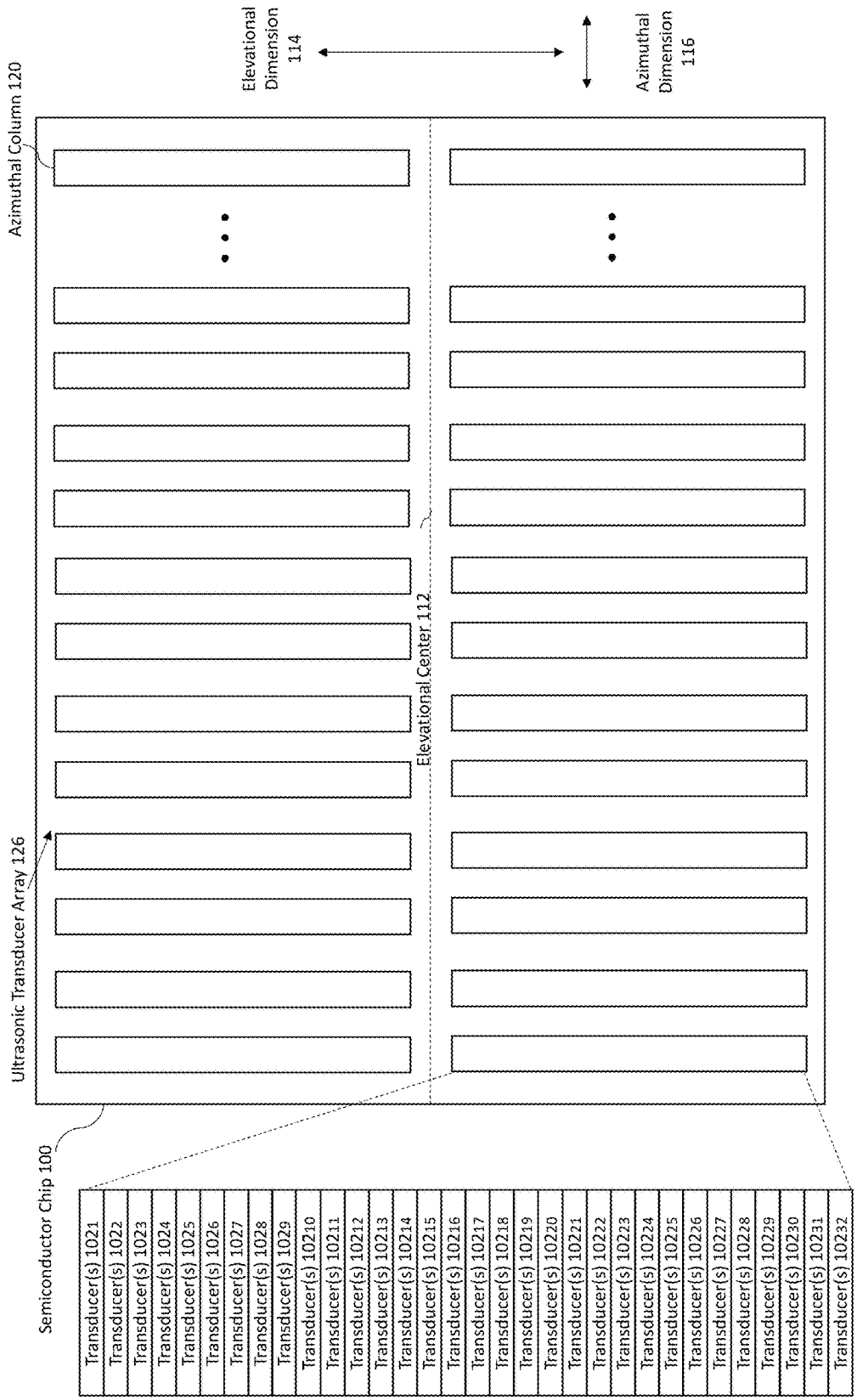
FIGS. 1A and 1B illustrate a schematic physical diagram of a semiconductor chip having integrated thereon an ultrasonic transducer array made up of ultrasonic transducers and ultrasound circuitry, in accordance with certain embodiments described herein.

The ultrasonic transducer array of an ultrasound device may have an azimuthal dimension and an elevational dimension. The totality of the transducer array makes up the aperture. The elevational aperture is the extent of the ultrasonic transducers in the elevational dimension. While some ultrasound imaging applications may benefit from collecting ultrasound data from the full aperture, some applications may benefit from collecting ultrasound data from only a portion of the elevational aperture (e.g., continuous portions of the elevational aperture), such as the centermost 50%, 25%, or any other suitable portion. For example, a smaller elevational aperture may be helpful when imaging in the near field where the outer elements are too far away or at too high of an angle off-center to add value to the image at shallow depths; when imaging through the ribs (e.g., in cardiac ultrasound imaging, and especially in pediatric cardiac ultrasound imaging); and/or when conserving power.

Recently, universal ultrasound devices have been developed, further description of which may be found in U.S. Pat. No. 10,856,840 titled "UNIVERSAL ULTRASOUND IMAGING DEVICE AND RELATED APPARATUS AND METHODS," issued on Dec. 8, 2020 (and assigned to the assignee of the instant application), which is incorporated by reference herein in its entirety. A universal ultrasound device may be configured to operate at multiple different medically-relevant frequency ranges and image patients at a sufficiently high resolution for forming medically-relevant images of different anatomical features or regions at a wide range of depths. As such, multiple conventional ultrasound probes may all be replaced by such a single universal ultrasound device, and medical professionals or other users may use a single universal ultrasound probe to perform multiple imaging tasks instead of using a multitude of conventional ultrasound probes each having limited applicability.

When using a universal ultrasound device, it may be desirable to perform imaging of one anatomical feature or region for which an elevational aperture of one size is appropriate, and then perform imaging of another anatomical feature or region for which an elevational aperture of a smaller size is appropriate. The inventors have realized that when using a smaller aperture, it may be desirable to more efficiently use the full processing capability of the ultrasound device to process the fewer number of ultrasound signals at a finer resolution than when using a larger aperture, without decreasing the frame rate. However, this may not be possible in certain conventional devices that lack sufficiently flexible circuitry. For example, in certain conventional ultrasound devices, the output terminal of each analog receive circuit may be switchably coupled to a single analog combination circuit. One option for reducing the aperture may be to simply decouple analog receive circuits processing signals from ultrasonic transducers not within the elevational aperture. However, this may not result in substantially finer resolution, as the same number of analog receive circuits may generally be coupled to each analog combination circuit. As another option, portions of the analog receive circuits processing signals from ultrasonic transducers within the elevational aperture may be multiplexed to analog combination circuits on different processing cycles. While this may result in finer resolution because fewer analog receive circuits are coupled to each analog combination circuit, this may also require more processing cycles to process signals from all the analog receive circuits within the elevational aperture, and therefore a lower frame rate. Another option may be to implement switches between each analog receive circuit and each analog combination circuit. While this may enable maximum flexibility, it may also include excessive routing and degradation of signal quality.

The inventors have developed new circuitry including switching circuitry and control circuitry to address this problem. Some embodiments of the switching circuitry described herein may constitute a middle ground between low flexibility topologies (e.g., in which each analog receive circuit is switchably coupled to just one analog combination circuit) and high flexibility topologies (e.g., in which each analog receive circuit is switchably coupled to each analog combination circuit). The switching circuitry may include multiple switches coupling the output terminals of certain analog receive circuit to the input terminals of multiple analog combination circuits. Different analog receive circuits may be switchably coupled to different numbers of analog combination circuits. Certain of the analog receive circuits may be switchably coupled to multiple but not all of the analog combination circuits. As a non-limiting example, if there are four analog combination circuits, the output terminal of one particular analog receive circuit may be switchably coupled to the input terminals of three analog combination circuits and the output terminal of another particular analog receive circuit may be switchably coupled to the input terminals of two analog combination circuits, while the output terminal of still another analog receive circuit may be switchably coupled to the input terminal of one analog combination circuit. In some embodiments, not every analog receive circuit is switchably coupled to each analog combination circuit. In some embodiments, fewer than 25% of the analog receive circuits are switchably coupled to each analog combination circuit. In some embodiments, fewer than 50% of the analog receive circuits are switchably coupled to each analog combination circuit. In some embodiments, fewer than 75% of the analog receive circuits are switchably coupled to each analog combination circuit. In some embodiments, none of the analog receive circuits are switchably coupled to each analog combination circuit. For a given analog receive circuit switchably coupled to multiple analog combination circuits, the control circuitry may select to which of these multiple analog combination circuits the analog receive circuit is coupled. The switching circuitry may enable sufficient flexibility for different, continuous elevational apertures to be used, with increased resolution for reduced sized apertures, and without decrease in frame rate.

The inventors have also developed technology in which a processing device in operative communication with an ultrasound device may generate a configuration indication based on a user selection of an anatomy for imaging, a user selection of an imaging depth, a power level of the ultrasound device, and/or a selected power mode for the ultrasound device, as specific non-limiting examples, and wherein the configuration indications are associated with different resolutions and/or elevational apertures. As described above, a smaller elevational aperture may be helpful for imaging in these situations. Thus, as one example, the control circuitry may control the switching circuitry to implement a first configuration having a larger elevational aperture and a coarser resolution based on receiving a configuration indication associated with imaging at a deeper depth, and then implement a second configuration having a smaller elevational aperture and a finer resolution based on receiving a configuration indication associated with imaging at a shallower depth, or vice versa. As another example, the control circuitry may control the switching circuitry to implement a first configuration having a larger elevational aperture and a coarser resolution based on receiving a configuration indication associated with imaging a particular anatomy (e.g., the abdomen), and then implement a second configuration having a smaller elevational aperture and a finer resolution based on receiving a configuration indication associated with imaging the heart, or vice versa. As another example, the control circuitry may control the switching circuitry to implement a first configuration having a larger elevational aperture and a coarser resolution based on receiving a configuration indication associated with the ultrasound device having a higher power level, and then implement a second configuration having a smaller elevational aperture and a finer resolution based on receiving a configuration indication associated with the ultrasound device having a lower power level, or vice versa. As another example, the control circuitry may control the switching circuitry to implement a first configuration having a larger elevational aperture and a coarser resolution based on receiving a configuration indication associated with a non-low power mode (e.g., a normal power mode) for the ultrasound device, and then implement a second configuration having a smaller elevational aperture and a finer resolution based on receiving a configuration indication associated with a low power mode, or vice versa.

Various aspects of the present disclosure may be used alone, in combination, or in a variety of arrangements not explicit in the foregoing embodiments and are therefore not limited in their application to the details and arrangement of components set forth in the foregoing description or illustrated in the drawings. For example, aspects described in one embodiment may be combined in any manner with aspects described in other embodiments.

Figure 1B:
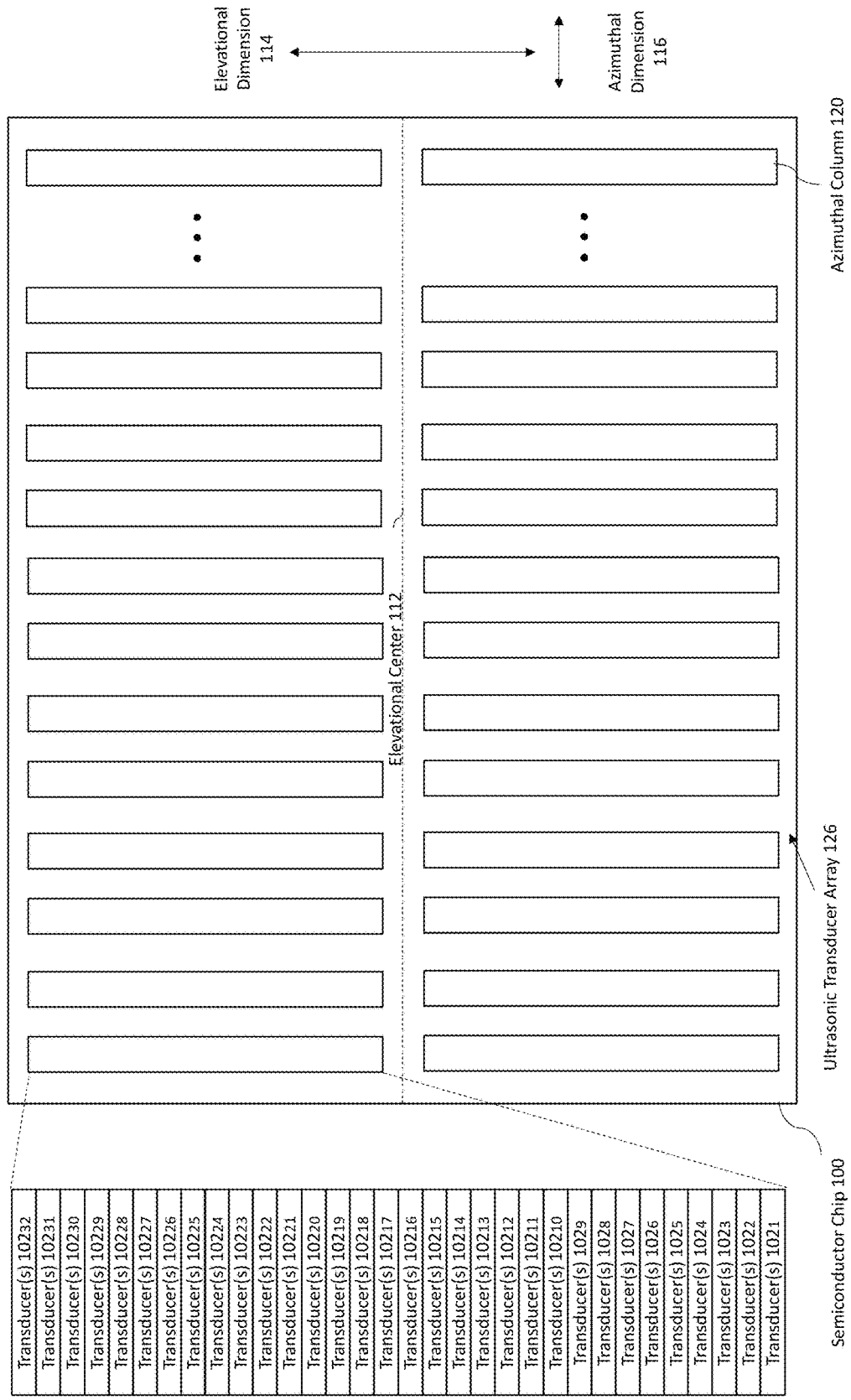

FIGS. 1A and 1B illustrate a schematic physical diagram of a semiconductor chip 100 having integrated thereon an ultrasonic transducer array 126 made up of ultrasonic transducers (e.g., capacitive micromachined ultrasonic transducers (CMUTs) or piezoelectric micromachined ultrasonic transducers (PMUTs)) 102 and ultrasound circuitry (not illustrated), in accordance with certain embodiments described herein. The ultrasonic transducer array 126 has an elevational dimension 114 and an azimuthal dimension 116. FIGS. 1A and 1B illustrate the elevational center 112 of the ultrasonic transducer array 126 (i.e., the center of the ultrasonic transducer array 126 along the elevational dimension 114). The ultrasonic transducers 102 are arranged along the elevational dimension 114 and the azimuthal dimension 116 of the ultrasonic transducer array 126. FIGS. 1A and 1B illustrate multiple azimuthal columns 120 of ultrasonic transducers 102 (i.e., columns of ultrasonic transducers 102 arranged along the azimuthal dimension 116 of the ultrasonic transducer array 126), where a portion of the azimuthal columns 120 are located above the elevational center 112 of the ultrasonic transducer array 126 and a portion of the azimuthal columns 120 of ultrasonic transducers 102 are located below the elevational center 112 of the ultrasonic transducer array 126. FIGS. 1A and 1B illustrate non-limiting illustrative example embodiments in which there are 32 ultrasonic transducers $102_1$-$102_{32}$ arranged along the elevational dimension 114 of the ultrasonic transducer array 126 in each azimuthal column 120.

In the nomenclature illustrated in FIGS. 1A and 1B, the ultrasonic transducer $102_1$ of each azimuthal column 120, whether above or below the elevational center 112 of the ultrasonic transducer array 126, is closest to the elevational center 112 and the ultrasonic transducer $102_{32}$ is farthest from the elevational center 112. The ultrasonic transducers $102_1$-$102_8$ of all the azimuthal columns 120 both above and below the elevational center 112 of the ultrasonic transducer array 126 may be considered the centermost 25% of the elevational aperture of the ultrasonic transducer array 126. The ultrasonic transducers $102_1$-$102_{16}$ of all the azimuthal columns 120 both above and below the elevational center 112 of the ultrasonic transducer array 126 may be considered the centermost 50% of the elevational aperture of the ultrasonic transducer array 126. Further illustration of these portions of the elevational aperture of the ultrasonic transducer array 126 may be found with reference to FIGS. 2-3.

FIG. 2 illustrates the centermost 25% of the elevational aperture of the ultrasonic transducer array 126, in accordance with certain embodiments described herein. The centermost 25% of the elevational aperture of the ultrasonic transducer array 126 is shaded in black and labeled 224. The elevational aperture 224 may be considered continuous.

Figure 3A:
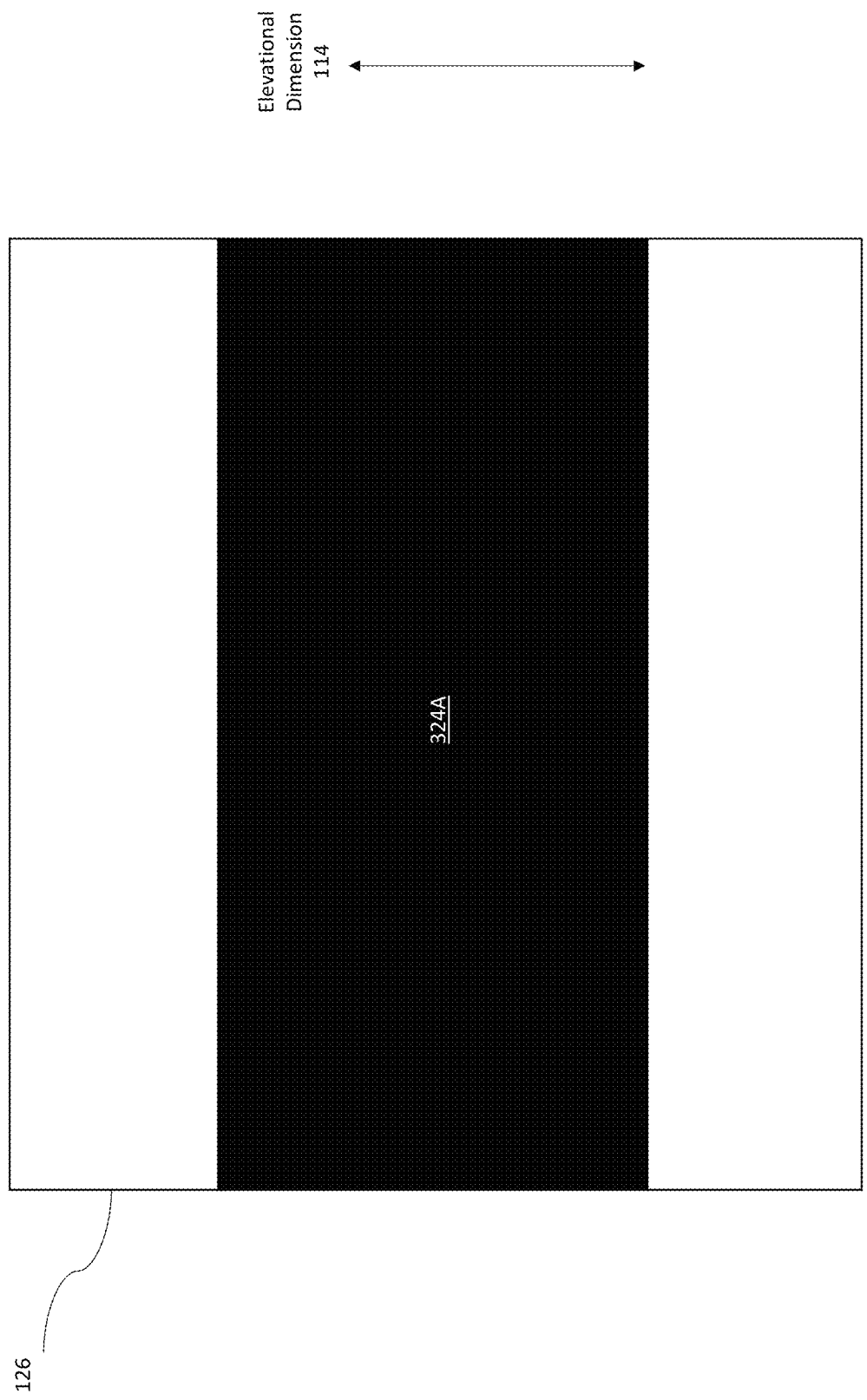
FIG. 3A illustrates the centermost 50% of the elevational aperture of the ultrasonic transducer array of FIGS. 1A and 1B, in accordance with certain embodiments described herein.

FIG. 3A illustrates the centermost 50% of the elevational aperture of the ultrasonic transducer array 126, in accordance with certain embodiments described herein. The centermost 50% of the elevational aperture of the ultrasonic transducer array 126 is shaded in black and labeled 324A. The elevational aperture 324A may be considered continuous.

FIG. 3B illustrates the full elevational aperture of the ultrasonic transducer array 126, in accordance with certain embodiments described herein. 100% of the elevational aperture of the ultrasonic transducer array 126 is shaded in black and labeled 324B. The elevational aperture 324B may be considered continuous.

Figure 13:
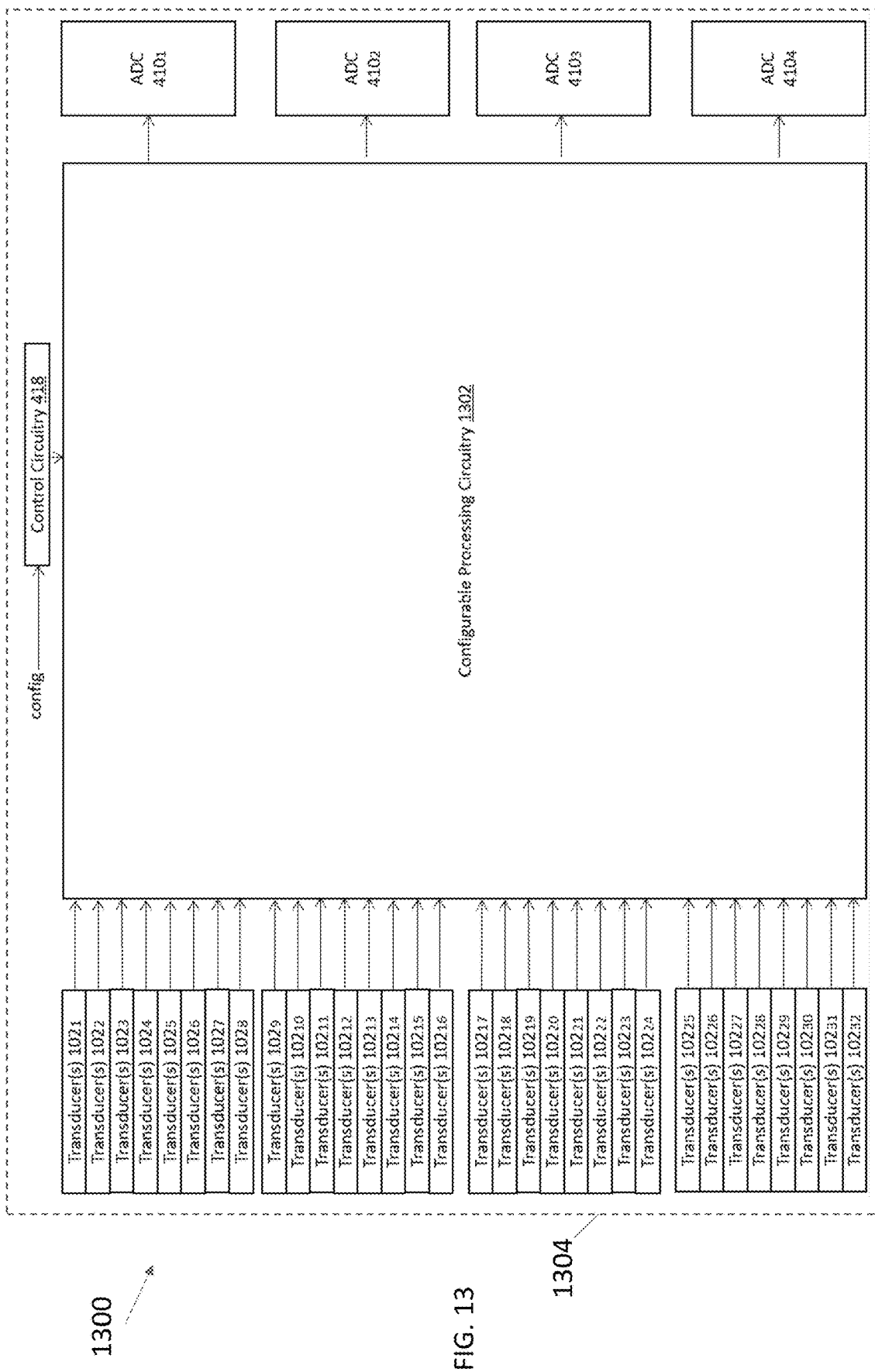
FIG. 13 illustrates a schematic block diagram of ultrasound circuitry, in accordance with certain embodiments described herein.

According to an aspect of the present application, an ultrasound device is provided, comprising an ultrasonic transducer array, configurable processing circuitry coupled to the ultrasonic transducer array, and control circuitry coupled to the configurable processing circuitry and configured to set the configurable processing circuitry to a first configuration exhibiting a first elevational aperture percentage and first resolution and then to a second configuration exhibiting a second elevational aperture percentage different than the first elevational aperture percentage and a second resolution different than the first resolution. FIG. 13 illustrates a non-limiting example.

FIG. 13 illustrates a schematic block diagram of ultrasound circuitry, in accordance with certain embodiments described herein. In this example, FIG. 13 illustrates ultrasound circuitry coupled to the ultrasonic transducers 102 in a single azimuthal column 120. In some embodiments, the ultrasound circuitry illustrated in FIG. 13 may be coupled to the ultrasonic transducers 102 in multiple azimuthal columns 120. Returning to FIG. 13, the ultrasound device 1300 comprises ultrasonic transducers $102_1$-$102_{32}$, configurable processing circuitry 1302, analog-to-digital converters (ADCs) $410_1$-$410_4$, and control circuitry 418. The configurable processing circuitry 1302 is coupled to the ultrasonic transducers $102_1$-$102_{32}$. The control circuitry 418 is configured to set the configurable processing circuitry to different configurations exhibiting different elevational aperture percentages with associated resolutions. For example, the control circuitry may configure the configurable processing circuitry to exhibit a first elevational aperture percentage (e.g., 25% as in FIG. 2) at a first resolution. Subsequently, the control circuitry may configure the configurable processing circuitry to exhibit a second elevational aperture percentage (e.g., 50% as in FIG. 3A) at a second resolution different than the first resolution. Thus, the elevational aperture percentage and resolution may be adjusted by suitably controlling the configurable processing circuitry.

In some embodiments, the ultrasound device includes a housing, as shown in FIG. 13. In that example, the illustrated circuitry is disposed in housing 1304. The housing may take any suitable shape, such as being an ultrasound probe, ultrasound patch, pill, or any other suitable housing. Thus, it should be appreciated that according to an aspect of the present application, an ultrasound device is provided comprising: a housing; an ultrasonic transducer array disposed within the housing; and configurable processing circuitry disposed within the housing and coupled to the ultrasonic transducer array, configured to process output signals of the ultrasonic transducer array, and configurable in a first configuration exhibiting a first elevational aperture percentage and first resolution and a second configuration exhibiting a second elevational aperture percentage different than the first elevational aperture percentage and a second resolution different than the first resolution.

Figure 4:
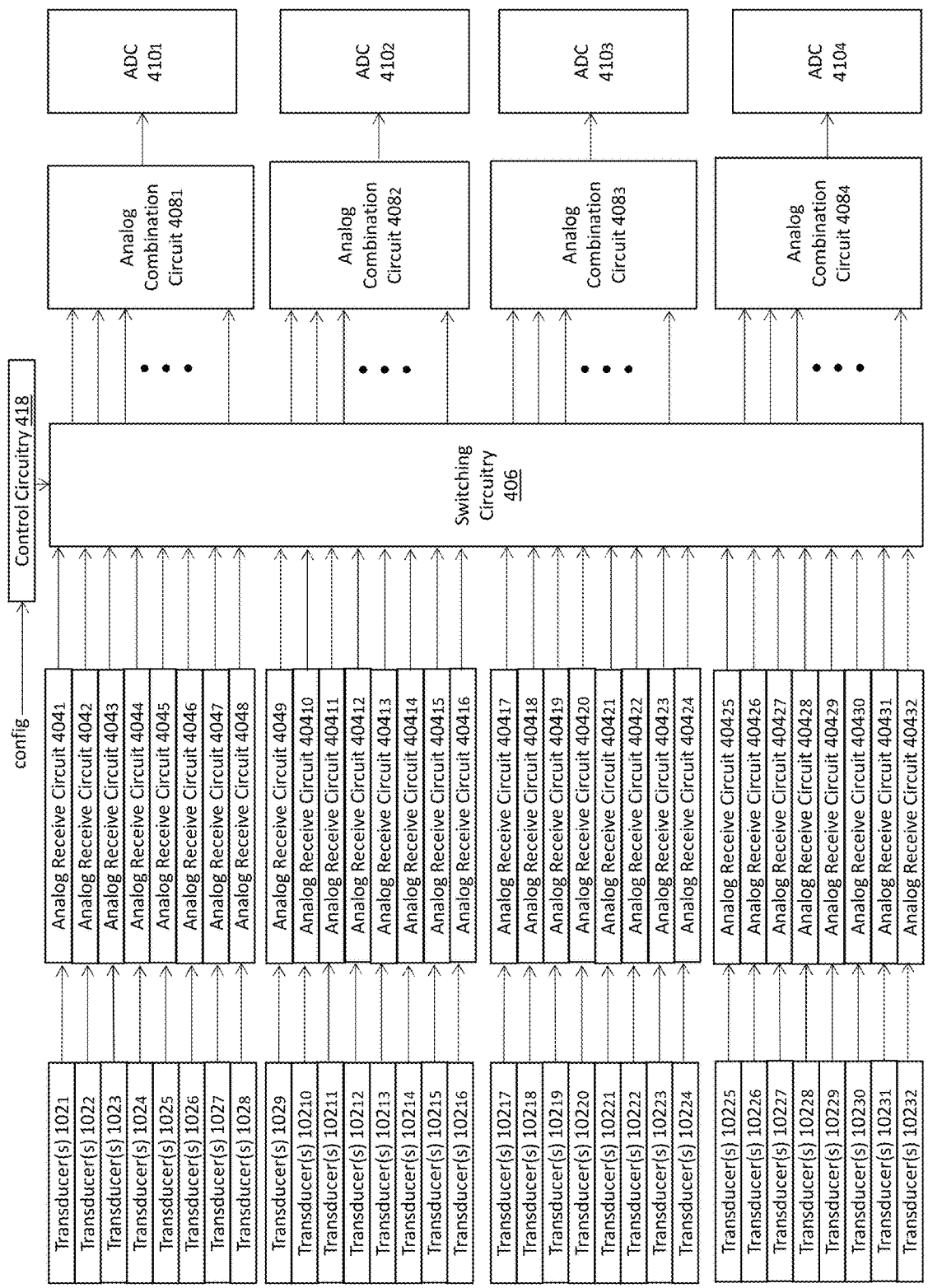
FIG. 4 illustrates a schematic block diagram of ultrasound circuitry, in accordance with certain embodiments described herein.

FIG. 4 illustrates a schematic block diagram of ultrasound circuitry, in accordance with certain embodiments described herein. FIG. 4 includes a non-limiting detailed implementation of the configurable processing circuitry 1302. The ultrasound circuitry illustrated in FIG. 4 may be implemented in the semiconductor chip 100 (or, in some embodiments, in multiple semiconductor chips). In particular, FIG. 4 illustrates ultrasound circuitry coupled to the ultrasonic transducers 102 in a single azimuthal column 120. The ultrasound circuitry includes analog receive circuits $404_1$-$404_{32}$, switching circuitry 406, analog combination circuits $408_1$-$408_4$, analog-to-digital converters (ADCs) $410_1$-$410_4$, and control circuitry 418. The analog receive circuits, switching circuitry, and analog combination circuitry represent a non-limiting example of the configurable processing circuitry of FIG. 13. The analog receive circuits $404_1$-$404_{32}$ are coupled between the output terminals of the ultrasonic transducers $102_1$-$102_{32}$ (where each of one or more ultrasonic transducers 102 may include multiple ultrasonic transducers coupled together) and the input terminals of the switching circuitry 406. The switching circuitry 406 is coupled between the output terminals of the analog receive circuits $404_1$-$404_{32}$ and the input terminals of the analog combination circuits $408_1$-$408_4$. The analog combination circuits $408_1$-$408_4$ are coupled between the output terminals of the switching circuitry 406 and the input terminals of the analog-to-digital converters $410_1$-$410_4$. Thus, the output terminal of two or more, and in some embodiments each, of the ultrasonic transducers $102_1$-$102_{32}$ may be coupled (either directly or through intervening circuitry not illustrated) to the input terminal of a respective analog receive circuit $404_1$-$404_{32}$. The output terminal of two or more, and in some embodiments each, of the analog receive circuits $404_1$-$404_{32}$ may be coupled to an input terminal of the switching circuitry 406 (either directly or through intervening circuitry not illustrated). Each of two or more of the output terminals of the switching circuitry 406 may be switchably coupled to an input terminal of a particular one of the analog combination circuits $408_1$-$408_4$ (either directly or through intervening circuitry not illustrated). The output terminal of each of two or more of the analog combination circuits $408_1$-$408_4$ may be coupled to the input terminal of a respective analog-to-digital converter $410_1$-$410_4$ (either directly or through intervening circuitry not illustrated). The output of the control circuitry 418 may be coupled to the switching circuitry 406 (although the control circuitry 418 may control other circuitry illustrated in FIG. 4 or not, and thus may be coupled to circuitry through couplings not illustrated).

An analog receive circuit 404, and in some embodiments each analog receive circuit 404, may be configured to receive and/or process an analog ultrasound signal from a corresponding ultrasonic transducer 102 (or, generally, from one or more corresponding ultrasonic transducers 102 that are coupled together). Each analog receive circuit 404 may include, for example, analog amplification circuitry (e.g., one or more transimpedance amplifiers), analog filtering circuitry, analog polarity conversion circuitry, analog compression circuitry, analog expansion circuitry, analog beamforming circuitry, analog dechirp circuitry, analog quadrature demodulation (AQDM) circuitry, analog time delay circuitry, analog phase shifter circuitry and/or analog time gain compensation circuitry.

Figure 5:
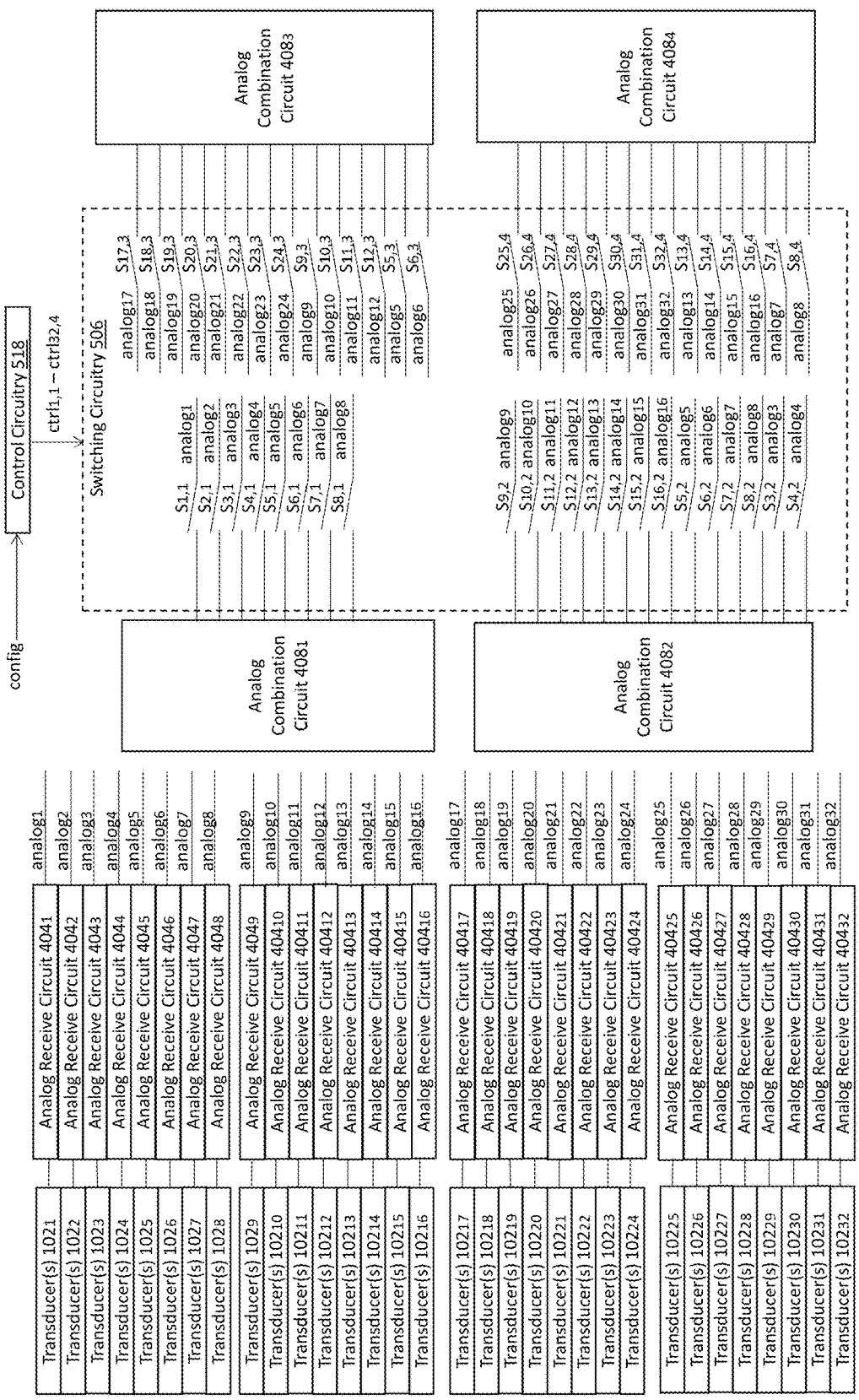
FIG. 5 illustrates a schematic block diagram of ultrasound circuitry, in accordance with certain embodiments described herein.
Figure 6:
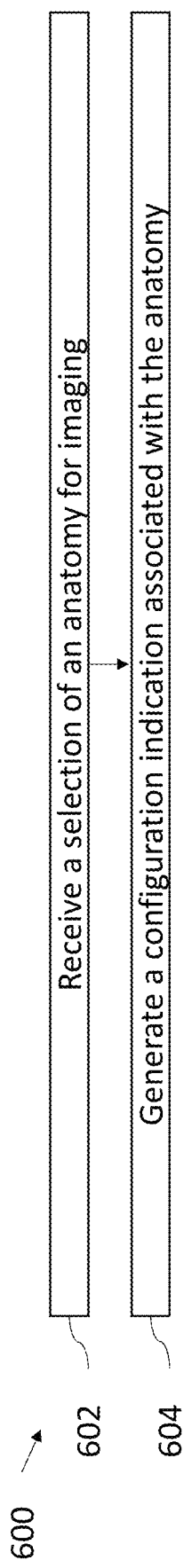
FIGS. 6, 7, 8A and 8B illustrate flow diagrams of processes for generating configuration indications for configuring an ultrasound device, in accordance with certain embodiments described herein.
Figure 7:
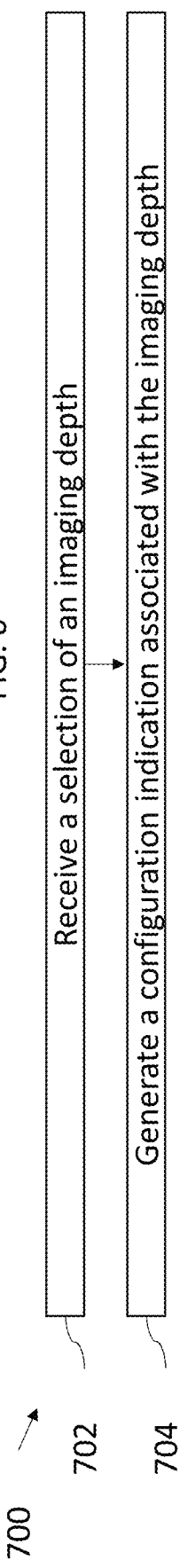
Figure 8A:
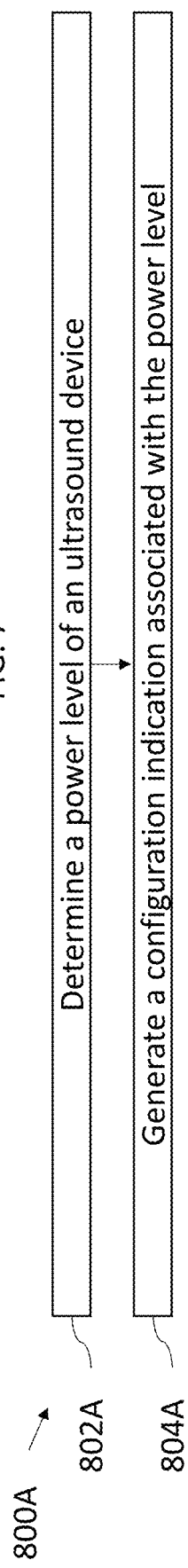
Figure 8B:
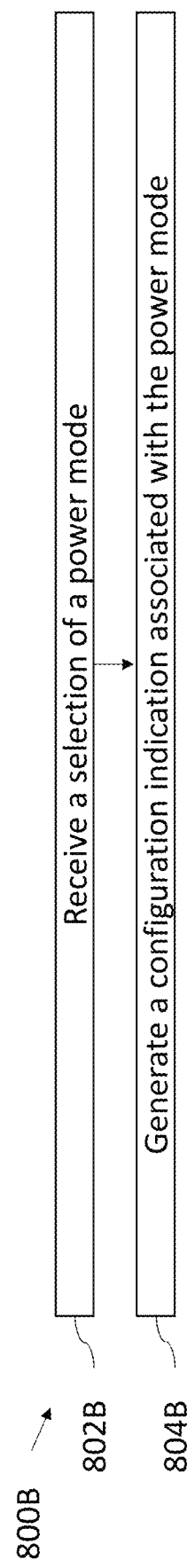

The switching circuitry 406 may include multiple switches switchably coupling output terminals of certain analog receive circuits 404 to input terminals of certain analog combination circuits 408. One example is illustrated in FIG. 5. The control circuitry 418 may be configured to control the switching circuitry 406 to cause particular output terminals of the analog receive circuits 404 to be coupled through the switches of the switching circuitry 406 to input terminals of particular analog combination circuits 408. Further description of various configurations may be found with reference to FIG. 5.

Each of two or more of the analog combination circuits $408_1$-$408_4$ may be configured to output a single analog output signal by combining multiple analog input signals. In some embodiments, the analog combination circuits $408_1$-$408_4$ may include analog averaging circuitry. In some embodiments, the analog combination circuits $408_1$-$408_4$ may include one or more resistors configured to passively sum multiple inputs. The ADCs $410_1$-$410_4$ may be configured to convert each output signal of an analog combination circuit 408 from analog to digital. Alternatively, in some embodiments, multiple analog combination circuits $408_1$-$408_4$ may be multiplexed to a single ADC 410. There may be further downstream processing circuitry not illustrated, such as digital filtering circuitry, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, backend processing circuitry and/or one or more output buffers. The image formation may be configured to perform apodization, back projection and/or fast hierarchy back projection, interpolation range migration (e.g., Stolt interpolation) or other Fourier resampling techniques, dynamic focusing techniques, delay and sum techniques, tomographic reconstruction techniques, Doppler calculation, frequency and spatial compounding, and/or low and high-pass filtering, etc.

FIG. 5 illustrates a schematic block diagram of ultrasound circuitry, in accordance with certain embodiments described herein. The ultrasound circuitry illustrated in FIG. 5 may be implemented in the semiconductor chip 100. The ultrasound circuitry illustrated in FIG. 5 is the same as in FIG. 4, except that FIG. 5 illustrates switching circuitry 506 and control circuitry 518, and no ADCs are illustrated even though they may be included and coupled to the analog combination circuitry in the same manner as shown in FIG. 4. The switching circuitry 506 may be an example implementation of the switching circuitry 406 and the control circuitry 518 may be an example implementation of the control circuitry 418, although it should be understood that alternative implementations of switching circuitry 406 and control circuitry 418 are possible. FIG. 5 further labels each output terminal of the analog receive circuits $404_1$-$404_{32}$ as $analog_1$-$analog_{32}$, respectively.

The switching circuitry 506 includes sets of switches labeled $S_{1,1}$-$S_{32,4}$. In this non-limiting example, each of the switches in the switching circuitry 506 switchably couples one of the outputs $analog_1$-$analog_{32}$ to an input of one of the analog combination circuits $408_1$-$408_4$. In the notation used for the switches $S_{1,1}$-$S_{32,4}$, the first subscripted number corresponds to the subscript of the analog receive circuit to which the switch is coupled on one end, and the second subscripted number corresponds to the subscript of the analog combination circuit to which the switch is coupled on the other end. The control circuitry 518 outputs control signals $ctrl_{1,1}$-$ctrl_{32,4}$ to each switch $S_{1,1}$-$S_{32,4}$, respectively. The control circuitry 518 may use the control signals $ctrl_{1,1}$-$ctrl_{32,4}$ to open or close certain of the switches $S_{1,1}$-$S_{32,4}$ in order to couple particular output terminals of the analog receive circuits $404_1$-$404_{32}$ to particular analog combination circuits $408_1$-$408_4$. It should be appreciated that the elevational aperture used may depend, at least in part, on which output signals of analog receive circuits 404 are coupled, through the switching circuitry 506, to analog combination circuitry 408 and downstream circuitry, and which are not. Additionally, it should be appreciated that the resolution at which analog ultrasound signals are processed by the ultrasound circuitry illustrated in FIG. 5 may depend, at least in part, on how many output signals of analog receive circuits 404 are coupled to each analog combination circuit 408. Finer resolution may correspond to fewer analog ultrasound signals combined together and coarser resolution may correspond to more analog ultrasound signals combined together. Thus, more output signals of analog receive circuits 404 coupled to a given, and in some embodiments each, analog combination circuit 408 may correspond to coarser resolution and fewer output signals of analog receive circuits 404 coupled to a given, and in some embodiments each, analog combination circuit 408 may correspond to finer resolution. Thus, the control circuitry 518 may control the switching circuitry 506 to implement various configurations of resolution and elevational aperture.

For example, in one configuration, the control circuitry 518 may cause the switches $S_{1,1}$-$S_{8,1}$, $S_{9,2}$-$S_{16,2}$, $S_{17,3}$-$S_{24,3}$, and $S_{25,4}$-$S_{32,4}$ to be closed and the others to be open. Thus, the eight output terminals $analog_1$-$analog_8$ may be coupled to the analog combination circuit $408_1$, the eight output terminals $analog_9$-$analog_{16}$ may be coupled to the analog combination circuit $408_2$, the eight output terminals $analog_{17}$-$analog_{24}$ may be coupled to the analog combination circuit $408_3$, and the eight output terminals $analog_{25}$-$analog_{32}$ may be coupled to the analog combination circuit $408_4$. This may be referred to as an "8×1" configuration because 8 (8×) analog receive circuits 404 of one (×1) azimuthal column are coupled to each analog combination circuit 408. It should be appreciated that when all azimuthal columns 120 in the ultrasonic transducer array 126 are configured in the 8×1 configuration, then data from all the ultrasonic transducers 102 in the ultrasonic transducer array 126 may be processed. It should be appreciated that all the ultrasonic transducers 102 in the ultrasonic transducer array 126 being processed may constitute use of the elevational aperture 324B.

The above description of the 8×1 configuration assumes that all 32 output terminals $analog_1$-$analog_{32}$ are coupled to analog combination circuits 408. Variants of the 8×1 combination may include decoupling from analog combination circuits 408 certain of the output terminals $analog_1$-$analog_{32}$ that are coupled to analog combination circuits 408 in the 8×1 configuration. For example, to implement an example variant of the 8×1 configuration that includes coupling the 17 output terminals $analog_1$-$analog_{17}$ to analog combination circuits 408, the control circuitry 518 may cause the switches $S_{1,1}$-$S_{8,1}$, $S_{9,2}$-$S_{16,2}$, and $S_{17,3}$ to be closed and the others to be open. Thus, the eight output terminals $analog_1$-$analog_8$ may be coupled to the analog combination circuit $408_1$, the eight output terminals $analog_9$-$analog_{16}$ may be coupled to the analog combination circuit $408_2$, and the output terminal $analog_{17}$ may be coupled to the analog combination circuit $408_3$. The output terminals $analog_{18}$-$analog_{32}$ are not coupled to an analog combination circuit 408. In other words, the output terminals $analog_{18}$-$analog_{32}$ from the analog receive circuits $404_{18}$-$404_{32}$ (which are, in turn, processing signals outputted by the ultrasonic transducers $102_{18}$-$102_{32}$) may not be processed in this configuration. Additionally, no output terminals from analog receive circuits 404 are coupled to the analog combination circuit $408_4$. While this example variant includes coupling 17 output terminals $analog_1$-$analog_{17}$ to analog combination circuits 408, any number of output terminals from 1-32 may be coupled to analog combination circuits 408.

In another configuration, the control circuitry 518 may cause the switches $S_{1,1}$-$S_{4,1}$, $S_{5,2}$-$S_{8,2}$, $S_{9,3}$-$S_{12,3}$, and $S_{13,4}$-$S_{16,4}$ to be closed and the others to be open. Thus, the four output terminals $analog_1$-$analog_4$ may be coupled to the analog combination circuit $408_1$, the four output terminals $analog_5$-$analog_8$ may be coupled to the analog combination circuit $408_2$, the four output terminals $analog_9$-$analog_{12}$ may be coupled to the analog combination circuit $408_3$, and the four output terminals $analog_{13}$-$analog_{16}$ may be coupled to the analog combination circuit $408_4$. The output terminals $analog_{17}$-$analog_{32}$ may not be coupled to any of the analog combination circuits $408_1$-$408_4$. In other words, the output terminals $analog_{17}$-$analog_{32}$ of the analog receive circuits $404_{17}$-$404_{32}$ (which are, in turn, processing signals outputted by the ultrasonic transducers $102_{17}$-$102_{32}$) may not be processed in this configuration. This may be referred to as a "4×1" configuration because 4 (4×) analog receive circuits 404 of one (×1) azimuthal column are coupled to each analog combination circuit 408. It should be appreciated that when all azimuthal columns 120 in the ultrasonic transducer array 126 are configured in the 4×1 configuration, then only data from the centermost 50% of the elevational aperture in the ultrasonic transducer array 126 (namely, the ultrasonic transducers $102_1$-$102_{16}$ in each azimuthal column 120) may be processed. In other words, half of the elevational aperture of the ultrasonic transducer array 126 (compared with the full elevational aperture in the 8×1 configuration) may be used. It should be appreciated that the ultrasonic transducers $102_1$-$102_{16}$ in each azimuthal column 120 of the ultrasonic transducer array 126 being processed may constitute use of the elevational aperture 324A. On the other hand, because the output terminals of 4 analog receive circuits are coupled to each analog combination circuit 408 (compared with 8 in the 8×1 configuration), the resolution in the 4×1 configuration may be twice as fine as in the 8×1 configuration. It should be appreciated that, in the 4×1 configuration, all the ultrasonic transducers 102 in the elevational aperture 324A may be coupled to analog combination circuits 408 at one time, and thus processing data from all the ultrasonic transducers 102 in the elevational aperture 324A may not require multiplexing in time. Therefore, the increased resolution in the 4×1 configuration may be achieved without reduction in frame rate compared with the 8×1 configuration.

The above description of the 4×1 configuration assumes that all 16 output terminals $analog_1$-$analog_{16}$ are coupled to analog combination circuits 408. Variants of the 4×1 combination may include decoupling from analog combination circuits 408 certain of the output terminals $analog_1$-$analog_{16}$ that are coupled to analog combination circuits 408 in the 4×1 configuration. For example, to implement an example variant of the 4×1 configuration that includes coupling 9 output terminals $analog_1$-$analog_9$ to analog combination circuits 408, the control circuitry 518 may cause the switches $S_{1,1}$-$S_{4,1}$, $S_{5,2}$-$S_{8,2}$, and $S_{9,3}$ to be closed and the others to be open. Thus, the four output terminals $analog_1$-$analog_4$ may be coupled to the analog combination circuit $408_1$, the four output terminals $analog_1$-$analog_8$ may be coupled to the analog combination circuit $408_2$, and the output terminal $analog_9$ may be coupled to the analog combination circuit $408_3$. The output terminals $analog_{10}$-$analog_{32}$ are not coupled to an analog combination circuit 408. In other words, the output terminals $analog_{10}$-$analog_{32}$ of the analog receive circuits $404_{10}$-$404_{32}$ (which are, in turn, processing signals outputted by the ultrasonic transducers $102_{10}$-$102_{32}$) may not be processed in this configuration. Additionally, no output terminals from analog receive circuits 404 are coupled to the analog combination circuit $408_4$. While this example variant includes coupling 9 output terminals $analog_1$-$analog_9$ to analog combination circuits 408, any number of output terminals from 1-16 may be coupled to analog combination circuits 408.

In another configuration, the control circuitry 518 may cause the switches $S_{1,1}$-$S_{2,1}$, $S_{3,2}$-$S_{4,2}$, $S_{5,3}$-$S_{6,3}$, and $S_{7,4}$-$S_{8,4}$ to be closed and the others to be open. Thus, the two output terminals $analog_3$ and $analog_2$ may be coupled to the analog combination circuit $408_1$, the two output terminals $analog_3$ and $analog_4$ may be coupled to the analog combination circuit $408_2$, the two output terminals $analog_5$ and $analog_6$ may be coupled to the analog combination circuit $408_3$, and the two output terminals $analog_7$ and $analog_8$ may be coupled to the analog combination circuit $408_4$. The output terminals $analog_9$-$analog_{32}$ may not be coupled to any of the analog combination circuits $408_1$-$408_4$. In other words, the output terminals of the analog receive circuits $404_9$-$404_{32}$ (which are, in turn, processing signals outputted by the ultrasonic transducers $102_9$-$102_{32}$) may not be processed in this configuration. This may be referred to as an "2×1" configuration because 2 (2×) analog receive circuits 404 of one (×1) azimuthal column are coupled to each analog combination circuit 408. It should be appreciated that when all azimuthal columns 120 in the ultrasonic transducer array 126 are configured in the 2×1 configuration, then only data from the centermost 25% of the elevational aperture of the ultrasonic transducer array 126 (namely, the ultrasonic transducers $102_1$-$102_8$ in each azimuthal column 120) may be processed. In other words, a quarter of the elevational aperture of the ultrasonic transducer array 126 (compared with the full elevational aperture in the 8×1 configuration and half the elevational aperture in the 4×1 configuration) may be used. It should be appreciated that the ultrasonic transducers $102_1$-$102_8$ in each azimuthal column 120 of the ultrasonic transducer array 126 being processed may constitute use of the elevational aperture 224. On the other hand, because the output terminals of 2 analog receive circuits are coupled to each analog combination circuit 408 (compared with 8 in the 8×1 configuration and 4 in the 4×1 configuration), the resolution in the 2×1 configuration may be twice as fine as in the 4×1 configuration and four times as fine as in the 8×1 configuration. It should be appreciated that, in the 2×1 configuration, all the ultrasonic transducers 102 in the elevational aperture 224 may be coupled to analog combination circuits 408 at one time, and thus processing data from all the ultrasonic transducers 102 in the elevational aperture 224 may not require multiplexing in time. Therefore, the increased resolution in the 2×1 configuration may be achieved without reduction in frame rate compared with the 8×1 or 4×1 configurations.

The above description of the 2×1 configuration assumes that all 8 output terminals $analog_1$-$analog_8$ are coupled to analog combination circuits 408. To implement an example variant of the 2×1 configuration that includes coupling the 5 output terminals analog$_1$-analog$_8$ to analog combination circuits 408, the control circuitry 518 may cause the switches $S_{1,1}$-$S_{2,1}$, $S_{3,2}$-$S_{4,2}$, and $S_{5,3}$ to be closed and the others to be open. Thus, the two output terminals analog$_1$ and analog$_2$ may be coupled to the analog combination circuit 408$_1$, the two output terminals analog$_3$ and analog$_4$ may be coupled to the analog combination circuit 408$_2$, and the output terminal analog$_5$ may be coupled to the analog combination circuit 408$_3$. The output terminals analog$_6$-analog$_{32}$ are not coupled to an analog combination circuit 408. In other words, the output terminals analog$_6$-analog$_{32}$ of the analog receive circuits 404$_6$-404$_{32}$ (which are, in turn, processing signals outputted by the ultrasonic transducers 102$_6$-102$_{32}$) may not be processed in this configuration. Additionally, no output terminals from analog receive circuits 404 are coupled to the analog combination circuit 408$_4$. While this example variant includes coupling 5 of the output terminals 404$_1$-404$_5$ to analog combination circuits 408, any number of output terminals from 1-8 may be coupled to analog combination circuits 408.

The control circuitry 518 may be configured to control the switching circuitry 506 to implement any, and in some embodiments each, of these configurations, and which configuration the control circuitry 518 controls the switching circuitry 506 to implement may be based on a control parameter received by the control circuitry 518, and labeled as "config" in FIG. 5. The control circuitry 518 may be configured to control the switching circuitry 506 to implement one configuration and then implement another configuration when the received control parameter changes. Generally, the control circuitry may be configured to control the switching circuitry 506 to implement one configuration and then implement another configuration having a larger elevational aperture but coarser resolution. Additionally, the control circuitry may be configured to control the switching circuitry 506 to implement one configuration and then implement another configuration having a smaller elevational aperture but finer resolution. For example, the control circuitry 518 may control the switching circuitry 506 to do any or all of the following: implement the 8×1 configuration and then the 4×1 configuration (smaller elevational aperture and finer resolution), to implement the 8×1 configuration and then the 2×1 configuration (smaller elevational aperture and finer resolution), to implement the 4×1 configuration and then the 2×1 configuration (smaller elevational aperture and finer resolution), to implement the 4×1 configuration and then the 8×1 configuration (larger elevational aperture and coarser resolution), to implement the 2×1 configuration and then the 4×1 configuration (larger elevational aperture and coarser resolution), and to implement the 2×1 configuration and then the 8×1 configuration (larger elevational aperture and coarser resolution).

In embodiments in which each of the switches $S_{1,1}$-$S_{32,4}$ is an N-type metal-oxide-semiconductor (nMOS) transistor, the control circuitry 518 may cause the control signals ctrl$_{1,1}$-ctrl$_{32,4}$ to be a digital high voltage to close the corresponding switches and a digital low voltage to open the corresponding switches. In embodiments in which each of the switches $S_{1,1}$-$S_{32,4}$ is a P-type metal-oxide-semiconductor (pMOS) transistor, the control circuitry 518 may cause the control signals ctrl$_{1,1}$-ctrl$_{32,4}$ to be a digital low voltage to close the corresponding switches and a digital high voltage to open the corresponding switches. In some embodiments, one or more, and in some embodiments each, of the control signals ctrl$_{1,1}$-ctrl$_{32,4}$ may include multiple individual control signals. For example, in embodiments in which each of the switches $S_{1,1}$-$S_{32,4}$ is a transmission gate having nMOS transistor and a pMOS transistor, to close a given switch, the control circuitry 518 may output a control signal including a digital high voltage applied to the gate of the nMOS transistor and a digital low voltage applied to the gate of the pMOS transistor. To open a given switch, the control circuitry 518 may output a control signal including a digital low voltage applied to the gate of the nMOS transistor and a digital high voltage applied to the gate of the pMOS transistor. It should be appreciated that other types of switches may be used and different types of switches may use different types of control signals. The control circuitry 518 may be configured to receive a configuration parameter config associated with a particular configuration (e.g., associated with the 2×1, 4×1, or 8×1 configuration) based on which the control circuitry 518 may output control signals ctrl$_{1,1}$-ctrl$_{32,4}$ particular to that configuration. As described above, the specific configuration parameter config received by the control circuitry 518 may be generated based on the imaging depth selection, the anatomy selected for imaging, the power level of the ultrasound device, and/or a power mode selection. Further description of generation of the configuration parameter config will be described with reference to FIGS. 6-8B.

Generally, variants of the configurations described may be implemented by coupling particular outputs analog$_1$-analog$_{32}$ to particular analog combination circuits 408$_1$-408$_4$ by closing or opening the appropriate switches $S_{1,1}$-$S_{32,4}$ using the corresponding control signals ctrl$_{1,1}$-ctrl$_{32,4}$.

It should be appreciated that the output terminals of certain analog receive circuits 404 are switchably coupled, through the switching circuitry 506, to input terminals of multiple analog combination circuits 408. Additionally, the output terminals of certain analog receive circuits 404 are switchably coupled, through the switching circuitry, to input terminals of multiple but not all of the analog combination circuits 408$_1$-408$_4$. For example, analog$_8$ is switchably coupled to the analog combination circuit 408$_1$ through the switch $S_{8,1}$, to the analog combination circuit 408$_2$ through the switch $S_{8,2}$, to the analog combination circuit 408$_4$ through the switch $S_{8,4}$, but not to the analog combination circuit 408$_3$. It should also be appreciated from the above description that, when configuring the ultrasound device in one configuration and then in another configuration, the control circuitry 518 may cause a particular output terminal of an analog receive circuit 404 to be coupled to one of the analog combination circuits 408 in the first configuration and then to be coupled to a different one of the analog combination circuits 408 in the second configuration. As one non-limiting example, as described above, in the 8×1 configuration, analog$_8$ may be coupled to the analog combination circuit 408$_1$, in the 4×1 configuration analog$_8$ may be coupled to the analog combination circuit 408$_2$, and in the 2×1 configuration analog$_8$ may be coupled to the analog combination circuit 408$_4$.

It should also be appreciated that certain output terminals of the analog receive circuits 404 are switchably coupled to different number of analog combination circuits 408. For example, analog$_1$ is switchably coupled just to the analog combination circuit 408$_1$ while analog$_8$ is switchably coupled to the analog combination circuits 408$_1$, 408$_2$, and 408$_4$. It should also be appreciated that in the switching circuitry 506, none of the output terminals analog$_1$-analog$_{32}$ are switchably coupled to input terminals of each analog combination circuit 408$_1$-408$_4$. In some other embodiments, some but fewer than 25%, 50%, or 75% of the analog receive circuits 404 are switchably coupled to each analog combination circuit $408_1$-$408_4$.

The switching circuitry 506 is an example of a topology that has been specifically designed to have sufficient flexibility for different, continuous elevational apertures (e.g., the elevational apertures 224, 324A, and 324B) to be used, with increased resolution for reduced sized apertures, and without decrease in frame rate. The specific design may include the choices of which of the output terminals of the analog receive circuits 404 are switchably coupled to which of the analog combination circuits 408, such as the choice to couple $analog_1$ only to the analog combination circuit $408_1$ but to couple $analog_8$ to the analog combination circuits $408_1$, $408_2$, and $408_4$. Additionally, the switching circuitry 506 is an example of a topology in which at least some analog receive circuits 404 are not coupled to all the analog combination circuits $408_1$-$408_4$, and may therefore avoid excessive routing and degradation of signal quality.

Figure 14:
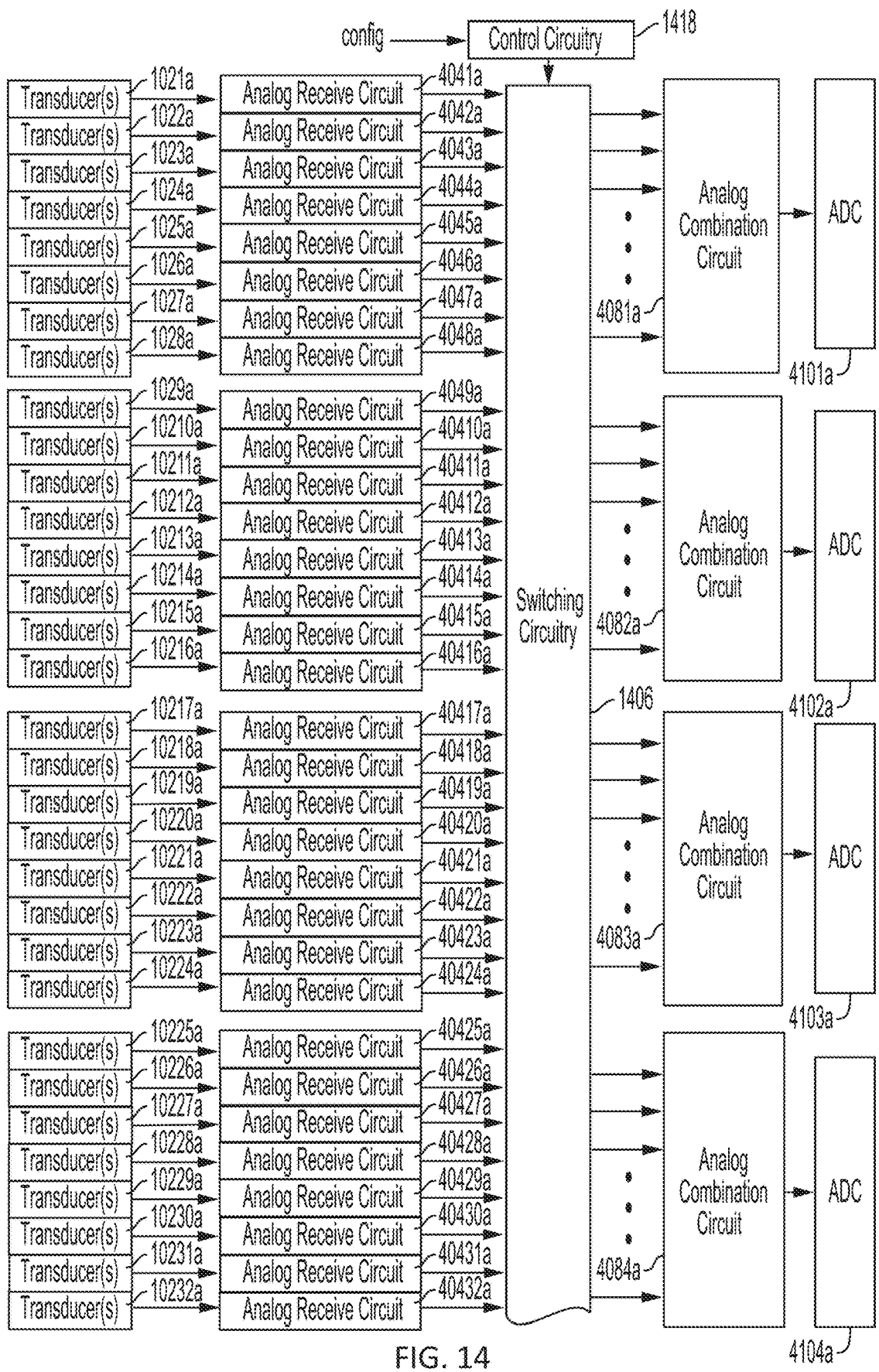
FIG. 14 illustrates a schematic block diagram of ultrasound circuitry, in accordance with certain embodiments described herein.
Figure 14:
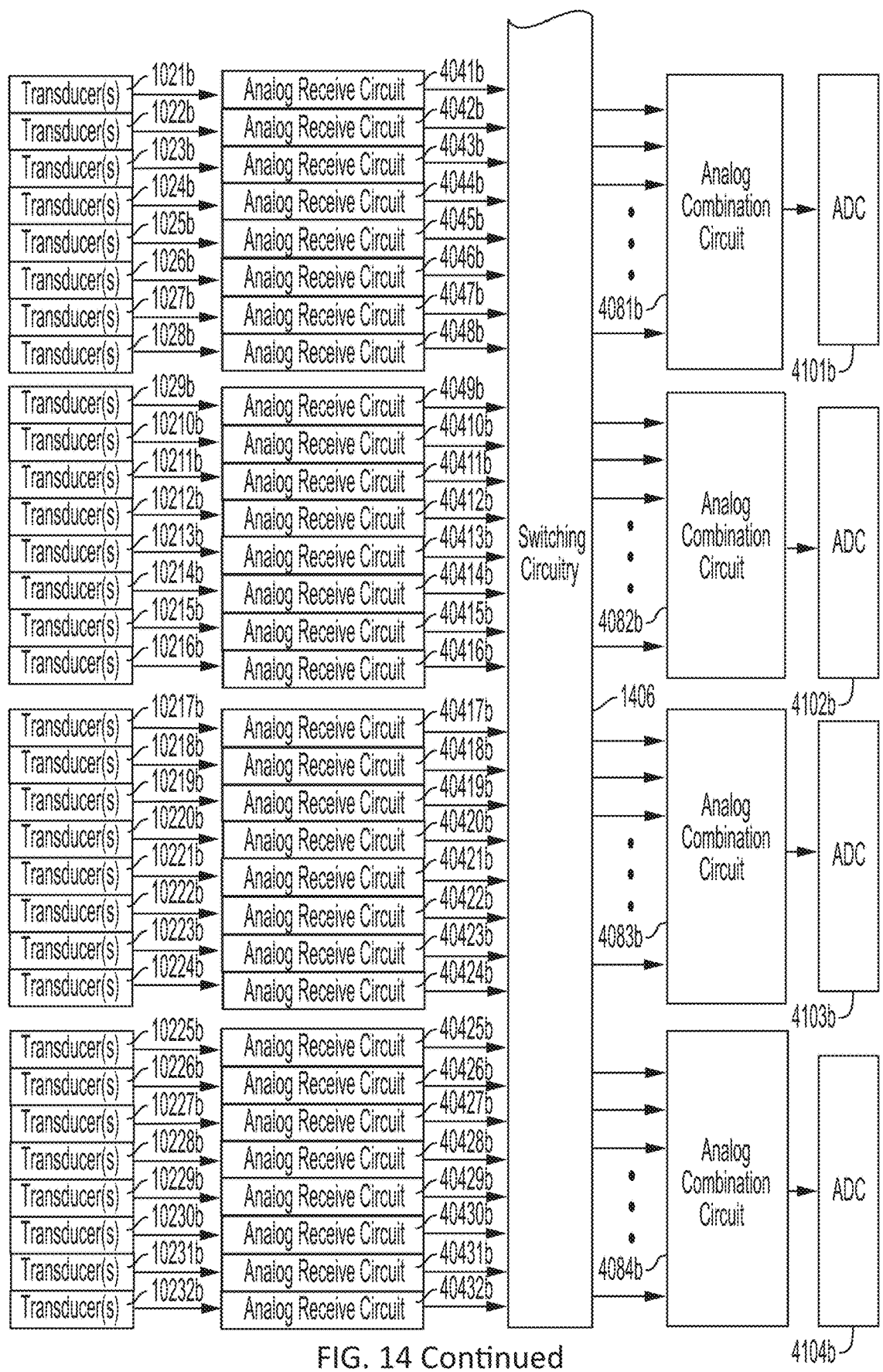

In some embodiments, ultrasound signals from two or more azimuthal columns 120 may be input to a single analog combination circuit 408. FIG. 14 shows an example of ultrasound circuitry that may be configured to input ultrasound signals from two or more azimuthal columns 120 to one analog combination circuit 408. In various embodiments, a configuration where ultrasound signals from two or more azimuthal columns 120 are input to an analog combination circuit 408 may improve beam quality along the elevational direction 114 and/or may provide a higher frame rate in at least some imaging cases, as compared to configuration where ultrasound signals from a single azimuthal column 120 are input to an analog combination circuit 408 (e.g., as described above with references to FIGS. 4-5).

FIG. 14 illustrates a schematic block diagram of ultrasound circuitry, in accordance with certain embodiments described herein. FIG. 14 includes a non-limiting detailed implementation of the configurable processing circuitry 1302. The ultrasound circuitry illustrated in FIG. 14 may be implemented in the semiconductor chip 100 (or, in some embodiments, in multiple semiconductor chips). In particular, FIG. 14 illustrates ultrasound circuitry coupled to the ultrasonic transducers 102 in multiple azimuthal columns 120 (as illustrated, two azimuthal columns 120). The ultrasound circuitry includes analog receive circuits $404_{1a}$-$404_{32a}$ of a first azimuthal column 120, analog receive circuits $404_{1b}$-$404_{32b}$ of a second azimuthal column 120, switching circuitry 1406, analog combination circuits $408_{1a}$-$408_{4a}$ of a first azimuthal column 120, analog combination circuits $408_{1b}$-$408_{4b}$ of a second azimuthal column 120, analog-to-digital converters $410_{1a}$-$410_{4a}$ of a first azimuthal column 120, analog-to-digital converters $410_{1b}$-$410_{4b}$ of a second azimuthal column 120, and control circuitry 1418. The analog receive circuits, switching circuitry, and analog combination circuitry represent a non-limiting example of the configurable processing circuitry of FIG. 13. The analog receive circuits $404_{1a}$-$404_{32b}$ are coupled between the output terminals of the ultrasonic transducers $102_{1a}$-$102_{32b}$ (where each of one or more ultrasonic transducers 102 may include multiple ultrasonic transducers coupled together) and the input terminals of the switching circuitry 1406. The switching circuitry 1406 is coupled between the output terminals of the analog receive circuits $404_{1a}$-$404_{32b}$ and the input terminals of the analog combination circuits $408_{1a}$-$408_{4b}$. The analog combination circuits $408_{1a}$-$408_{4b}$ are coupled between the output terminals of the switching circuitry 1406 and the input terminals of the analog-to-digital converters $410_{1a}$-$410_{4}b$. Thus, the output terminal of two or more, and in some embodiments each, of the ultrasonic transducers $102_{1a}$-$102_{32b}$ may be coupled (either directly or through intervening circuitry not illustrated) to the input terminal of a respective analog receive circuit $404_{1a}$-$404_{32b}$. The output terminal of two or more, and in some embodiments each, of the analog receive circuits $404_{1a}$-$404_{32b}$ may be coupled to an input terminal of the switching circuitry 1406 (either directly or through intervening circuitry not illustrated). Each of two or more of the output terminals of the switching circuitry 1406 may be switchably coupled to an input terminal of a particular one of the analog combination circuits $408_{1a}$-$408_{4b}$ (either directly or through intervening circuitry not illustrated). The output terminal of each of two or more of the analog combination circuits $408_{1a}$-$408_{4b}$ may be coupled to the input terminal of a respective analog-to-digital converter $410_1a$-$410_4b$ (either directly or through intervening circuitry not illustrated). The output of the control circuitry 1418 may be coupled to the switching circuitry 1406 (although the control circuitry 1418 may control other circuitry illustrated in FIG. 14 or not, and thus may be coupled to circuitry through couplings not illustrated).

Figure 15:
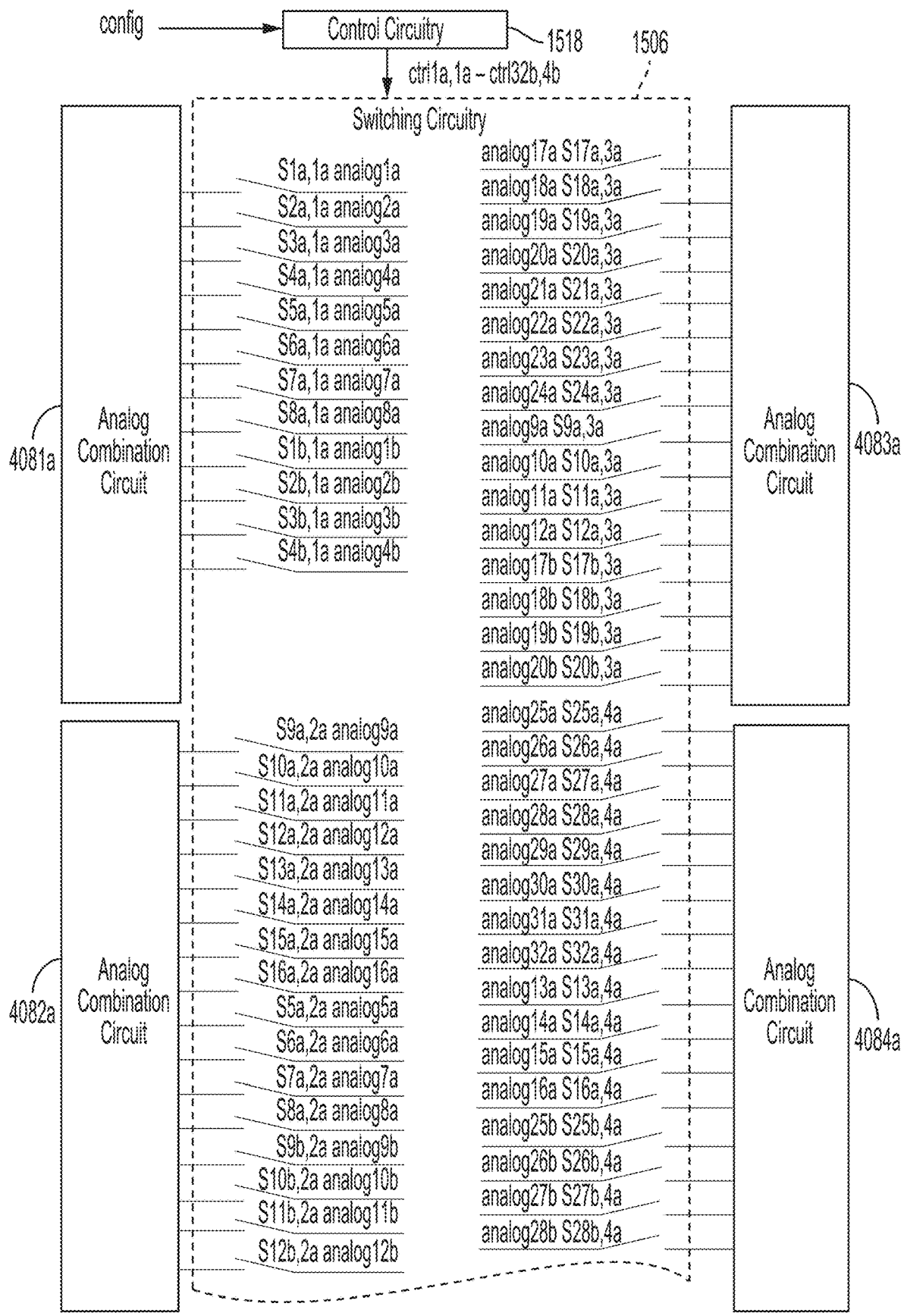
FIG. 15 illustrates a schematic block diagram of ultrasound circuitry, in accordance with certain embodiments described herein.
Figure 15:
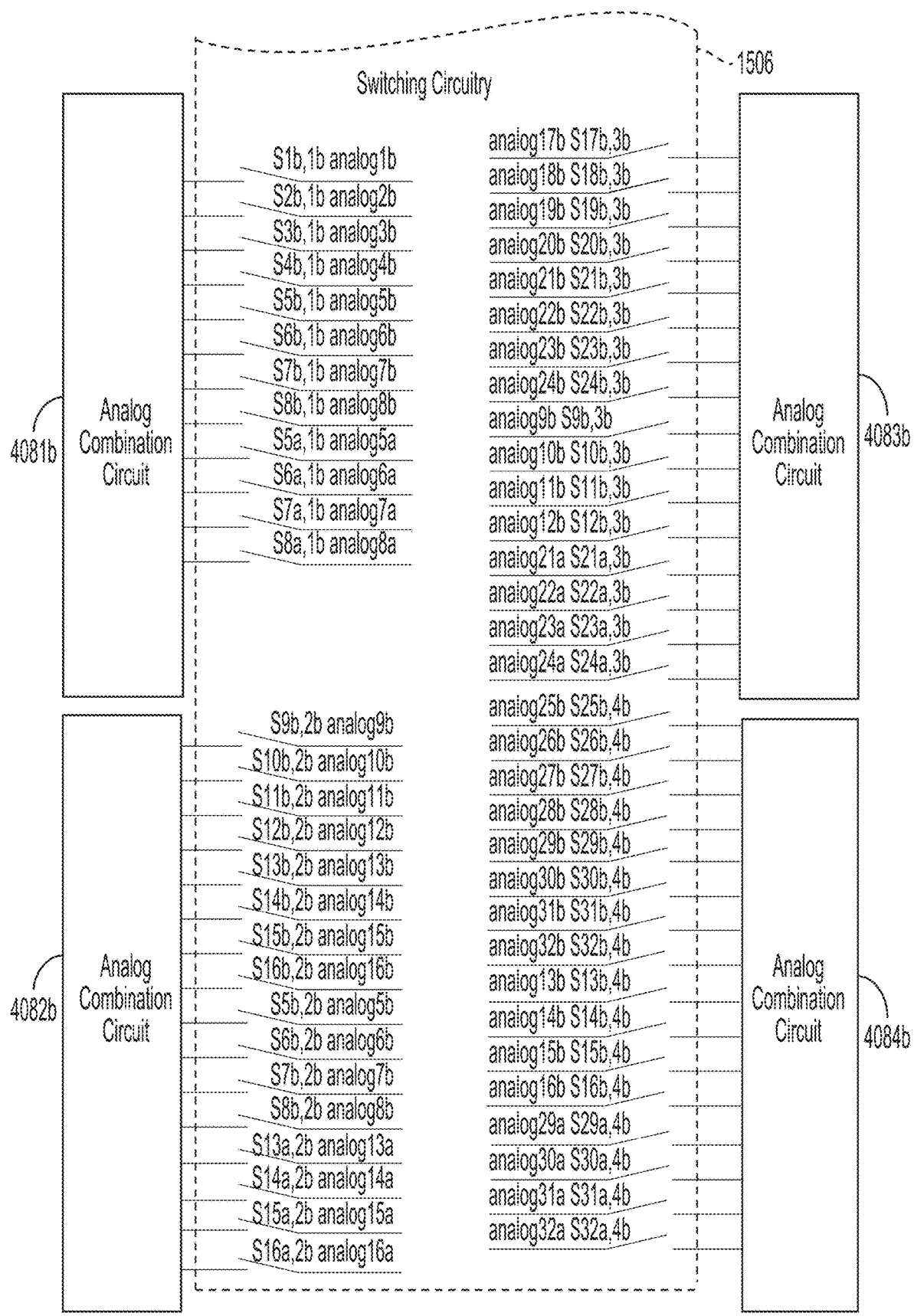

The switching circuitry 1406 may include multiple switches switchably coupling output terminals of certain analog receive circuits 404 of multiple azimuthal columns 120 to input terminals of certain analog combination circuits 408 of multiple azimuthal columns 120. One example is illustrated in FIG. 15. The control circuitry 1418 may be configured to control the switching circuitry 1406 to cause particular output terminals of the analog receive circuits 404 of multiple azimuthal columns 120 to be coupled through the switches of the switching circuitry 1406 to input terminals of particular analog combination circuits 408 of multiple azimuthal columns 120. Further description of various configurations may be found with reference to FIG. 15.

Each of two or more of the analog combination circuits $408_{1a}$-$408_{4b}$ may be configured to output a single analog output signal by combining multiple analog input signals. In some embodiments, the analog combination circuits $408_{1a}$-$408_{4b}$ may include analog averaging circuitry. In some embodiments, the analog combination circuits $408_{1a}$-$408_{4b}$ may include one or more resistors configured to passively sum multiple inputs. The ADCs $410_{1a}$-$410_{4}b$ may be configured to convert each output signal of an analog combination circuit 408 from analog to digital. Alternatively, in some embodiments, multiple analog combination circuits $408_{1a}$-$408_{4b}$ may be multiplexed to a single ADC 410. There may be further downstream processing circuitry not illustrated, such as digital filtering circuitry, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, backend processing circuitry and/or one or more output buffers. The image formation may be configured to perform apodization, back projection and/or fast hierarchy back projection, interpolation range migration (e.g., Stolt interpolation) or other Fourier resampling techniques, dynamic focusing techniques, delay and sum techniques, tomographic reconstruction techniques, Doppler calculation, frequency and spatial compounding, and/or low and high-pass filtering, etc.

FIG. 15 illustrates a particular embodiment where ultrasound signals from two or more azimuthal columns 120 may be input to a single analog combination circuit 408. FIG. 15 illustrates one exemplary arrangement of switching circuitry that is configured to input the ultrasound signals from two or more azimuthal columns 120 to one analog combination circuit 408 in at least one configuration. In the embodiment illustrated by FIG. 15, where ultrasound signals from two or more azimuthal columns 120 are be input to one analog combination circuit 408, there may be an improved beam quality along the elevational direction 114 and/or there may be a higher frame rate in at least some imaging cases, as compared to configuration where ultrasound signals from a single azimuthal column 120 are input to an analog combination circuit 408 (e.g., as described above with references to FIGS. 4-5).

FIG. 15 illustrates a schematic block diagram of ultrasound circuitry, in accordance with certain embodiments described herein. The ultrasound circuitry illustrated in FIG. 15 may be implemented in the semiconductor chip 100. The ultrasound circuitry illustrated in FIG. 15 is the same as in FIG. 14, except that FIG. 15 illustrates switching circuitry 1506 and control circuitry 1518, and no ADCs are illustrated even though they may be included and coupled to the analog combination circuitry in the same manner as shown in FIG. 14. The switching circuitry 1506 may be an example implementation of the switching circuitry 1406 and the control circuitry 1518 may be an example implementation of the control circuitry 1418, although it should be understood that alternative implementations of switching circuitry 1406 and control circuitry 1418 are possible. FIG. 15 further labels each output terminal of the analog receive circuits $404_{1a}$-$404_{32b}$ as $analog_{1a}$-$analog_{32b}$, respectively.

The switching circuitry 1506 includes sets of switches labeled $S_{1a,1a}$-$S_{32b,4b}$. In this non-limiting example, each of the switches in the switching circuitry 1506 switchably couples one of the outputs $analog_{1a}$-$analog_{32b}$ to an input of one of the analog combination circuits $408_{1a}$-$408_{4b}$. In the notation used for the switches $S_{1a,1a}$-$S_{32b,4b}$, the first subscripted number corresponds to the subscript of the analog receive circuit to which the switch is coupled on one end, and the second subscripted number corresponds to the subscript of the analog combination circuit to which the switch is coupled on the other end. The control circuitry 1518 outputs control signals $ctrl_{1a,1a}$-$ctrl_{32b,4b}$ to each switch $S_{1a,1a}$-$S_{32b,4b}$, respectively. The control circuitry 1518 may use the control signals $ctrl_{1a,1a}$-$ctrl_{32b,4b}$ to open or close certain of the switches $S_{1a,1a}$-$S_{32b,4b}$ in order to couple particular output terminals of the analog receive circuits $404_{1a}$-$404_{32b}$ to particular analog combination circuits $408_{1a}$-$408_{4b}$. It should be appreciated that the elevational aperture used may depend, at least in part, on which output signals of analog receive circuits 404 are coupled, through the switching circuitry 1506, to analog combination circuitry 408 and downstream circuitry, and which are not. Additionally, it should be appreciated that the resolution at which analog ultrasound signals are processed by the ultrasound circuitry illustrated in FIG. 15 may depend, at least in part, on how many output signals of analog receive circuits 404 are coupled to each analog combination circuit 408. Finer resolution may correspond to fewer analog ultrasound signals combined together and coarser resolution may correspond to more analog ultrasound signals combined together. Thus, more output signals of analog receive circuits 404 coupled to a given, and in some embodiments each, analog combination circuit 408 may correspond to coarser resolution and fewer output signals of analog receive circuits 404 coupled to a given, and in some embodiments each, analog combination circuit 408 may correspond to finer resolution. Thus, the control circuitry 1518 may control the switching circuitry 1506 to implement various configurations of resolution and elevational aperture.

For example, in one configuration, the control circuitry 1518 may cause the switches $S_{1a,1a}$-$S_{8a,1a}$, $S_{9a,2a}$-$S_{16a,2a}$, $S_{17a,3a}$-$S_{24a,3a}$, $S_{25a,4a}$-$S_{32a,4a}$, $S_{1b,1b}$-$S_{8b,1b}$, $S_{9b,2b}$-$S_{16b,2b}$, $S_{17b,3b}$-$S_{24b,3b}$, and $S_{25b,4b}$-$S_{32b,4b}$ to be closed and the others to be open. Thus, the eight output terminals $analog_{1a}$-$analog_{8a}$ may be coupled to the analog combination circuit $408_{1a}$, the eight output terminals $analog_{9a}$-$analog_{16a}$ may be coupled to the analog combination circuit $408_{2a}$, the eight output terminals $analog_{17a}$-$analog_{24a}$ may be coupled to the analog combination circuit $408_{3a}$, the eight output terminals $analog_{25a}$-$analog_{32a}$ may be coupled to the analog combination circuit $408_{4a}$, the eight output terminals $analog_{1b}$-$analog_{8b}$ may be coupled to the analog combination circuit $408_{1b}$, the eight output terminals $analog_{9b}$-$analog_{16b}$ may be coupled to the analog combination circuit $408_{2b}$, the eight output terminals $analog_{17b}$-$analog_{24b}$ may be coupled to the analog combination circuit $408_{3b}$, and the eight output terminals $analog_{25b}$-$analog_{32b}$ may be coupled to the analog combination circuit $408_{4b}$, This may show an additional example of an "8×1" configuration, because 8 (8×) analog receive circuits 404 of one (×1) azimuthal column are coupled to each analog combination circuit 408.

In another configuration, the control circuitry 1518 may cause the switches $S_{1a,1a}$-$S_{4a,1a}$, $S_{5a,2a}$-$S_{8a,2a}$, $S_{9a,3a}$-$S_{12a,3a}$, $S_{13a,4a}$-$S_{16a,4a}$, $S_{1b,1b}$-$S_{4b,1b}$, $S_{5b,2b}$-$S_{8b,2b}$, $S_{9b,3b}$-$S_{12b,3b}$, and $S_{13b,4b}$-$S_{16b,4b}$ to be closed and the others to be open. Thus, the four output terminals $analog_{1a}$-$analog_{4a}$ may be coupled to the analog combination circuit $408_{1a}$, the four output terminals $analog_{5a}$-$analog_{8a}$ may be coupled to the analog combination circuit $408_{2a}$, the four output terminals $analog_{9a}$-$analog_{12a}$ may be coupled to the analog combination circuit $408_{3a}$, the four output terminals $analog_{13a}$-$analog_{16a}$ may be coupled to the analog combination circuit $408_{4a}$, the four output terminals $analog_{1b}$-$analog_{4b}$ may be coupled to the analog combination circuit $408_{1b}$, the four output terminals $analog_{5b}$-$analog_{8b}$ may be coupled to the analog combination circuit $408_{2b}$, the four output terminals $analog_{9b}$-$analog_{12b}$ may be coupled to the analog combination circuit $408_{3b}$, and the four output terminals $analog_{13b}$-$analog_{16b}$ may be coupled to the analog combination circuit $408_{4b}$ The output terminals $analog_{17a}$-$analog_{32a}$ and $analog_{17b}$-$analog_{32b}$ may not be coupled to any of the analog combination circuits $408_{1a}$-$408_{4b}$. In other words, the output terminals $analog_{17a}$-$analog_{32a}$ and $analog_{17b}$-$analog_{32b}$ of the analog receive circuits $404_{17a}$-$404_{32a}$ $404_{17b}$-$404_{32b}$ (which are, in turn, processing signals outputted by the ultrasonic transducers $102_{17a}$-$102_{32a}$ and $102_{17b}$-$102_{32b}$) may not be processed in this configuration. This may show an additional example of a "4×1" configuration because 4 (4×) analog receive circuits 404 of one (×1) azimuthal column are coupled to each analog combination circuit 408.

In another configuration, the control circuitry 1518 may cause the switches $S_{1a,1a}$-$S_{4a,1a}$, $S_{1b,1a}$-$S_{4b,1a}$, $S_{5a,1b}$-$S_{8a,1b}$, $S_{5b,1b}$-$S_{8b,1b}$, $S_{9a,2a}$-$S_{12a,2a}$, $S_{9b,2a}$-$S_{12b,2a}$, $S_{13a,2b}$-$S_{16a,2b}$, $S_{13b,2b}$-$S_{16b,2b}$, $S_{17a,3a}$-$S_{20a,3a}$, $S_{17b,3a}$-$S_{20b,3a}$, $S_{21a,3b}$-$S_{24a,3b}$, $S_{21b,3b}$-$S_{24b,3b}$, $S_{25a,4a}$-$S_{28a,4a}$, $S_{25b,4a}$-$S_{28b,4a}$, $S_{29a,4b}$-$S_{32a,4b}$, and $S_{29b,4b}$-$S_{32b,4b}$ to be closed and the others to be open. Thus, the eight output terminals $analog_{1a}$-$analog_{4a}$ and $analog_{1b}$-$analog_{4b}$ may be coupled to the analog combination circuit $408_{1a}$, the eight output terminals $analog_{5a}$-$analog_{8a}$ and $analog_{5b}$-$analog_{8b}$ may be coupled to the analog combination circuit $408_{1b}$, the eight output terminals $analog_{9a}$-$analog_{12a}$ and $analog_{9b}$-$analog_{12b}$ may be coupled to the analog combination circuit $408_{2a}$, the eight output terminals $analog_{13a}$-$analog_{16a}$ and $analog_{13b}$-$analog_{16b}$ may be coupled to the analog combination circuit $408_{2b}$, the eight output terminals $analog_{17a}$-$analog_{20a}$ and analog$_{17b}$-analog$_{20b}$ may be coupled to the analog combination circuit $408_{3a}$, the eight output terminals analog$_{21a}$-analog$_{24a}$ and analog$_{21b}$-analog$_{24b}$ may be coupled to the analog combination circuit $408_{3b}$, the eight output terminals analog$_{25a}$-analog$_{28a}$ and analog$_{25b}$-analog$_{28b}$ may be coupled to the analog combination circuit $408_{4a}$, the eight output terminals analog$_{29a}$-analog$_{32a}$ and analog$_{29b}$-analog$_{32b}$ may be coupled to the analog combination circuit $408_{4b}$. This may be referred to as a "4×2" configuration because, 4 (4×) analog receive circuits 404 of two (×2) azimuthal columns are coupled to each analog combination circuit 408.

The above description of the 4×2 configuration assumes that all two sets of 32 output terminals analog$_{1a}$-analog$_{32b}$ are coupled to analog combination circuits 408. Variants of the 4×2 combination may include decoupling from analog combination circuits 408 certain of the output terminals analog$_{1a}$-analog$_{32b}$ that are coupled to analog combination circuits 408 in the 4×2 configuration. For example, to implement an example variant of the 4×2 configuration that includes coupling two sets of 17 output terminals, analog$_{1a}$-analog$_{17a}$ and analog$_{1b}$-analog$_{17b}$ to analog combination circuits 408, the control circuitry 1518 may cause the switches $S_{1a,1a}$-$S_{4a,1a}$, $S_{1b,1a}$-$S_{4b,1a}$, $S_{5a,1b}$-$S_{8a,1b}$, $S_{5b,1b}$-$S_{8b,1b}$, $S_{9a,2a}$-$S_{12a,2a}$, $S_{9b,2a}$-$S_{12b,2a}$, $S_{13a,2b}$-$S_{16a,2b}$, $S_{13b,2b}$-$S_{16b,2b}$, $S_{17a,3a}$, and $S_{17b,3a}$ to be closed and the others to be open. Thus, the eight output terminals analog$_{1a}$-analog$_{4a}$ and analog$_{1b}$-analog$_{4b}$ may be coupled to the analog combination circuit $408_{1a}$, the eight output terminals analog$_{5a}$-analog$_{8a}$ and analog$_{5b}$-analog$_{8b}$ may be coupled to the analog combination circuit $408_{1b}$, the eight output terminals analog$_{9a}$-analog$_{12a}$ and analog$_{9b}$-analog$_{12b}$ may be coupled to the analog combination circuit $408_{2a}$, the eight output terminals analog$_{13a}$-analog$_{16a}$ and analog$_{13b}$-analog$_{16b}$ may be coupled to the analog combination circuit $408_{2b}$, and the two output terminals analog$_{17a}$ and analog$_{17b}$ may be coupled to the analog combination circuit $408_{3a}$. In other words, the output terminals analog$_{18a}$-analog$_{32a}$ and analog$_{18b}$-analog$_{32b}$ from the analog receive circuits $404_{18a}$-$404_{32a}$ and $404_{18b}$-$404_{32b}$ (which are, in turn, processing signals outputted by the ultrasonic transducers $102_{18a}$-$102_{32a}$ and $102_{18b}$-$102_{32b}$) may not be processed in this configuration. Additionally, no output terminals from analog receive circuits 404 are coupled to the analog combination circuits $408_{3b}$, $408_{4a}$, or $408_{4b}$. While this example variant includes coupling two sets of 17 output terminals analog$_{1a}$-analog$_{17a}$ and analog$_{1b}$-analog$_{17b}$ to analog combination circuits 408, any number of output terminals of two sets of 1-32, (or one set of a first value 1-32 and one set of a second value of 1-32 different than the first value) may be coupled to analog combination circuits 408.

In a 4×2 configuration, analog combination circuits 408 may sum signals from multiple columns. In some embodiments, the multiple columns may be adjacent along the azimuthal direction 116. In contrast, in a ×1 configuration such as a 4×1 configuration, analog combination circuits 408 may not sum signals from multiple columns and may instead sum signals from a single column. A 4×2 configuration may provide advantages compared to other configurations.

When comparing an 8×1 configuration with a 4×2 configuration, these two configurations may have differences. First, an 8×1 configuration and a 4×2 configuration may have different beam qualities along the azimuthal direction 116 and along the elevational direction 114. For a k×j configuration, (e.g., 4×2 or 8×1), k and j may relate to size of a patch of ultrasound transducers forming a sub-array and sub-aperture, where the size is k elements in the elevational direction 114 and j elements in the azimuthal direction 116. A larger patch size may provide stronger directivity, may provide reduced patch level grating lobe, and/or may provide reduced beam quality. Accordingly, when using a 4×2 configuration rather than an 8×1 configuration, beam quality may be improved along the elevational direction 114 at the cost of reduced beam quality along the azimuthal direction 116. Second, an 8×1 configuration and a 4×2 configuration may have different of frame rates when singulation is performed. Compared with an 8×1 configuration, a 4×2 configuration may allow a higher frame rate in at least some imaging cases. For example, a 4×2 configuration may allow a higher frame rate in imaging cases that involve elevational tilt (e.g., biplane imaging, in which an ultrasound device collects ultrasound images with two imaging planes, and/or 3-D imaging). For example, when using 2 elements per patch along the elevational direction 114 (for example, because a large number of elements per patch may limit tilt capabilities), then 2 singulations may be used in a 4×2 configuration, as compared to where 4 singulations may be used in an 8×1 configuration, which may provide higher frame rate.

When comparing an 4×1 configuration with a 4×2 configuration, these two configurations may have differences. For example, an advantage that a 4×2 configuration may have over a 4×1 configuration is that the 4×2 configuration may provide a higher frame rate because less data needs to be offloaded and processed. As another example, an advantage that a 4×1 configuration may have over a 4×2 configuration is that the 4×1 configuration may have better beam quality along the azimuthal direction 116. Better beam quality along the azimuthal direction 116 may provide benefits for imaging at shallow or very shallow depths (for example, imaging at a depth of about 1 cm).

The control circuitry 1518 may be configured to control the switching circuitry 1506 to implement any, and in some embodiments each, of these configurations, and which configuration the control circuitry 1518 controls the switching circuitry 1506 to implement may be based on a control parameter received by the control circuitry 1518, and labeled as "config" in FIG. 15. The control circuitry 1518 may be configured to control the switching circuitry 1506 to implement one configuration and then implement another configuration when the received control parameter changes. Generally, the control circuitry may be configured to control the switching circuitry 1506 to implement one configuration and then implement another configuration having a larger elevational aperture but coarser resolution. Additionally, the control circuitry may be configured to control the switching circuitry 1506 to implement one configuration and then implement another configuration having a smaller elevational aperture but finer resolution. For example, the control circuitry 1518 may control the switching circuitry 1506 to do any or all of the following: implement the 8×1 configuration and then the 4×1 configuration (smaller elevational aperture and finer resolution), to implement the 8×1 configuration and then the 4×2 configuration (improved beam quality along the elevational direction 114, reduced beam quality along the azimuthal direction 116, higher frame rates in at least some imaging cases), to implement the 4×1 configuration and then the 4×2 configuration (higher frame rates, reduced beam quality along the azimuthal direction 116), to implement the 4×1 configuration and then the 8×1 configuration (larger elevational aperture and coarser resolution), to implement the 4×2 configuration and then the 4×1 configuration (improved beam quality along the azimuthal direction 116, reduced frame rates), and to implement the 4×2 configuration and then the 8×1 configuration (improved beam quality along the azimuthal direction 116, reduced beam quality along the elevational direction 114, reduced frame rates in at least some imaging cases).

In embodiments in which each of the switches $S_{1a,1a}$-$S_{32b,4b}$ is an N-type metal-oxide-semiconductor (nMOS) transistor, the control circuitry 1518 may cause the control signals $ctrl_{1a,1a}$-$ctrl_{32a,4a}$ to be a digital high voltage to close the corresponding switches and a digital low voltage to open the corresponding switches. In embodiments in which each of the switches $S_{1a,1a}$-$S_{32b,4b}$ is a P-type metal-oxide-semiconductor (pMOS) transistor, the control circuitry 1518 may cause the control signals $ctrl_{1a,1a}$-$ctrl_{32b,4b}$ to be a digital low voltage to close the corresponding switches and a digital high voltage to open the corresponding switches. In some embodiments, one or more, and in some embodiments each, of the control signals $ctrl_{1a,1a}$-$ctrl_{32b,4b}$ may include multiple individual control signals. For example, in embodiments in which each of the switches $S_{1a,1a}$-$S_{32b,4b}$ is a transmission gate having nMOS transistor and a pMOS transistor, to close a given switch, the control circuitry 1518 may output a control signal including a digital high voltage applied to the gate of the nMOS transistor and a digital low voltage applied to the gate of the pMOS transistor. To open a given switch, the control circuitry 1518 may output a control signal including a digital low voltage applied to the gate of the nMOS transistor and a digital high voltage applied to the gate of the pMOS transistor. It should be appreciated that other types of switches may be used and different types of switches may use different types of control signals. The control circuitry 1518 may be configured to receive a configuration parameter config associated with a particular configuration (e.g., associated with the 4×2, 4×1, or 8×1 configuration) based on which the control circuitry 1518 may output control signals $ctrl_{1a,1a}$-$ctrl_{32b,4b}$ particular to that configuration. As described above, the specific configuration parameter config received by the control circuitry 1518 may be generated based on the imaging depth selection, the anatomy selected for imaging, the power level of the ultrasound device, and/or a power mode selection. Further description of generation of the configuration parameter config will be described with reference to FIGS. 6-8B.

Generally, variants of the configurations described may be implemented by coupling particular outputs $analog_{1a}$-$analog_{32b}$ to particular analog combination circuits $408_{1a}$-$408_{4b}$ by closing or opening the appropriate switches $S_{1a,1a}$-$S_{32b,4b}$ using the corresponding control signals $ctrl_{1a,1a}$-$ctrl_{32b,4b}$.

It should be appreciated that the output terminals of certain analog receive circuits 404 are switchably coupled, through the switching circuitry 1506, to input terminals of multiple analog combination circuits 408. Additionally, the output terminals of certain analog receive circuits 404 are switchably coupled, through the switching circuitry, to input terminals of multiple but not all of the analog combination circuits $408_{1a}$-$408_{4b}$. For example, $analog_{16a}$ is switchably coupled to the analog combination circuit $408_{2a}$ through the switch $S_{16a,2a}$, to the analog combination circuit $408_{4a}$ through the switch $S_{16a,4a}$, to the analog combination circuit $408_{2b}$ through the switch $S_{16a,2b}$, but not to the other analog combination circuits. It should also be appreciated from the above description that, when configuring the ultrasound device in one configuration and then in another configuration, the control circuitry 1518 may cause a particular output terminal of an analog receive circuit 404 to be coupled to one of the analog combination circuits 408 in the first configuration and then to be coupled to a different one of the analog combination circuits 408 in the second configuration. As one non-limiting example, as described above, in the 8×1 configuration, $analog_{16}$ may be coupled to the analog combination circuit $408_{2a}$, in the 4×1 configuration $analog_{16}$ may be coupled to the analog combination circuit $408_{4a}$, and in the 4×2 configuration $analog_{16}$ may be coupled to the analog combination circuit $408_{2b}$.

It should also be appreciated that certain output terminals of the analog receive circuits 404 are switchably coupled to different number of analog combination circuits 408. For example, $analog_{1a}$ is switchably coupled just to the analog combination circuit $408_{1a}$ while $analog_{16}$ is switchably coupled to the analog combination circuits $408_{2a}$, $408_{4a}$, and $408_{2b}$. It should also be appreciated that in the switching circuitry 1506, none of the output terminals $analog_{1a}$-$analog_{32b}$ are switchably coupled to input terminals of each analog combination circuit $408_{1a}$-$408_{4b}$. In some other embodiments, some but fewer than 25%, 50%, or 75% of the analog receive circuits 404 are switchably coupled to each analog combination circuit $408_{1a}$-$408_{4b}$.

The switching circuitry 1506 is an example of a topology that provides sufficient flexibility for different, continuous elevational apertures (e.g., the elevational apertures 324A and 324B) to be used, with increased resolution for reduced sized apertures, and without decrease in frame rate. The specific design may include the choices of which of the output terminals of the analog receive circuits 404 are switchably coupled to which of the analog combination circuits 408, such as the choice to couple $analog_1$ only to the analog combination circuit $408_{1a}$ but to couple $analog_{16}$ to the analog combination circuits $408_{2a}$, $408_{4a}$, and $408_{2b}$. Additionally, the switching circuitry 1506 is an example of a topology in which at least some analog receive circuits 404 are not coupled to all the analog combination circuits $408_{1a}$-$408_{4b}$, and may therefore avoid excessive routing and degradation of signal quality.

A small elevational aperture may be helpful, for example, when imaging in the near field where the outer elements are too far away (or at too high of an angle off-center) to add value to the image at shallow depths; when imaging through the ribs (e.g., in cardiac ultrasound imaging, and especially in pediatric cardiac ultrasound imaging); and/or when conserving power by not using the whole aperture. Thus, the specific configuration parameter config received by the control circuitry 418, 518, 1418, and/or 1518 may be generated based on the imaging depth selection, the anatomy selected for imaging, the power level of the ultrasound device, and/or the power mode for the ultrasound device. Further description of generation of the configuration parameter config will be described with reference to FIGS. 6-8B. This may be specifically helpful, in one non-limiting example use case, when using a universal ultrasound device capable of operating at multiple different medically-relevant frequency ranges appropriate for forming medically-relevant images of different anatomical features or regions. In such a case it may be desirable to perform imaging of one anatomical feature or region for which an elevational aperture of one size is appropriate, and then perform imaging of another anatomical feature or region for which an elevational aperture of a smaller size is appropriate. When reducing the size of the elevational aperture, the circuits and methods described herein may allow for more efficient use of the full processing capability of the ultrasound device to process the fewer number of ultrasound signals at a finer resolution than when using a larger aperture, without decreasing the frame rate.

While the above description and figures illustrate an example in which each azimuthal column 120 has 32 ultrasonic transducers 102, this is non-limiting, and each azimuthal column may have more than 32 ultrasonic transducers 102 or fewer than 32 ultrasonic transducers 102. While the figures described above illustrate an example in which there is one set of azimuthal columns 120 each having 32 ultrasonic transducers 102 above the elevational center 112 of the ultrasonic transducer array 126 and another set of azimuthal columns 120 each having 32 ultrasonic transducers 102 below the elevational center 112 of the ultrasonic transducer array 126, in some embodiments there may be more than one set of azimuthal columns 120 above the elevational center 112 and/or more than one set of azimuthal columns 120 below the elevational center 112, or in some embodiments there may be only one set of azimuthal columns 120. Additionally, in some embodiments, there may be more than 32 ultrasonic transducers 102 above and below the elevational center 112 or fewer than 32 ultrasonic transducers 102 above and below the elevational center 112.

While the above description and figures illustrate examples in which there are four analog combination circuits 408₁-408₄ or eight analog combination circuits 408₁ₐ-408₄ᵦ, this is non-limiting, and in some embodiments there may be more than four or fewer than four or more than eight or fewer than eight. While the above description and figures illustrate examples in which there are four ADCs 410₁-410₄ or eight ADCs 410₁ₐ-410₄ᵦ, this is non-limiting, and in some embodiments there may be more than four or fewer than four or more than eight or fewer than eight. For example, in embodiments in which each analog combination circuit 408 is coupled to a different ADC 410, there may be more or fewer ADCs 410 based on how many analog combination circuits 408 there. In some embodiments, there may be fewer ADCs 410 than analog combination circuits 408, and the output terminals of multiple analog combination circuits 408 may be multiplexed to a single ADC 410.

While the above description and figures illustrate example 8×1, 4×1, 2×1, and 4×2 configurations and variants thereof, these configurations are non-limiting, and other configurations may be used. For example, control circuitry may control switching circuitry to implement a 4×2 configuration and a 2×1 configuration. As another example, control circuitry may control switching circuitry to couple the output terminals of three (3×) analog receive circuits 404 of one (×1) azimuthal column to each analog combination circuit 408 for a 3×1 configuration, to couple the output terminals of five (5×) analog receive circuits 404 of one (×1) azimuthal column to each analog combination circuit 408 for a 5×1 configuration, to couple the output terminals of two (2×) analog receive circuits 404 of four (×4) azimuthal columns to each analog combination circuit 408 for a 2×4 configuration, and generally to couple the output terminals of k analog receive circuits 404 of j azimuthal columns to each analog combination circuit 408 for a k×j configuration (where k may be, for example, 2, 4, 8, 16, 32, 64, 128, or any other suitable number, and not necessarily a power of 2, and where j may be, for example, 2, 4, 8, 16, 32, 64, 128, or any other suitable number, and not necessarily a power of 2). Generally, a k×1 configuration using n ultrasonic transducers 102₁-102ₙ may include using n/k, rounded up to the nearest integer, analog combination circuits 408. Let m=n/k rounded up to the nearest integer. Then, k output terminals of analog receive circuits 404 may be coupled to input terminals of each of m−1 analog combination circuits 408, and n−k*(m−1) output terminals of analog receive circuits 404 may be coupled to input terminals of one (1) analog combination circuit 408.

While the above description and figures illustrate example configurations that utilize the full elevational aperture, the centermost 50% of the elevational aperture, and the centermost 25% of the elevational aperture, these aperture sizes are non-limiting, and configurations using other aperture sizes may be used. For example, control circuitry may control switching circuitry to couple the output terminals of the centermost third or two-thirds of the ultrasonic transducers 102 along the elevational dimension 114 of the ultrasonic transducer array 126 to analog combination circuits 408 such that the centermost third or two-thirds, respectively, of the elevational aperture is used. As another example, control circuitry may control switching circuitry to couple the output terminals of the centermost 20%, 40%, 60%, or 80% of the ultrasonic transducers 102 along the elevational dimension 114 of the semiconductor chip to analog combination circuits 408 such that the centermost 20%, 40%, 60%, or 80%, respectively, of the elevational aperture is used. Generally, control circuitry may control switching circuitry to couple the output terminals of the centermost k % of the ultrasonic transducers 102 to analog combination circuits 408 such that the centermost k % of the elevational aperture is used (where k may be, for example, 5, 10, 15, 20, 25, 30, 35, 40, 45, 50, 55, 60, 65, 70, 75, 80, 85, 90, 95, 100, or any other suitable number, and not necessarily a power of 5).

FIGS. 6, 7, 8A and 8B illustrate flow diagrams of processes 600, 700, 800A, and 800B, respectively, for generating configuration indications for configuring an ultrasound device, in accordance with certain embodiments described herein. The processes 600, 700, 800A, and 800B are performed by a processing device (in some embodiments, control circuitry in the processing device more specifically) in operative communication with the ultrasound device. The processing device and the ultrasound device may communicate over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link.

In act 602 of the process 600, the processing device receives a selection of an anatomy for imaging. For example, the processing device may display on its display screen multiple options of anatomies for imaging, and the processing device may receive from a user a selection of one of the options. In act 604, the processing device generates a configuration indication (e.g., a digital signal having a particular value) associated with the anatomy selected in act 602. In some embodiments, memory on the processing device may store associations between configuration indications and anatomies. Thus, each anatomy may be associated with a particular configuration indication, and each configuration indication may be associated with a particular configuration of the ultrasound device. Each configuration (e.g., the 8×1, 4×1, 2×1, and/or 4×2 configurations described above) may include collecting ultrasound data with a certain portion of the elevational aperture and processing that ultrasound data with a certain resolution. For example, cardiac ultrasound imaging (e.g., pediatric or adult), which may benefit from a smaller elevational aperture more than, for example, abdominal ultrasound imaging, may be associated with a configuration that includes collecting ultrasound data with a smaller elevational aperture and finer resolution than abdominal imaging. The processing device may look up in the memory the configuration indication associated with the selected anatomy and transmit (e.g., over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link) this configuration indication, or a second configuration indication generated based on this first configuration indication, to the ultrasound device. The configuration indication received by the ultrasound device may be the same as the configuration parameter config described above, or config may be generated based on the configuration indication received by the ultrasound device. The ultrasound device may use the configuration indication to configure itself in a particular configuration as described above.

In some embodiments, act 602 may be absent, and the processing device may generate a configuration indication associated with a particular anatomy to be imaged without first receiving a selection of the particular anatomy. For example, the processing device may be operating through an automatic workflow that includes a step in which a particular anatomy is imaged. Upon reaching this step in the workflow, the processing device may generate a configuration indication associated with the particular anatomy to be imaged at this step as described above. In some embodiments, the ultrasound device itself may receive the selection of the anatomy for imaging and generate the configuration indication associated with the anatomy, or generate the configuration indication associated with the anatomy without a previous selection.

In act 702 of the process 700, the processing device receives a selection of an imaging depth. For example, the processing device may display on its display screen a control for selecting the imaging depth, and the processing device may receive from a user a selection of an imaging depth through the user operating this control. In act 704, the processing device generates a configuration indication (e.g., a digital signal having a particular value) associated with the imaging depth selected in act 702. In some embodiments, memory on the processing device may store associations between configuration indications and ranges of imaging depth. Thus, each range of imaging depth (and therefore every imaging depth within a given range) may be associated with a particular configuration indication, and each configuration indication may be associated with a particular configuration of the ultrasound device. Each configuration (e.g., the 8×1, 4×1, 2×1, and/or 4×2 configurations described above) may include collecting ultrasound data with a certain portion of the elevational aperture and processing that ultrasound data with a certain resolution. For example, ultrasound imaging at shallower imaging depths, which may benefit from a smaller elevational aperture more than ultrasound imaging at deeper imaging depths, may be associated with a configuration that includes collecting ultrasound data with a smaller elevational aperture and finer resolution than ultrasound imaging at deeper imaging depths. The processing device may look up in the memory the configuration indication associated with the range of imaging depths within which the selected imaging depth falls and transmit (e.g., over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link) this configuration indication, or a second configuration indication generated based on this first configuration indication, to the ultrasound device. The configuration indication received by the ultrasound device may be the same as the configuration parameter config described above, or config may be generated based on the configuration indication received by the ultrasound device. The ultrasound device may use the configuration indication to configure itself in a particular configuration as described above.

In some embodiments, act 702 may be absent, and the processing device may generate a configuration indication associated with a particular imaging depth without first receiving a selection of the particular anatomy. For example, the processing device may be operating through an automatic workflow that includes a step in which a particular imaging depth is used. Upon reaching this step in the workflow, the processing device may generate a configuration indication associated with the particular imaging depth to be used at this step as described above. In some embodiments, the ultrasound device itself may receive the selection of the imaging depth and generate the configuration indication associated with the imaging depth, or generate the configuration indication associated with the imaging depth without a previous selection.

In act 802A of the process 800A, the processing device determines a power level of the ultrasound device (i.e., a power level of a battery in the ultrasound device). For example, to determine the power level of the ultrasound device, the processing device may receive from the ultrasound device (e.g., over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link) an indication of its power level. In act 804A, the processing device generates a configuration indication (e.g., a digital signal having a particular value) associated with the power level of the ultrasound device determined in act 802A. In some embodiments, memory on the processing device may store associations between configuration indications and ranges of power level. Thus, each range of power level (and therefore every power level within a given range) may be associated with a particular configuration indication, and each configuration indication may be associated with a particular configuration of the ultrasound device. Each configuration (e.g., the 8×1, 4×1, 2×1, and/or 4×2 configurations described above) may include collecting ultrasound data with a certain portion of the elevational aperture and processing that ultrasound data with a certain resolution. For example, ultrasound imaging at lower power levels, which may benefit from a smaller elevational aperture (which may consume less power) more than ultrasound imaging at higher power levels, may be associated with a configuration that includes collecting ultrasound data with a smaller elevational aperture and finer resolution than ultrasound imaging at higher power levels. The processing device may look up in the memory the configuration indication associated with the range of power level within which the determined power level falls and transmit (e.g., over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link) this configuration indication, or a second configuration indication generated based on this first configuration indication, to the ultrasound device. The configuration indication received by the ultrasound device may be the same as the configuration parameter config described above, or config may be generated based on the configuration indication received by the ultrasound device. The ultrasound device may use the configuration indication to configure itself in a particular configuration as described above. In some embodiments, the ultrasound device itself may determine its own power level and generate the configuration indication associated with the power level.

In act 802B of the process 800, the processing device receives a selection of a power mode. For example, the processing device may display on its display screen a control for selecting the power mode, and the processing device may receive from a user a selection of a power mode through the user operating this control. Example power modes may include low power mode and normal power mode (or, more generally, a non-low power mode). Low power mode may include specific configurations of the ultrasound device that conserve power of the ultrasound device. As one non-limiting example use case, a user may select low power mode when the user expects to use the ultrasound device for an extended time without recharging the ultrasound device's battery. In act 804B, the processing device generates a configuration indication (e.g., a digital signal having a particular value) associated with the power mode selected in act 802B. In some embodiments, memory on the processing device may store associations between configuration indications and power modes. Each configuration (e.g., the 8×1, 4×1, 2×1, and/or 4×2 configurations described above) may include collecting ultrasound data with a certain portion of the elevational aperture and processing that ultrasound data with a certain resolution. For example, ultrasound imaging in a low power mode may benefit from a smaller elevational aperture, which may consume less power. The processing device may look up in the memory the configuration indication associated with the selected power mode and transmit (e.g., over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link) this configuration indication, or a second configuration indication generated based on this first configuration indication, to the ultrasound device. The configuration indication received by the ultrasound device may be the same as the configuration parameter config described above, or config may be generated based on the configuration indication received by the ultrasound device. The ultrasound device may use the configuration indication to configure itself in a particular configuration as described above.

While FIGS. 6-8B illustrate three examples of generating configuration indications, it should be appreciated that configuration indications may be generated in response to other events besides selection of anatomy, selection of imaging depth, determination of a power level of the ultrasound device, and/or selection of a power mode for the ultrasound device. In other words, it may be helpful to change configurations based on other factors besides these three.

Figure 9:
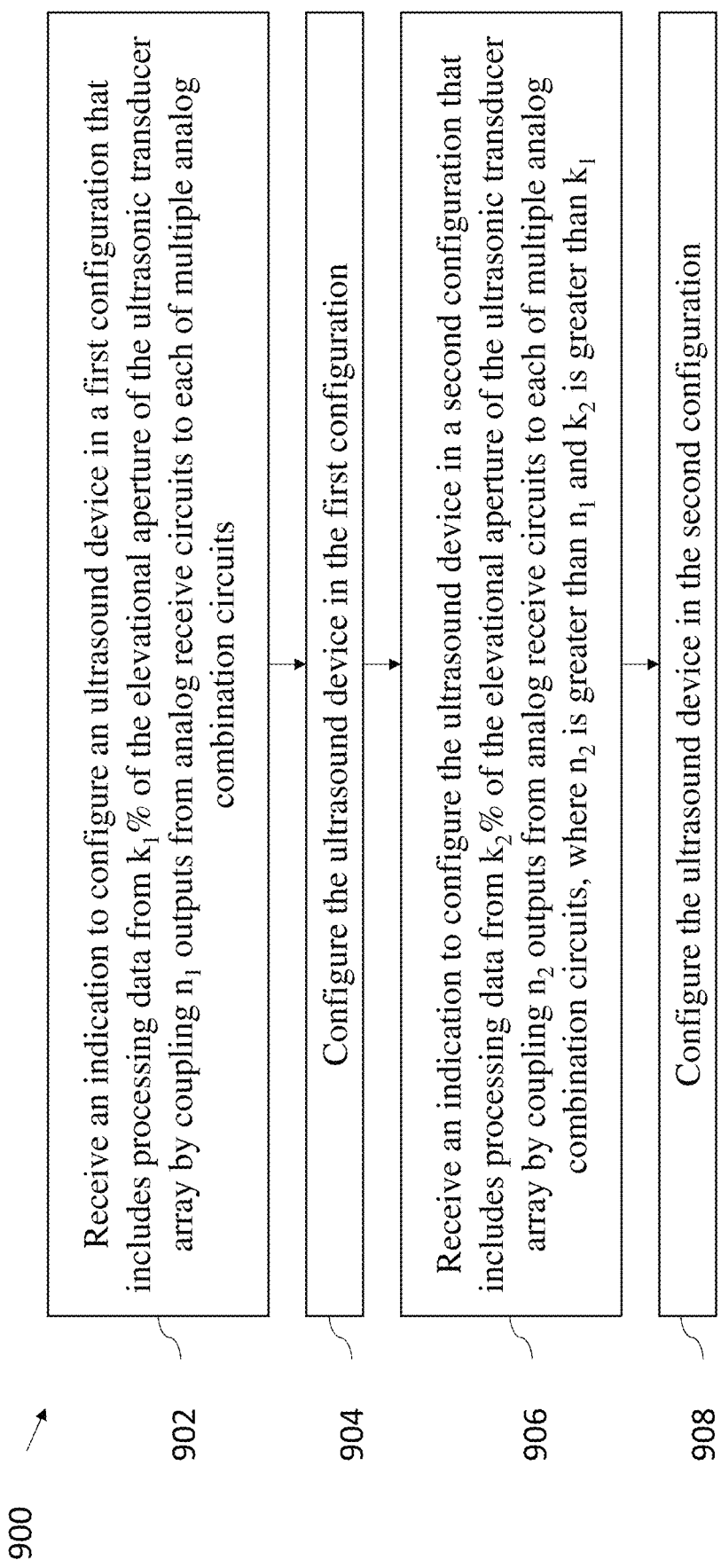
FIGS. 9 and 10 illustrate flow diagrams of processes for configuring circuitry in an ultrasound device, in accordance with certain embodiments described herein.
Figure 10:
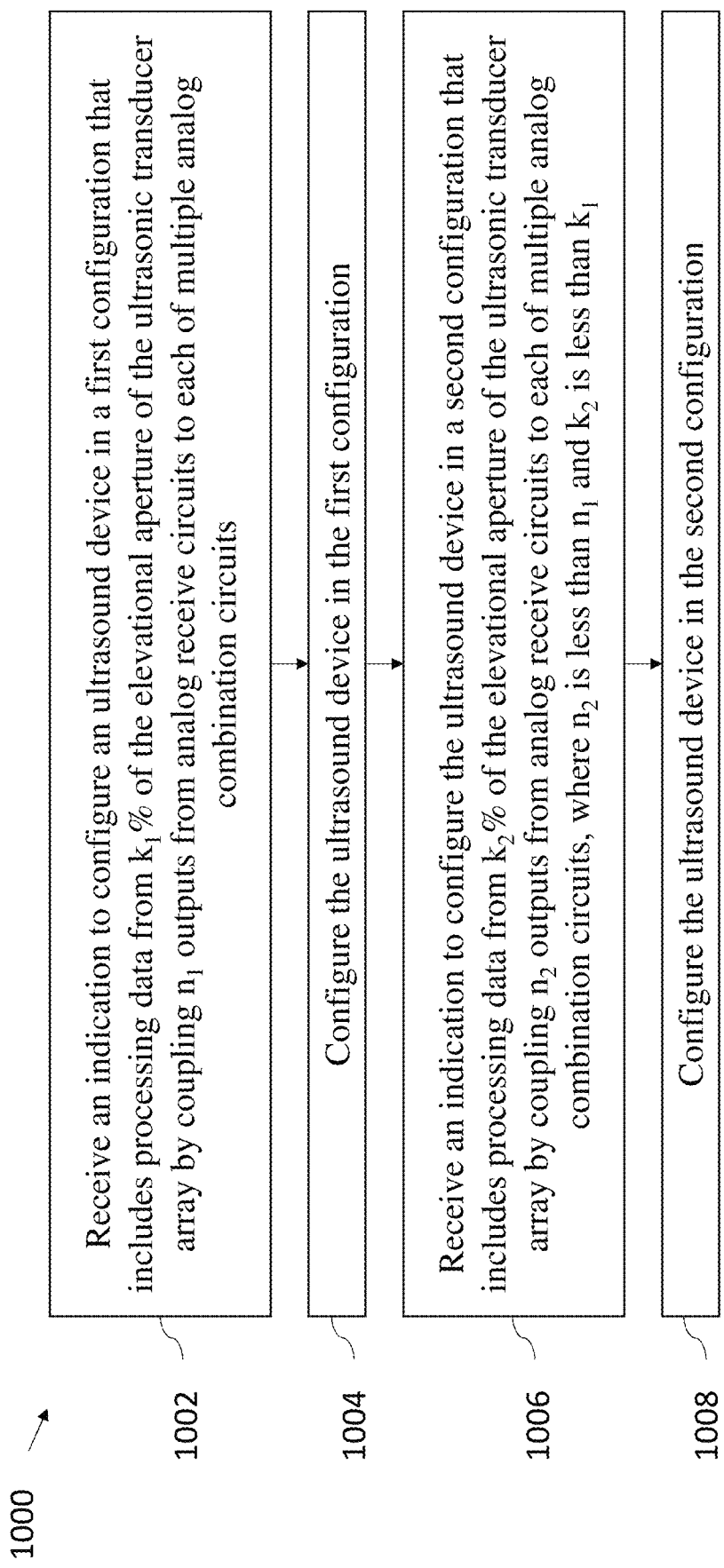

FIGS. 9 and 10 illustrate flow diagrams of processes 900 and 1000, respectively, for configuring circuitry in an ultrasound device, in accordance with certain embodiments described herein. In some embodiments, the processes 900 and 1000 may be performed using control circuitry (e.g., the control circuitry 418, 518, 1418, or 1518) that is configured to perform each of the acts of the processes 900 and 1000. In some embodiments, a processing device (e.g., a smartphone, tablet, or laptop) may be in operative communication with the ultrasound device. The processing device and the ultrasound device may communicate over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link. The processing device may be configured to transmit indications (e.g., control signals) to the control circuitry in the ultrasound device over the communication link to control the configuration. The circuitry in the ultrasound device described with reference to the processes 900 and 1000 may be integrated in a semiconductor chip (e.g., the semiconductor chip 100, or in some embodiments, in multiple semiconductor chips) in the ultrasound device. In the following description of the processes 900 and 1000, k and n (which may include subscripts) are all integer numbers.

Generally, the processes 900 and 1000 include configuring the ultrasound device in a first configuration that includes collecting ultrasound data with a certain portion of the elevational aperture and processing that ultrasound data with a certain resolution, and then switching to a second configuration that, in the process 900, includes collecting ultrasound data with a larger portion of the elevational aperture and processing that ultrasound data with a coarser resolution, or in the process 1000, includes collecting ultrasound data with a smaller portion of the elevational aperture and processing that ultrasound data with a finer resolution. The size of the elevational aperture may depend on how many output terminals from analog receive circuits (e.g., the analog receive circuits $404_1$-$404_{32}$ or $404_{1a}$-$404_{32b}$), in total, are coupled to analog combination circuits (e.g., the analog combination circuits $408_1$-$408_4$ or $408_{1a}$-$408_{4b}$), and thereby processed, and how many output terminals from analog receive circuits are not coupled to analog combination circuits, and thereby not processed. The resolution may depend on how many output terminals from analog receive circuits are coupled to each analog combination circuit. Control circuitry (e.g., the control circuitry 418, 518, 1418, and/or 1518) may control switching circuitry (e.g., the switching circuitry 406, 506, 1406, and/or 1506) to cause particular output terminals of the analog receive circuits to be coupled to particular analog combination circuits, thereby controlling both how many output terminals from analog receive circuits in total are coupled to analog combination circuits and how many output terminals from analog receive circuits are coupled to each analog combination circuit. The control circuitry may control the switching circuitry to do this by controlling the opening and closing of switches (e.g., the sets of switches $S_{1,1}$-$S_{32,4}$ or $S_{1a,1a}$-$S_{32b,4b}$) that switchably couple certain output terminals from the analog receive circuits to certain analog combination circuits.

In act 902 of the process 900, an indication is received to configure the ultrasound device in a first configuration. In the first configuration, the ultrasound device is configured to process data from $k_1$% of its the elevational aperture (e.g., the centermost $k_1$% of the elevational aperture of the ultrasound device) by coupling $n_1$ output terminals from analog receive circuits to each of multiple analog combination circuits. Further description of generating indications for configuring the ultrasound device may be found with reference to FIGS. 6-8B. An indication generated by a processing device in operative communication with the ultrasound device as described in FIGS. 6-8B may be transmitted to the ultrasound device from the processing device, and the indication received by the ultrasound device in act 902 may be the transmitted indication or an indication generated based on the transmitted indication. The indication received at act 902 may be the same as the control parameter config in FIGS. 4-5 or FIGS. 14-15. As described with reference to FIGS. 6-8B, the indication may be generated based on, and therefore the ultrasound device may receive the indication based on, a user selection of an anatomy for imaging, a user selection of an imaging depth, a power level of the ultrasound device, and/or a user selection of a power mode for the ultrasound device, as specific non-limiting examples, although the configuration indication may be generated based on other factors as well.

In act 904, the ultrasound device is configured in the first configuration. Control circuitry (e.g., the control circuitry 418, 518, 1418, and/or 1518) and switching circuitry (e.g., the switching circuitry 406, 506, 1406, and/or 1506) may facilitate configuration of the circuitry in the ultrasound device in the first configuration. Further description of how control circuitry and switching circuitry may configure an ultrasound device in different configurations may be found with reference to FIG. 5 or 15.

In act 906, an indication is received to configure the ultrasound device in a second configuration. In the second configuration, the ultrasound device is configured to process data from $k_2$% of its elevational aperture (e.g., the centermost $k_2$% of the elevational aperture of the ultrasound device) by coupling $n_2$ output terminals from analog receive circuits to each of multiple analog combination circuits. In this non-limiting example, $n_2$ is greater than $n_1$ and $k_2$ is greater than $k_1$. In other words, in the second configuration, the portion of the elevational aperture from which data is processed is larger than in the first configuration, but the resolution is coarser than in the first configuration. As specific non-limiting examples of n1 and n2, n1 may be 2 and n2 may be 4, n1 may be 2 and n2 may be 8, or n1 may be 4 and n2 may be 8. As specific non-limiting examples of k1% and k2%, k1% may be 25% and k2% may be 50%, k1% may be 25% and k2% may be 100%, or k1 may be 50% and k2 may be 100%. Further description of generating indications for configuring the ultrasound device may be found with reference to FIGS. 6-8B. An indication generated by a processing device in operative communication with the ultrasound device as described in FIGS. 6-8B may be transmitted to the ultrasound device from the processing device, and the indication received by the ultrasound device in act 906 may be the transmitted indication or an indication generated based on the transmitted indication. The indication received at act 906 may be the same as the control parameter config in FIG. 4-5 or 14-15. As described with reference to FIGS. 6-8B, the indication may be generated based on, and therefore the ultrasound device may receive the indication based on, a user selection of an anatomy for imaging, a user selection of an imaging depth, a power level of the ultrasound device, and/or a user selection of a power mode for the ultrasound device, as specific non-limiting examples, although the configuration indication may be generated based on other factors as well.

In act 908, the ultrasound device is configured in the second configuration. As described with reference to act 904, control circuitry (e.g., the control circuitry 418, 518, 1418, and/or 1518) and switching circuitry (e.g., the switching circuitry 406, 506, 1406, and/or 1506) may configure the circuitry in the ultrasound device in the first configuration. Further description of how control circuitry and switching circuitry may configure an ultrasound device in different configurations may be found with reference to FIG. 5 or 15.

Thus, as described above, acts 902 and 904 may include configuring the ultrasound device in a first configuration having a smaller elevational aperture and finer resolution and acts 906 and 908 may include configuring the ultrasound device in a second configuration having a larger elevational aperture and coarser resolution. As particular non-limiting examples for the process 900, applications where it may be helpful to reduce the size of the elevational aperture used may include imaging in the near field, imaging through the ribs (e.g., in cardiac ultrasound imaging, and especially pediatric cardiac ultrasound imaging), and/or when conserving power. Thus, as one example, the first configuration having a smaller elevational aperture may be associated with a first imaging depth, the second configuration having a larger elevational aperture may be associated with a second imaging depth that is deeper than the first depth, and the configuration may change from the first configuration to the second configuration when the imaging depth is increased. As another example, the first configuration having a smaller elevational aperture may be associated with imaging the heart, the second configuration having a larger elevational aperture may be associated with imaging another anatomical structure, region, or structure (e.g., the abdomen), and the configuration may change from the first configuration to the second configuration when a user selects to change from imaging the heart to imaging the other anatomical structure, region, or structure. As another example, the first configuration having a smaller elevational aperture may be associated with imaging when the ultrasound device is at a first power level, the second configuration having a larger elevational aperture may be associated with imaging when the ultrasound device is at a second power level that is greater than the first power level, and the configuration may change from the first configuration to the second configuration when the power level of the ultrasound device increases (e.g., when a battery of the ultrasound device is charged). As another example, the first configuration having a smaller elevational aperture may be associated with imaging when the ultrasound device is in a low power mode, the second configuration having a larger elevational aperture may be associated with imaging when the ultrasound device is in a non-low power mode (e.g., normal power mode), and the configuration may change from the first configuration to the second configuration when the user selects to change from low power mode to non-low power mode.

As particular non-limiting examples of configurations, the first configuration may be the 2×1 configuration described above and the second configuration may be the 4×1 configuration described above. As another example, the first configuration may be the 2×1 configuration described above and the second configuration may be the 8×1 configuration described above. As another example, the first configuration may be the 4×1 configuration described above and the second configuration may be the 8×1 configuration described above. As another example, the first configuration may be the 2×1 configuration described above and the second configuration may be the 4×2 configuration described above. As another example, the first configuration may be the 4×1 configuration described above and the second configuration may be the 4×2 configuration described above.

In act 1002 of the process 1000, an indication is received to configure the ultrasound device in a first configuration. In the first configuration, the ultrasound device is configured to process data from $k_1$% of its elevational aperture (e.g., the centermost $k_1$% of the elevational aperture of the ultrasound device) by coupling $n_1$ output terminals from analog receive circuits to each of multiple analog combination circuits. Further description of generating indications for configuring the ultrasound device may be found with reference to FIGS. 6-8B. An indication generated by a processing device in operative communication with the ultrasound device as described in FIGS. 6-8B may be transmitted to the ultrasound device from the processing device, and the indication received by the ultrasound device in act 1002 may be the transmitted indication or an indication generated based on the transmitted indication. The indication received at act 1002 may be the same as the control parameter config in FIG. 4-5 or 14-15. As described with reference to FIGS. 6-8B, the indication may be generated based on, and therefore the ultrasound device may receive the indication based on, a user selection of an anatomy for imaging, a user selection of an imaging depth, a power level of the ultrasound device, and/or a user selection of a power mode for the ultrasound device, as specific non-limiting examples, although the configuration indication may be generated based on other factors as well.

In act 1004, the ultrasound device is configured in the first configuration. Control circuitry (e.g., the control circuitry 418, 518, 1418, and/or 1518) and switching circuitry (e.g., the switching circuitry 406, 506, 1406, and/or 1506) may configure the circuitry in the ultrasound device in the first configuration. Further description of how control circuitry and switching circuitry may configure an ultrasound device in different configurations may be found with reference to FIG. 5 or 15.

In act 1006, an indication is received to configure the ultrasound device in a second configuration. In the second configuration, the ultrasound device is configured to process data from $k_2$% of its elevational aperture (e.g., the centermost $k_2$% of the elevational aperture of the ultrasound device) by coupling $n_2$ output terminals from analog receive circuits to each of multiple analog combination circuits, where $n_2$ is less than $n_1$ and $k_2$ is less than $k_1$. In other words, in the second configuration, the portion of the elevational aperture from which data is processed is smaller than in the first configuration, but the resolution is finer than in the first configuration. As specific non-limiting examples of n1 and n2, n1 may be 4 and n2 may be 2, n1 may be 8 and n2 may be 2, or n1 may be 8 and n2 may be 4. As specific non-limiting examples of k1% and k2%, k1% may be 50% and k2% may be 25%, k1% may be 100% and k2% may be 25%, or k1 may be 100% and k2 may be 50%. Further description of generating indications for configuring the ultrasound device may be found with reference to FIGS. 6-8B. An indication generated by a processing device in operative communication with the ultrasound device as described in FIGS. 6-8B may be transmitted to the ultrasound device from the processing device, and the indication received by the ultrasound device in act 1006 may be the transmitted indication or an indication generated based on the transmitted indication. The indication received at act 1006 may be the same as the control parameter config in FIG. 4-5 or 14-15. As described with reference to FIGS. 6-8B, the indication may be generated based on, and therefore the ultrasound device may receive the indication based on, a user selection of an anatomy for imaging, a user selection of an imaging depth, a power level of the ultrasound device, and/or a user selection of a power mode for the ultrasound device, as specific non-limiting examples, although the configuration indication may be generated based on other factors as well.

In act 1008, the ultrasound device is configured in the second configuration. As described with reference to act 1004, control circuitry (e.g., the control circuitry 418, 518, 1418, and/or 1518) and switching circuitry (e.g., the switching circuitry 406, 506, 1406, and/or 1506) may configure the circuitry in the ultrasound device in the first configuration. Further description of how control circuitry and switching circuitry may configure an ultrasound device in different configurations may be found with reference to FIG. 5 or 15.

Thus, as described above, acts 1002 and 1004 may include configuring the ultrasound device in a first configuration having a larger elevational aperture and coarser resolution and acts 906 and 908 may include configuring the ultrasound device in a second configuration having a smaller elevational aperture and finer resolution. As particular non-limiting examples for the process 1000, applications where it may be helpful to reduce the size of the elevational aperture used may include imaging in the near field, imaging through the ribs (e.g., in cardiac ultrasound imaging), and/or when conserving power. Thus, as one example, the first configuration having a larger elevational aperture may be associated with a first imaging depth, the second configuration having a smaller elevational aperture may be associated with a second imaging depth that is shallower than the first imaging depth, and the configuration may change from the first configuration to the second configuration when the imaging depth is decreased. As another example, the first configuration having a larger elevational aperture may be associated with imaging a particular anatomical structure, region, or structure (e.g., the abdomen), the second configuration having a smaller elevational aperture may be associated with imaging the heart, and the configuration may change from the first configuration to the second configuration when a user selects to change from imaging the other anatomical structure, region, or structure to imaging the heart. As another example, the first configuration having a larger elevational aperture may be associated with imaging when the ultrasound device is at a first power level, the second configuration having a smaller elevational aperture may be associated with imaging when the ultrasound device is at a second power level that is less than the first power level, and the configuration may change from the first configuration to the second configuration when the power level of the ultrasound device decreases (e.g., when a battery of the ultrasound device is drained). As another example, the first configuration having a larger elevational aperture may be associated with imaging when the ultrasound device is in a non-low power mode (e.g., a normal power mode), the second configuration having a smaller elevational aperture may be associated with imaging when the ultrasound device is in a low power mode, and the configuration may change from the first configuration to the second configuration when the user selects to change from non-low power mode to low power mode. As particular non-limiting examples of configurations, the first configuration may be the 4×1 configuration described above and the second configuration may be the 2×1 configuration described above. As another example, the first configuration may be the 8×1 configuration described above and the second configuration may be the 2×1 configuration described above. As another example, the first configuration may be the 8×1 configuration described above and the second configuration may be the 4×1 configuration described above. As another example, the first configuration may be the 4×2 configuration described above and the second configuration may be the 4×1 configuration described above. As another example, the first configuration may be the 4×2 configuration described above and the second configuration may be the 2×1 configuration described above.

The ultrasound device may be capable of performing both the process 900 and the process 1000. Consider that the ultrasound device is configured in a particular configuration that includes processing data from a certain portion of the elevational aperture of the ultrasound device by coupling a certain number of output terminals from analog receive circuits to each of multiple analog combination circuits. If the ultrasound device receives an indication to change to a configuration that includes processing data from a larger portion of the elevational aperture of the ultrasound device by coupling more output terminals from analog receive circuits to each of the multiple analog combination circuits, then the ultrasound device may do so (the process 900). If the ultrasound device receives an indication to change to a different configuration that includes processing data from a smaller portion of the elevational aperture of the ultrasound device by coupling fewer output terminals from analog receive circuits to each of the multiple analog combination circuits, then the ultrasound device may do so (the process 1000).

In some embodiments, acts 902 and 904 and/or acts 1002 and 1004 may be absent, such as if the ultrasound device is configured in the first configuration by default.

Each of the processes 900 and 1000 may correspond to two iterations through the processes 600, 700, 800A, and/or 800B. In the first iteration, the processing device may receive a first anatomy for imaging (act 602), receive a first imaging depth (act 702), determine a first power level of the ultrasound device (act 802A), or receive a selection of a first power mode (act 802B). At acts 604, 704, 804A, and 804B, the processing device may generate a first configuration indication associated with the first anatomy, the first imaging depth, the first power level, or the first power mode, where the first configuration indication is associated with a first configuration that includes collecting ultrasound data with a first portion of the elevational aperture of the ultrasound device and processing that ultrasound data by the ultrasound device with a first resolution. In the second iteration, the processing device may receive a second anatomy for imaging (act 602), receive a second imaging depth (act 702), determine a second power level of the ultrasound device (act 802A), or receive a selection of a second power mode (act 802B). At acts 604, 704, 804A, and 804B, the processing device may generate a second configuration indication associated with the second anatomy, the second imaging depth, the second power level, or the second power mode, where the second configuration indication is associated with a second configuration that includes collecting ultrasound data with a second portion of the elevational aperture of the ultrasound device and processing that ultrasound data by the ultrasound device with a second resolution. The second portion of the elevational aperture may be larger than the first portion of the elevational aperture and the second resolution may be coarser than the first resolution. In this case, the first configuration indication may be the indication received in act 902 and the second configuration indication may be the indication received in act 906. Alternatively, the first portion of the elevational aperture may be larger than the second portion of the elevational aperture and the first resolution may be coarser than the second resolution. In this case, the first configuration indication may be the indication received in act 1002 and the second configuration indication may be the indication received in act 1006.

While the above description has focused on configurations that include using the centermost k % of the elevational aperture of an ultrasound device, it should be appreciated that the circuits and methods described herein may be modified to enable configurations that include using other continuous portions of the elevational aperture, such as the topmost, bottommost, rightmost, or leftmost k % of the elevational aperture.

Figure 11:
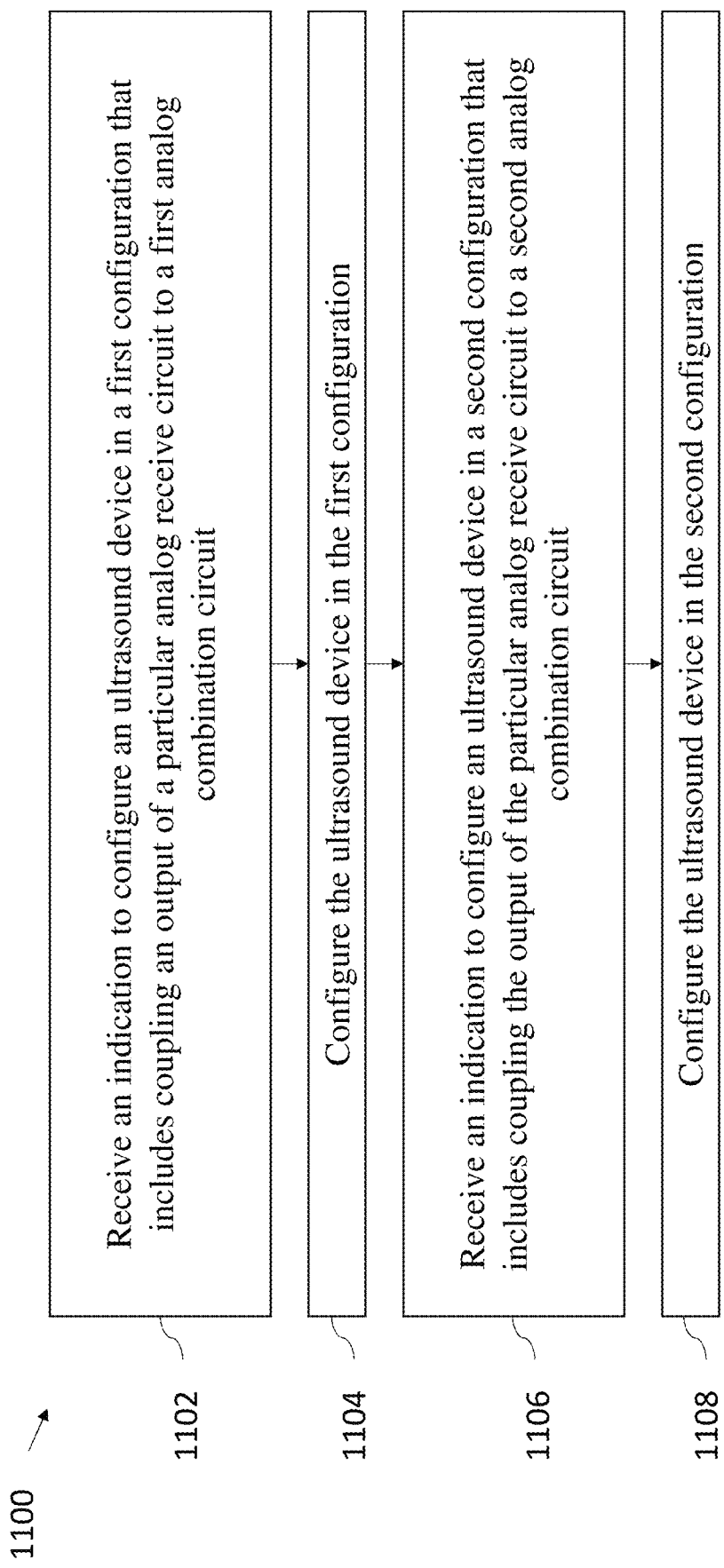
FIG. 11 illustrates a flow diagram of a process for configuring circuitry in an ultrasound device, in accordance with certain embodiments described herein.

FIG. 11 illustrates a flow diagram of a process 1100 for configuring circuitry in an ultrasound device, in accordance with certain embodiments described herein. In some embodiments, the process 1100 may be performed using control circuitry (e.g., the control circuitry 418, 518, 1418, or 1518) that is configured to perform each of the acts of the process 1100. In some embodiments, a processing device (e.g., a smartphone, tablet, or laptop) may be in operative communication with the ultrasound device. The processing device and the ultrasound device may communicate over a wired (e.g., through an Ethernet cable, a Universal Serial Bus (USB) cable, or a Lightning cable) and/or wireless (e.g., using BLUETOOTH, ZIGBEE, and/or WiFi wireless protocols) communication link. The processing device may be configured to transmit indications (e.g., control signals) to the control circuitry in the ultrasound device over the communication link to control the configuration. The circuitry in the ultrasound device described with reference to the process 1100 may be integrated in a semiconductor chip (e.g., the semiconductor chip 100, or in some embodiments, in multiple semiconductor chips) in the ultrasound device.

Generally, the process 1100 includes configuring the ultrasound device in a first configuration and a second configuration, where processing of ultrasound data in the different configurations may be performed at different resolutions. The resolution may depend on how many output terminals from analog receive circuits (e.g., the analog receive circuits $404_1$-$404_{32}$ or $404_{1a}$-$404_{32b}$) are coupled to each analog combination circuit (e.g., each of the analog combination circuits $408_1$-$408_4$ or $408_{1a}$-$408_{4b}$). Control circuitry (e.g., the control circuitry 418, 518, 1418, and/or 1518) may control switching circuitry (e.g., the switching circuitry 406, 506, 1406, and/or 1506) to cause particular output terminals of the analog receive circuits to be coupled to particular analog combination circuits. The control circuitry may control the switching circuitry to do this by controlling the opening and closing of switches (e.g., the sets of switches $S_{1,1}$-$S_{32,4}$ or $S_{1a,1a}$-$S_{32b,4b}$) that switchably couple certain output terminals from the analog receive circuits to certain analog combination circuits. Varying the resolution may include coupling a particular output terminal of an analog receive circuit to one of the analog combination circuits in the first configuration and coupling that same output terminal of the analog receive circuit to a different analog combination circuit in the second configuration. Further description of this may be found with reference to FIG. 5 or 15.

In act 1102 of the process 1100, an indication is received to configure the ultrasound device in a first configuration that includes coupling an output terminal of a particular analog receive circuit to a first analog combination circuit. Further description of generating indications for configuring the ultrasound device may be found with reference to FIGS. 6-8B. An indication generated by a processing device in operative communication with the ultrasound device as described in FIGS. 6-8B may be transmitted to the ultrasound device from the processing device, and the indication received by the ultrasound device in act 1102 may be the transmitted indication or an indication generated based on the transmitted indication. The indication received at act 1102 may be the same as the control parameter config in FIG. 4-5 or 14-15. As described with reference to FIGS. 6-8B, the indication may be generated based on, and therefore the ultrasound device may receive the indication based on, a user selection of an anatomy for imaging, a user selection of an imaging depth, a power level of the ultrasound device, and/or a user selection of a power mode for the ultrasound device, as specific non-limiting examples, although the configuration indication may be generated based on other factors as well. As a non-limiting example, consider that the output terminal of the particular analog receive circuit is $analog_8$ of FIG. 5. If the first configuration is 8×1, then analog$_8$ may be coupled to the analog combination circuit 408$_1$. Further description of this may be found with reference to FIG. 5.

In act 1104, the ultrasound device is configured in the first configuration. Control circuitry (e.g., the control circuitry 418, 518, 1418, and/or 1518) and switching circuitry (e.g., the switching circuitry 406, 506, 1406, and/or 1506) may configure the circuitry in the ultrasound device in the first configuration. Further description of how control circuitry and switching circuitry may configure an ultrasound device in different configurations may be found with reference to FIG. 5 or 15.

In act 1106, an indication is received to configure the ultrasound device in a second configuration that couples the output terminal of the particular analog receive circuit (i.e., the same output terminal described above with reference to act 1102) to a second analog combination circuit (i.e., different from the first analog combination circuit described above). Further description of generating indications for configuring the ultrasound device may be found with reference to FIGS. 6-8B. An indication generated by a processing device in operative communication with the ultrasound device as described in FIGS. 6-8B may be transmitted to the ultrasound device from the processing device, and the indication received by the ultrasound device in act 906 may be the transmitted indication or an indication generated based on the transmitted indication. The indication received at act 1106 may be the same as the control parameter config in FIG. 4-5 or 14-15. As described with reference to FIGS. 6-8B, the indication may be generated based on, and therefore the ultrasound device may receive the indication based on, a user selection of an anatomy for imaging, a user selection of an imaging depth, a power level of the ultrasound device, and/or a user selection of a power mode for the ultrasound device, as specific non-limiting examples, although the configuration indication may be generated based on other factors as well. Continuing the example above of analog$_8$ of FIG. 5, if the second configuration is 4×1, then analog$_8$ may be coupled to the analog combination circuit 408$_2$ (different from 408$_1$, to which analog$_8$ was coupled in the first configuration as described above). Further description of this may be found with reference to FIG. 5.

In act 1108, the ultrasound device is configured in the second configuration. As described with reference to act 1104, control circuitry (e.g., the control circuitry 418, 518, 1418, and/or 1518) and switching circuitry (e.g., the switching circuitry 406, 506, 1406, and/or 1506) may configure the circuitry in the ultrasound device in the first configuration. Further description of how control circuitry and switching circuitry may configure an ultrasound device in different configurations may be found with reference to FIG. 5 or 15.

It should be appreciated that act 1102 may be the same as acts 902 and/or 1002, act 1104 may be the same as acts 904 and/or 1004, act 1106 may be the same as acts 906 and/or 1006, and act 1108 may be the same as acts 908 and/or 1008. In other words, the first configuration and second configuration may be same as the first configuration and second configuration, respectively, described above with reference to the processes 900 and 1000, and any or all of the description of the processes 900 and 1000 may apply to the process 1100 as well. It should also be appreciated that more than one output terminals of analog receive circuits may be coupled to different analog combination circuits in one configuration versus another.

Figure 12:
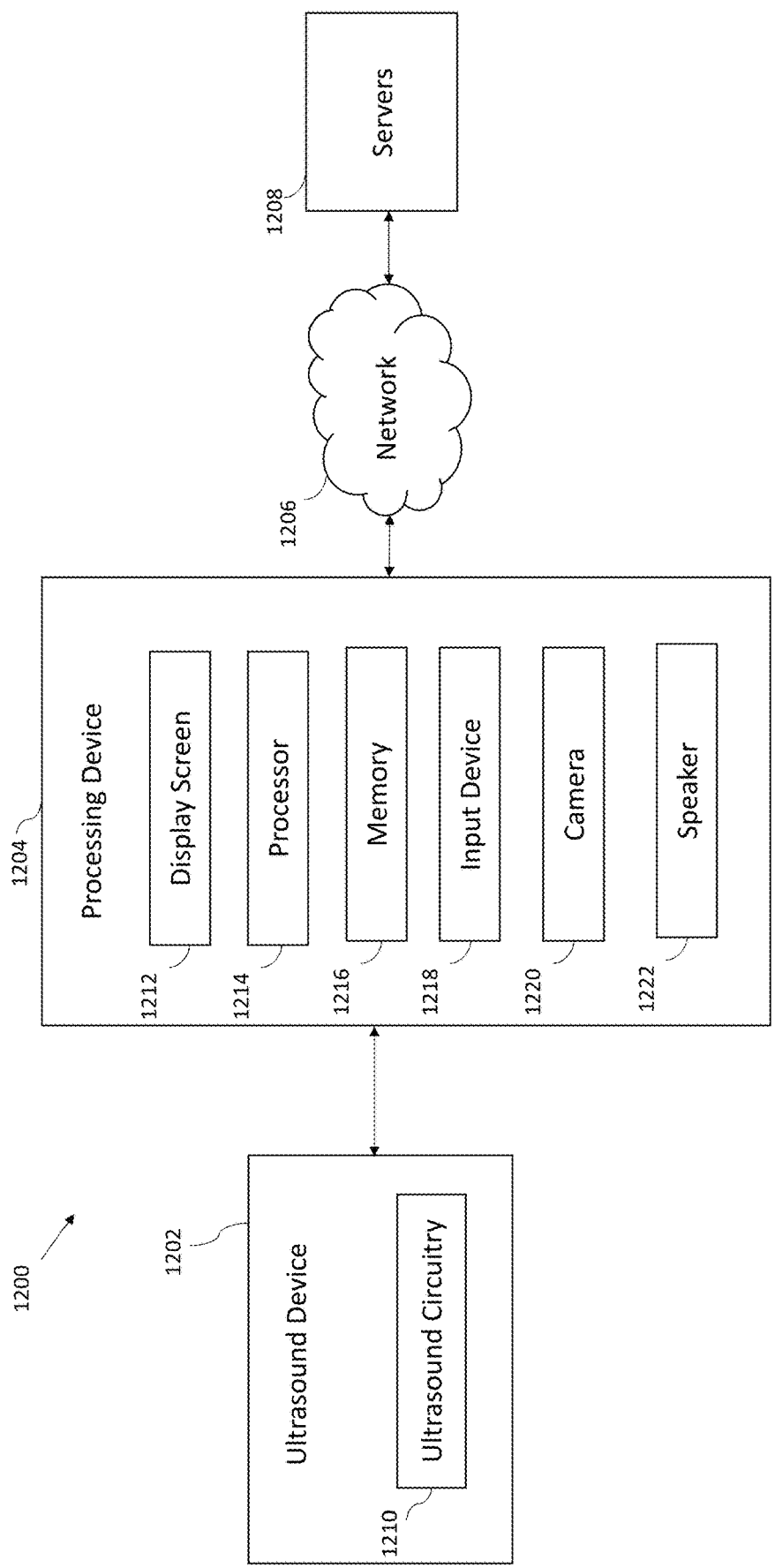
FIG. 12 illustrates a schematic block diagram of an example ultrasound system upon which various aspects of the technology described herein may be practiced.

FIG. 12 illustrates a schematic block diagram of an example ultrasound system 1200 upon which various aspects of the technology described herein may be practiced. The ultrasound system 1200 includes an ultrasound device 1202, a processing device 1204, a network 1206, and one or more servers 1208. The processing device 1204 may be any of the processing devices described herein. The ultrasound device 1202 may be any of the ultrasound devices described herein.

The ultrasound device 1202 includes ultrasound circuitry 1210. The processing device 1204 includes a camera 1220, a display screen 1212, a processor 1214, a memory 1216, an input device 1218, and a speaker 1222. The processing device 1204 is in wired (e.g., through a lightning connector or a mini-USB connector) and/or wireless communication (e.g., using BLUETOOTH, ZIGBEE, and/or WiFi wireless protocols) with the ultrasound device 1202. The processing device 1204 is in wireless communication with the one or more servers 1208 over the network 1206.

The ultrasound device 1202 may be configured to generate ultrasound data that may be employed to generate an ultrasound image. The ultrasound device 1202 may be constructed in any of a variety of ways. In some embodiments, the ultrasound device 1202 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 1210 may be configured to generate the ultrasound data, and may include any of the ultrasound circuitry described herein (e.g., the analog receive circuits 404, the switching circuitry 406, 506, 1406, and/or 1506, the analog combination circuits 408, the ADCs 410, and the control circuitry 418, 1518, 1418, and/or 1518). Control circuitry in the ultrasound circuitry 1210 may be configured to perform the processes 900, 1000, and 1100. The ultrasound circuitry 1210 may also include one or more ultrasonic transducers (e.g., the ultrasonic transducers 102) monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 1210 (e.g., the analog receive circuits 404, the switching circuitry 406, 506, 1406, and/or 1506, the analog combination circuits 408, the ADCs 410, and the control circuitry 418, 1518, 1418, and/or 1518) to form a monolithic ultrasound device. The ultrasound device 1202 may transmit ultrasound data and/or ultrasound images to the processing device 1204 over a wired (e.g., through a lightning connector or a mini-USB connector) and/or wireless (e.g., using BLUETOOTH, ZIGBEE, and/or WiFi wireless protocols) communication link.

Referring now to the processing device 1204, the processor 1214 may include specially-programmed and/or special-purpose hardware such as an application-specific integrated circuit (ASIC). For example, the processor 1214 may include one or more graphics processing units (GPUs) and/or one or more tensor processing units (TPUs). TPUs may be ASICs specifically designed for machine learning (e.g., deep learning). The TPUs may be employed, for example, to accelerate the inference phase of a neural network. The processing device 1204 may be configured to process the ultrasound data received from the ultrasound device 1202 to generate ultrasound images for display on the display screen 1212. The processing may be performed by, for example, the processor 1214. The processor 1214 may also be adapted to control the acquisition of ultrasound data with the ultrasound device 1202. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data may be sequentially displayed. Additionally, or alternatively, the ultrasound data may be stored temporarily in a buffer during a scanning session and processed in less than real-time.

The processing device 1204 may be configured to perform certain of the processes (e.g., the processes 600-800B) described herein using the processor 1214 (e.g., control circuitry in the processor 1214) and one or more articles of manufacture that include non-transitory computer-readable storage media such as the memory 1216. The processor 1214 may control writing data to and reading data from the memory 1216 in any suitable manner. To perform certain of the processes described herein, the processor 1214 may execute one or more processor-executable instructions stored in one or more non-transitory computer-readable storage media (e.g., the memory 1216), which may serve as non-transitory computer-readable storage media storing processor-executable instructions for execution by the processor 1214. The camera 1220 may be configured to detect light (e.g., visible light) to form an image. The camera 1220 may be on the same face of the processing device 1204 as the display screen 1212. The display screen 1212 may be configured to display images and/or videos, and may be, for example, a liquid crystal display (LCD), a plasma display, and/or an organic light emitting diode (OLED) display on the processing device 1204. The input device 1218 may include one or more devices capable of receiving input from a user and transmitting the input to the processor 1214. For example, the input device 1218 may include a keyboard, a mouse, a microphone, touch-enabled sensors on the display screen 1212, and/or a microphone. The display screen 1212, the input device 1218, the camera 1220, and the speaker 1222 may be communicatively coupled to the processor 1214 and/or under the control of the processor 1214.

It should be appreciated that the processing device 1204 may be implemented in any of a variety of ways. For example, the processing device 1204 may be implemented as a handheld device such as a mobile smartphone or a tablet. Thereby, a user of the ultrasound device 1202 may be able to operate the ultrasound device 1202 with one hand and hold the processing device 1204 with another hand. In other examples, the processing device 1204 may be implemented as a portable device that is not a handheld device, such as a laptop. In yet other examples, the processing device 1204 may be implemented as a stationary device such as a desktop computer. The processing device 1204 may be connected to the network 1206 over a wired connection (e.g., via an Ethernet cable) and/or a wireless connection (e.g., over a WiFi network). The processing device 1204 may thereby communicate with (e.g., transmit data to or receive data from) the one or more servers 1208 over the network 1206. For example, a party may provide from the server 1208 to the processing device 1204 processor-executable instructions for storing in one or more non-transitory computer-readable storage media (e.g., the memory 1216) which, when executed, may cause the processing device 1204 to perform certain of the processes (e.g., the processes 600-800B) described herein.

According to an aspect of the present disclosure, there is provided an ultrasound device, comprising an ultrasonic transducer array and control circuitry configured to receive a first indication to configure the ultrasound device in a first configuration that includes processing data from k1% of an elevational aperture of the ultrasonic transducer array by coupling n1 output terminals from analog receive circuits to each of multiple analog combination circuits, configure the ultrasound device in the first configuration, receive a second indication to configure the ultrasound device in a second configuration that includes processing data from k2% of the elevational aperture of the ultrasonic transducer array by coupling n2 output terminals from analog receive circuits to each of multiple analog combination circuits, wherein n2 is greater than n1 and k2 is greater than k1 or n2 is less than n1 and k2 is less than k1, and configure the ultrasound device in the second configuration.

In some embodiments, the ultrasound device further comprises a plurality of ultrasonic transducers, a plurality of analog receive circuits each configured to receive and/or process an analog ultrasound signal from one or more corresponding ultrasonic transducers of the plurality of ultrasonic transducers, a plurality of analog combination circuits each configured to output a single analog output by combining multiple analog inputs, and switching circuitry comprising a plurality of switches each switchably coupling an output of a particular analog receive circuit of the plurality of analog receive circuits to an input of a particular analog combination circuit of the plurality of analog combination circuits. The control circuitry is configured, when configuring the ultrasound device in the first and/or second configurations, to control the switching circuitry to cause particular outputs of the plurality of analog receive circuits to be coupled as inputs to particular analog combination circuits of the plurality of analog combination circuits and an output of a first analog receive circuit of the plurality of analog receive circuits is switchably coupled to inputs of multiple but not all analog combination circuits of the plurality of analog combination circuits.

In some embodiments, outputs of fewer than 75% of the plurality of analog receive circuits are switchably coupled to inputs of all analog combination circuits of the plurality of analog combination circuits.

In some embodiments, the output of the first analog receive circuit of the plurality of analog receive circuits is switchably coupled to inputs of a first number of analog combination circuits of the plurality of analog combination circuits, an output of a second analog receive circuit of the plurality of analog receive circuits is switchably coupled to inputs of a second number of analog combination circuits of the plurality of analog combination circuits, and the first and second numbers are different.

In some embodiments, the analog receive circuits comprise analog amplification circuitry analog filtering circuitry, analog polarity conversion circuitry, analog compression circuitry, analog expansion circuitry, analog beamforming circuitry, analog dechirp circuitry, analog quadrature demodulation circuitry, analog time delay circuitry, analog phase shifter circuitry and/or analog time gain compensation circuitry.

In some embodiments, the analog combination circuits comprise averaging circuitry.

In some embodiments, the analog receive circuits, the analog combination circuits, the switching circuitry, and the control circuitry are integrated in a semiconductor chip.

In some embodiments, the k1% of the elevational aperture of the ultrasonic transducer array comprises a centermost k1% of the elevational aperture of the ultrasonic transducer array.

In some embodiments, when k2 is less than k1: k1 is 100 and k2 is 50, k1 is 100 and k2 is 25, or k1 is 50 and k2 is 25 and when k2 is greater than k1: k1 is 50 and k2 is 100, k1 is 25 and k2 is 100, or k1 is 25 and k2 is 50.

In some embodiments, when n2 is less than n1: n1 is 8 and n2 is 4, n1 is 8 and n2 is 2, or n1 is 4 and n2 is 2 and when n2 is greater than n1: n1 is 4 and n2 is 8, n1 is 2 and n2 is 8, or n1 is 2 and n2 is 4.

In some embodiments, the control circuitry is configured, when receiving the indication to configure the ultrasound device in the first configuration, to receive the indication based on a user selection of an anatomy for imaging.

In some embodiments, the control circuitry is configured, when receiving the indication to configure the ultrasound device in the first configuration, to receive the indication based on a user selection of an imaging depth.

In some embodiments, the control circuitry is configured, when receiving the indication to configure the ultrasound device in the first configuration, to receive the indication based on a power level of the ultrasound device.

In some embodiments, the control circuitry is configured, when receiving the indication to configure the ultrasound device in the first configuration, to receive the indication based on a user selection of a power mode for the ultrasound device.

In some embodiments, the first configuration is a configuration associated with imaging a heart and n2 is greater than n1 and k2 is greater than k1.

In some embodiments, the second configuration is a configuration associated with imaging an abdomen.

In some embodiments, the first configuration is a configuration associated with imaging at a first imaging depth, the second configuration is a configuration associated with imaging at a second imaging depth, the first imaging depth is deeper than the second imaging depth, and n2 is less than n1 and k2 is less than k1.

In some embodiments, the first configuration is a configuration associated with imaging at a first power level of the ultrasound device, the second configuration is a configuration associated with imaging at a second power level of the ultrasound device, the first power level is greater than the power level, and n2 is less than n1 and k2 is less than k1.

In some embodiments, the first configuration is a configuration associated with imaging in a non-low power mode of the ultrasound device, the second configuration is a configuration associated with imaging at a low power mode of the ultrasound device, and n2 is less than n1 and k2 is less than k1.

According to an aspect of the present disclosure, there is provided an ultrasound device, comprising a plurality of ultrasonic transducers, a plurality of analog receive circuits each configured to receive and/or process an analog ultrasound signal from one or more corresponding ultrasonic transducers of the plurality of ultrasonic transducers, a plurality of analog combination circuits each configured to output a single analog output by combining multiple analog inputs, and switching circuitry comprising a plurality of switches each switchably coupling an output of a particular analog receive circuit of the plurality of analog receive circuits to an input of a particular analog combination circuit of the plurality of analog combination circuits. The control circuitry is configured, when configuring the ultrasound device in the first and/or second configurations, to control the switching circuitry to cause particular outputs of the plurality of analog receive circuits to be coupled as inputs to particular analog combination circuits of the plurality of analog combination circuits and an output of a first analog receive circuit of the plurality of analog receive circuits is switchably coupled to inputs of multiple but not all analog combination circuits of the plurality of analog combination circuits.

In some embodiments, outputs of fewer than 75% of the plurality of analog receive circuits are switchably coupled to inputs of all analog combination circuits of the plurality of analog combination circuits.

In some embodiments, the output of the first analog receive circuit of the plurality of analog receive circuits is switchably coupled to inputs of a first number of analog combination circuits of the plurality of analog combination circuits, an output of a second analog receive circuit of the plurality of analog receive circuits is switchably coupled to inputs of a second number of analog combination circuits of the plurality of analog combination circuits, and the first and second numbers are different.

In some embodiments, the analog receive circuits comprise analog amplification circuitry analog filtering circuitry, analog polarity conversion circuitry, analog compression circuitry, analog expansion circuitry, analog beamforming circuitry, analog dechirp circuitry, analog quadrature demodulation circuitry, analog time delay circuitry, analog phase shifter circuitry and/or analog time gain compensation circuitry.

In some embodiments, the analog combination circuits comprise averaging circuits.

In some embodiments, the analog receive circuits, the analog combination circuits, the switching circuitry, and the control circuitry are integrated in a semiconductor chip.

According to an aspect of the present disclosure, there is provided an ultrasound device, comprising a plurality of ultrasonic transducers, a plurality of analog receive circuits each configured to receive and/or process an analog ultrasound signal from one or more corresponding ultrasonic transducers of the plurality of ultrasonic transducers, a plurality of analog combination circuits each configured to output a single analog output by combining multiple analog inputs, switching circuitry comprising a plurality of switches each switchably coupling an output of a particular analog receive circuit to an input of a particular analog combination circuit, and control circuitry configured to receive a first indication to configure an ultrasound device in a first configuration that includes coupling an output of a particular analog receive circuit of the plurality of analog receive circuits to a first analog combination circuit of the plurality of analog combination circuit, configure the ultrasound device in the first configuration, receive a second indication to configure an ultrasound device in a second configuration that includes coupling the output of the particular analog receive circuit of the plurality of analog receive circuits to a second analog combination circuit of the plurality of analog combination circuit, wherein the first and second analog combination circuits are different, and configure the ultrasound device in the second configuration.

In some embodiments, an output of a first analog receive circuit of the plurality of analog receive circuits is switchably coupled to inputs of multiple but not all analog combination circuits of the plurality of analog combination circuits.

In some embodiments, outputs of fewer than 75% of the plurality of analog receive circuits are switchably coupled to inputs of all analog combination circuits of the plurality of analog combination circuits.

In some embodiments, the output of the first analog receive circuit of the plurality of analog receive circuits is switchably coupled to inputs of a first number of analog combination circuits of the plurality of analog combination circuits, an output of a second analog receive circuit of the plurality of analog receive circuits is switchably coupled to inputs of a second number of analog combination circuits of the plurality of analog combination circuits, and the first and second numbers are different.

In some embodiments, the analog receive circuits comprise analog amplification circuitry analog filtering circuitry, analog polarity conversion circuitry, analog compression circuitry, analog expansion circuitry, analog beamforming circuitry, analog dechirp circuitry, analog quadrature demodulation circuitry, analog time delay circuitry, analog phase shifter circuitry and/or analog time gain compensation circuitry.

In some embodiments, the analog combination circuits comprise averaging circuits.

In some embodiments, the switching circuitry comprises a plurality of switches each switchably coupling an output of a particular analog receive circuits to an input of a particular analog combination circuit.

In some embodiments, the analog receive circuits, the analog combination circuits, the switching circuitry, and the control circuitry are integrated in a semiconductor chip.

In some embodiments, the control circuitry is configured, when receiving the indication to configure the ultrasound device in the first configuration, to receive the indication based on a user selection of an anatomy for imaging.

In some embodiments, the control circuitry is configured, when receiving the indication to configure the ultrasound device in the first configuration, to receive the indication based on a user selection of an imaging depth.

In some embodiments, the control circuitry is configured, when receiving the indication to configure the ultrasound device in the first configuration, to receive the indication based on a power level of the ultrasound device.

In some embodiments, the control circuitry is configured, when receiving the indication to configure the ultrasound device in the first configuration, to receive the indication based on a user selection of a power mode for the ultrasound device.

According to an aspect of the present disclosure, there is provided a processing device in operative communication with an ultrasound device, the processing device configured to receive a selection of a first anatomy for imaging and generate a first configuration indication associated with the first anatomy, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

In some embodiments, the processing device is further configured to receive a selection of a second anatomy for imaging and generate a second configuration indication associated with the second anatomy, wherein the second configuration indication is associated with a second configuration that includes collecting ultrasound data with a second portion of the elevational aperture of the ultrasonic transducer array and processing that ultrasound data by the ultrasound device with a second resolution. The first portion of the elevational aperture is larger than the second portion of the elevational aperture and the first resolution is coarser than the second resolution or the second portion of the elevational aperture is larger than the first portion of the elevational aperture and the second resolution is coarser than the first resolution.

In some embodiments, the first anatomy is a heart, the second portion of the elevational aperture is larger than the first portion of the elevational aperture, and the second resolution is coarser than the first resolution.

In some embodiments, the second anatomy is an abdomen.

According to an aspect of the present disclosure, there is provided a processing device in operative communication with an ultrasound device, the processing device configured to receive a selection of a first imaging depth and generate a first configuration indication associated with the first imaging depth, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

In some embodiments, the processing device is further configured to receive a selection of a second imaging depth and generate a second configuration indication associated with the second imaging depth, wherein the second configuration indication is associated with a second configuration that includes collecting ultrasound data with a second portion of the elevational aperture of the ultrasonic transducer array and processing that ultrasound data by the ultrasound device with a second resolution. The first portion of the elevational aperture is larger than the second portion of the elevational aperture and the first resolution is coarser than the second resolution or the second portion of the elevational aperture is larger than the first portion of the elevational aperture and the second resolution is coarser than the first resolution.

In some embodiments, the first imaging depth is deeper than the second imaging depth, the second portion of the elevational aperture is larger than the first portion of the elevational aperture, and the second resolution is coarser than the first resolution.

According to an aspect of the present disclosure, there is provided a processing device in operative communication with an ultrasound device, the processing device configured to determine a first power level of the ultrasound device and generate a first configuration indication associated with the first power level, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

In some embodiments, the processing device is further configured to determine a second power level of the ultrasound device and generate a second configuration indication associated with the second power level, wherein the second configuration indication is associated with a second configuration that includes collecting ultrasound data with a second portion of the elevational aperture of the ultrasonic transducer array and processing that ultrasound data by the ultrasound device with a second resolution. The first portion of the elevational aperture is larger than the second portion of the elevational aperture and the first resolution is coarser than the second resolution or the second portion of the elevational aperture is larger than the first portion of the elevational aperture and the second resolution is coarser than the first resolution.

In some embodiments, the first power level is less than the first power level, the second portion of the elevational aperture is larger than the first portion of the elevational aperture, and the second resolution is coarser than the first resolution.

According to an aspect of the present disclosure, there is provided a processing device in operative communication with an ultrasound device, the processing device configured to receive a selection of a first power mode and generate a first configuration indication associated with the first power mode, wherein the first configuration indication is associated with a first configuration that includes collecting ultrasound data with a first portion of an elevational aperture of an ultrasonic transducer array of the ultrasound device and processing that ultrasound data by the ultrasound device with a first resolution.

In some embodiments, the processing device is further configured to receive a selection of a second power mode and generate a second configuration indication associated with the second imaging depth, wherein the second configuration indication is associated with a second configuration that includes collecting ultrasound data with a second portion of the elevational aperture of the ultrasonic transducer array and processing that ultrasound data by the ultrasound device with a second resolution. The first portion of the elevational aperture is larger than the second portion of the elevational aperture and the first resolution is coarser than the second resolution or the second portion of the elevational aperture is larger than the first portion of the elevational aperture and the second resolution is coarser than the first resolution.

In some embodiments, the first power mode is a low power mode, the second power mode is a non-low power mode, the second portion of the elevational aperture is larger than the first portion of the elevational aperture, and the second resolution is coarser than the first resolution.

According to an aspect of the present disclosure, there is provided an ultrasound device, comprising an ultrasonic transducer array, configurable processing circuitry coupled to the ultrasonic transducer array, and control circuitry coupled to the configurable processing circuitry and configured to set the configurable processing circuitry to a first configuration exhibiting a first elevational aperture percentage and first resolution and then to a second configuration exhibiting a second elevational aperture percentage different than the first elevational aperture percentage and a second resolution different than the first resolution.

In some embodiments, first elevational aperture percentage is greater than the second elevational aperture percentage, and the first resolution is lower than the second resolution.

In some embodiments, first elevational aperture percentage is less than the second elevational aperture percentage, and the first resolution is greater than the second resolution.

In some embodiments, the configurable processing circuitry comprises a switch circuit electrically between the ultrasound transducer array and a plurality of summation circuits.

In some embodiments, the ultrasound device further comprises a plurality of analog-to-digital converters (ADCs) coupled to output terminals of the summation circuits.

In some embodiments, the control circuitry is configured to set the configurable processing circuitry to the second configuration in response to receiving a configuration selection signal.

According to an aspect of the present disclosure, there is provided an ultrasound device, comprising a housing, an ultrasonic transducer array disposed within the housing, and configurable processing circuitry disposed within the housing and coupled to the ultrasonic transducer array, configured to process output signals of the ultrasonic transducer array, and configurable in a first configuration exhibiting a first elevational aperture percentage and first resolution and a second configuration exhibiting a second elevational aperture percentage different than the first elevational aperture percentage and a second resolution different than the first resolution.

According to an aspect of the present disclosure, there is provided an ultrasound device, comprising an ultrasonic transducer array and control circuitry configured to receive a first indication to configure the ultrasound device in a first configuration that includes processing data from k1% of an elevational aperture of the ultrasonic transducer array by coupling n1 output terminals from analog receive circuits to first and second analog combination circuits, configure the ultrasound device in the first configuration, receive a second indication to configure the ultrasound device in a second configuration that includes processing data from k2% of the elevational aperture of the ultrasonic transducer array by coupling n2 output terminals from analog receive circuits to the first and second analog combination circuits, wherein n2 is greater than n1 and k2 is greater than k1 or n2 is less than n1 and k2 is less than k1, and configure the ultrasound device in the second configuration.

According to an aspect of the present disclosure, there is provided an ultrasound device, comprising a plurality of ultrasonic transducers, a plurality of analog receive circuits including first and second analog receive circuits each configured to receive and/or process an analog ultrasound signal from one or more corresponding ultrasonic transducers of the plurality of ultrasonic transducers, a plurality of analog combination circuits including first and second analog combination circuits each configured to output a single analog output by combining multiple analog inputs, switching circuitry comprising a plurality of switches including first and second switches each switchably coupling an output of a particular analog receive circuit of the plurality of analog receive circuits to an input of a particular analog combination circuit of the plurality of analog combination circuits. The control circuitry is configured, when configuring the ultrasound device in the first and/or second configurations, to control the switching circuitry to cause particular outputs of the plurality of analog receive circuits to be coupled as inputs to particular analog combination circuits of the plurality of analog combination circuits and an output of a first analog receive circuit of the plurality of analog receive circuits is switchably coupled to inputs of multiple but not all analog combination circuits of the plurality of analog combination circuits.

According to an aspect of the present disclosure, there is provided an ultrasound device, comprising a plurality of ultrasonic transducers, a plurality of analog receive circuits including first and second analog receive circuits each configured to receive and/or process an analog ultrasound signal from one or more corresponding ultrasonic transducers of the plurality of ultrasonic transducers, a plurality of analog combination circuits including first and second analog combination circuits each configured to output a single analog output by combining multiple analog inputs, switching circuitry comprising a plurality of switches including first and second switches each switchably coupling an output of a particular analog receive circuit to an input of a particular analog combination circuit, and control circuitry configured to receive a first indication to configure an ultrasound device in a first configuration that includes coupling an output of a particular analog receive circuit of the plurality of analog receive circuits to a first analog combination circuit of the plurality of analog combination circuit, configure the ultrasound device in the first configuration, receive a second indication to configure an ultrasound device in a second configuration that includes coupling the output of the particular analog receive circuit of the plurality of analog receive circuits to a second analog combination circuit of the plurality of analog combination circuit, wherein the first and second analog combination circuits are different, and configure the ultrasound device in the second configuration.

According to an aspect of the present disclosure, there is provided a method of operating any of the ultrasound devices of any of the preceding aspects.

According to an aspect of the present disclosure, there is provided a method of operating any of the processing devices of any of the preceding aspects.

Various aspects of the present disclosure may be used alone, in combination, or in a variety of arrangements not explicit in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which an example has been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, comprising:
an ultrasonic transducer array comprising a plurality of ultrasonic transducers;
a plurality of analog receive circuits each configured to receive and/or process an analog ultrasound signal from one or more corresponding ultrasonic transducers of the plurality of ultrasonic transducers;
a plurality of analog combination circuits each configured to output a single analog output by combining multiple analog inputs;
switching circuitry comprising a plurality of switches each switchably coupling an output of a particular analog receive circuit of the plurality of analog receive circuits to an input of a particular analog combination circuit of the plurality of analog combination circuits;
control circuitry configured to:
receive a first indication to configure the ultrasound device in a first configuration that includes processing data from k1% of an elevational aperture of the ultrasonic transducer array by coupling n1 output terminals from analog receive circuits of the plurality of analog receive circuits to each of multiple analog combination circuits of the plurality of analog combination circuits;
configure the ultrasound device in the first configuration, comprising controlling the switching circuitry to cause particular outputs of the plurality of analog receive circuits to be coupled as inputs to particular analog combination circuits of the plurality of analog combination circuits;

receive a second indication to configure the ultrasound device in a first second configuration that includes processing data from k2% of the elevational aperture of the ultrasonic transducer array by coupling n2 output terminals from analog receive circuits of the plurality of analog receive circuits to each of multiple analog combination circuits of the plurality of analog combination circuits, wherein:

$n_2$ is greater than $n_1$ and $k_2$ is greater than $k_1$; or $n_2$ is less than $n_1$ and $k_2$ is less than $k_1$; and configure the ultrasound device in the second configuration, comprising controlling the switching circuitry to cause particular outputs of the plurality of analog receive circuits to be coupled as inputs to particular analog combination circuits of the plurality of analog combination circuits, wherein an output of a first analog receive circuit of the plurality of analog receive circuits is switchably coupled to inputs of multiple but not all analog combination circuits of the plurality of analog combination circuits.

2. The ultrasound device of claim 1, wherein outputs of fewer than 75% of the plurality of analog receive circuits are switchably coupled to inputs of all analog combination circuits of the plurality of analog combination circuits.

3. The ultrasound device of claim 1, wherein:

the output of the first analog receive circuit of the plurality of analog receive circuits is switchably coupled to inputs of a first number of analog combination circuits of the plurality of analog combination circuits;

an output of a second analog receive circuit of the plurality of analog receive circuits is switchably coupled to inputs of a second number of analog combination circuits of the plurality of analog combination circuits; and the first and second numbers are different.

4. The ultrasound device of claim 1, wherein:

when k2 is less than k1:
k1 is 100 and k2 is 50;
k1 is 100 and k2 is 25; or
k1 is 50 and k2 is 25;
when k2 is greater than k1:
k1 is 50 and k2 is 100;
k1 is 25 and k2 is 100; or
k1 is 25 and k2 is 50;
when $n_2$ is less than $n_1$:
n1 is 8 and n2 is 4;
n1 is 8 and n2 is 2; or
n1 is 4 and n2 is 2; and
when n2 is greater than n1:
n1 is 4 and n2 is 8;
n1 is 2 and n2 is 8; or
n1 is 2 and n2 is 4.

5. The ultrasound device of claim 1, wherein the control circuitry is configured, when receiving the indication to configure the ultrasound device in the first configuration, to receive the indication based on:

(a) a user selection of an anatomy for imaging;
(b) a user selection of an imaging depth;
(c) a power level of the ultrasound device; or
(d) a user selection of a power mode for the ultrasound device.

6. The ultrasound device of claim 1, wherein:

the first configuration is a configuration associated with imaging a heart and/or the second configuration is a configuration associated with imaging an abdomen; and $n_2$ is greater than $n_1$ and $k_2$ is greater than $k_1$.

7. The ultrasound device of claim 1, wherein:

the first configuration is a configuration associated with imaging at a first imaging depth;

the second configuration is a configuration associated with imaging at a second imaging depth;

the first imaging depth is deeper than the second imaging depth; and $n_2$ is less than $n_1$ and $k_2$ is less than $k_1$.

8. The ultrasound device of claim 1, wherein:

the first configuration is a configuration associated with imaging at a first power level of the ultrasound device;

the second configuration is a configuration associated with imaging at a second power level of the ultrasound device;

the first power level is greater than the second power level; and $n_2$ is less than $n_1$ and $k_2$ is less than $k_1$.

9. A method of controlling an ultrasound device comprising an ultrasonic transducer array comprising a plurality of ultrasonic transducers, a plurality of analog receive circuits each configured to receive and/or process an analog ultrasound signal from one or more corresponding ultrasonic transducers of the plurality of ultrasonic transducers, a plurality of analog combination circuits each configured to output a single analog output by combining multiple analog inputs, and switching circuitry comprising a plurality of switches each switchably coupling an output of a particular analog receive circuit of the plurality of analog receive circuits to an input of a particular analog combination circuit of the plurality of analog combination circuits, the method comprising:

receiving, with control circuitry, a first indication to configure the ultrasound device in a first configuration that includes processing data from $k_1$% of an elevational aperture of the ultrasonic transducer array by coupling $n_1$ output terminals from analog receive circuits of the plurality of analog receive circuits to each of multiple analog combination circuits of the plurality of analog combination circuits;

configuring, with the control circuitry, the ultrasound device in the first configuration, comprising controlling the switching circuitry to cause particular outputs of the plurality of analog receive circuits to be coupled as inputs to particular analog combination circuits of the plurality of analog combination circuits;

receiving, with the control circuitry, a second indication to configure the ultrasound device in a second configuration that includes processing data from $k_2$% of the elevational aperture of the ultrasonic transducer array by coupling $n_2$ output terminals from analog receive circuits of the plurality of analog receive circuits to each of multiple analog combination circuits of the plurality of analog combination circuits, wherein:

$n_2$ is greater than $n_1$ and $k_2$ is greater than $k_1$; or $n_2$ is less than $n_1$ and $k_2$ is less than $k_1$; and configuring, with the control circuitry, the ultrasound device in the second configuration, comprising controlling the switching circuitry to cause particular outputs of the plurality of analog receive circuits to be coupled as inputs to particular analog combination circuits of the plurality of analog combination circuits, wherein an output of a first analog receive circuit of the plurality of analog receive circuits is switchably coupled to inputs of multiple but not all analog combination circuits of the plurality of analog combination circuits.

10. The method of claim 9, wherein:
outputs of fewer than 75% of the plurality of analog receive circuits are switchably coupled to inputs of all analog combination circuits of the plurality of analog combination circuits;
the output of the first analog receive circuit of the plurality of analog receive circuits is switchably coupled to inputs of a first number of analog combination circuits of the plurality of analog combination circuits;
an output of a second analog receive circuit of the plurality of analog receive circuits is switchably coupled to inputs of a second number of analog combination circuits of the plurality of analog combination circuits; and
the first and second numbers are different.

11. The method of claim 9, wherein receiving, with the control circuitry, the indication to configure the ultrasound device in the first configuration, comprises receiving, with the control circuitry, the indication based on:
(a) a user selection of an anatomy for imaging;
(b) a user selection of an imaging depth;
(c) a power level of the ultrasound device; or
(d) a user selection of a power mode for the ultrasound device.

12. The method of claim 9, further comprising:
imaging a heart using the first configuration and/or imaging an abdomen using the second configuration,
wherein $n_2$ is greater than $n_1$ and $k_2$ is greater than $k_1$.

13. The method of claim 9, further comprising:
imaging at a first imaging depth using the first configuration; and
imaging at a second imaging depth using the second configuration, wherein:
the first imaging depth is deeper than the second imaging depth; and
$n_2$ is less than $n_1$ and $k_2$ is less than $k_1$.

14. The method of claim 9, further comprising:
imaging at a first power level of the ultrasound device using the first configuration; and
imaging at a second power level of the ultrasound device using the second configuration, wherein:
the first power level is greater than the second power level; and
$n_2$ is less than $n_1$ and $k_2$ is less than $k_1$.

15. An ultrasound device, comprising:
an ultrasonic transducer array;
analog receive circuits each of which is configured to receive and/or process an analog ultrasound signal from one or more corresponding ultrasonic transducers of the plurality of ultrasonic transducers;
analog combination circuits each of which is configured to output a single analog output by combining multiple analog inputs;
control circuitry configured to:
receive a first indication to configure the ultrasound device in a first configuration that includes processing data from $k_1$% of an elevational aperture of the ultrasonic transducer array by coupling $n_1$ output terminals from the analog receive circuits to each of multiple analog combination circuits;
configure the ultrasound device in the first configuration;
receive a second indication to configure the ultrasound device in a second configuration that includes processing data from $k_2$% of the elevational aperture of the ultrasonic transducer array by coupling $n_2$ output terminals from the analog receive circuits to each of multiple analog combination circuits, wherein:
$n_2$ is greater than $n_1$ and $k_2$ is greater than $k_1$; or
$n_2$ is less than $n_1$ and $k_2$ is less than $k_1$; and
configure the ultrasound device in the second configuration,
wherein an output of one analog receive circuit of the analog receive circuits is switchably coupled to inputs of a portion of analog combination circuits.

16. The ultrasound device of claim 15, wherein:
when $k_2$ is less than $k_1$:
k1 is 100 and k2 is 50;
k1 is 100 and k2 is 25; or
k1 is 50 and k2 is 25;
when k2 is greater than k1:
k1 is 50 and k2 is 100;
k1 is 25 and k2 is 100; or
k1 is 25 and k2 is 50;
when $n_2$ is less than $n_1$:
n1 is 8 and n2 is 4;
n1 is 8 and n2 is 2; or
n1 is 4 and n2 is 2; and
when n2 is greater than n1:
n1 is 4 and n2 is 8;
n1 is 2 and n2 is 8; or
n1 is 2 and n2 is 4.

17. The ultrasound device of claim 15, wherein the control circuitry is configured, when receiving the indication to configure the ultrasound device in the first configuration, to receive the indication based on:
(a) a user selection of an anatomy for imaging;
(b) a user selection of an imaging depth;
(c) a power level of the ultrasound device; or
(d) a user selection of a power mode for the ultrasound device.

18. The ultrasound device of claim 15, wherein:
the first configuration is a configuration associated with imaging a heart and/or the second configuration is a configuration associated with imaging an abdomen; and
$n_2$ is greater than $n_1$ and $k_2$ is greater than $k_1$.

19. The ultrasound device of claim 15, wherein:
the first configuration is a configuration associated with imaging at a first imaging depth;
the second configuration is a configuration associated with imaging at a second imaging depth;
the first imaging depth is deeper than the second imaging depth; and
$n_2$ is less than $n_1$ and $k_2$ is less than $k_1$.

20. The ultrasound device of claim 15, wherein:
the first configuration is a configuration associated with imaging at a first power level of the ultrasound device;
the second configuration is a configuration associated with imaging at a second power level of the ultrasound device;
the first power level is greater than the second power level; and
$n_2$ is less than $n_1$ and $k_2$ is less than $k_1$.

* * * * *